United States Patent
Simpson et al.

(10) Patent No.: US 10,610,567 B2
(45) Date of Patent: Apr. 7, 2020

(54) PAX6 MINIPROMOTERS

(71) Applicant: The University of British Columbia, Vancouver (CA)

(72) Inventors: Elizabeth M. Simpson, Vancouver (CA); Wyeth W. Wasserman, Vancouver (CA); Jack Hickmott, Vancouver (CA); Robert Molday, Vancouver (CA)

(73) Assignee: University of British Columbia, Vancouver, BC (CA)

( * ) Notice: Subject to any disclaimer, the term of this patent is extended or adjusted under 35 U.S.C. 154(b) by 207 days.

(21) Appl. No.: 15/415,712

(22) Filed: Jan. 25, 2017

(65) Prior Publication Data

US 2017/0209538 A1    Jul. 27, 2017

Related U.S. Application Data

(60) Provisional application No. 62/286,988, filed on Jan. 26, 2016.

(51) Int. Cl.
| | |
|---|---|
| C12N 15/11 | (2006.01) |
| A61K 31/7088 | (2006.01) |
| A61K 38/17 | (2006.01) |
| C07K 14/47 | (2006.01) |
| A61K 48/00 | (2006.01) |
| C12N 15/86 | (2006.01) |
| A61K 39/00 | (2006.01) |

(52) U.S. Cl.
CPC ...... *A61K 38/1709* (2013.01); *A61K 39/0011* (2013.01); *A61K 48/0058* (2013.01); *C07K 14/4702* (2013.01); *C12N 15/86* (2013.01); *A61K 2039/505* (2013.01); *A61K 2039/53* (2013.01); *A61K 2039/572* (2013.01); *C12N 2750/14143* (2013.01); *C12N 2830/008* (2013.01)

(58) Field of Classification Search
None
See application file for complete search history.

(56) References Cited

PUBLICATIONS

Chen et al., Engineering Human Stem Cell Lines with Inducible Gene Knockout using CRISPR/CAS9 . Cell Stem Cell. Aug. 6, 2015; 17(2): 233-244 (Year: 2015).*
Newman et al., Efficient conditional knockout targeting vector construction using co-selection BAC recombineering (CoSBR). Nucleic Acids Research, 2015, vol. 43, No. 19, pp. 1-11. (Year: 2015).*
Xu et al., Regulation of Pax6 expression is conserved between mice and flies. Development 126, 383-395 (1999) (Year: 1999).*

(Continued)

*Primary Examiner* — Christopher M Babic
*Assistant Examiner* — Arthur S Leonard
(74) *Attorney, Agent, or Firm* — Pamela J. Sherwood; Bozicevic, Field & Francis LLP

(57) ABSTRACT

The present invention provides novel nucleic acid sequence compositions and methods relating to minimal human PAX6 promoters. The invention is based in part on the surprising discovery that certain minimal PAX6 promoter elements are capable of expressing in specific cell types in cells eye.

6 Claims, 20 Drawing Sheets
(16 of 20 Drawing Sheet(s) Filed in Color)
Specification includes a Sequence Listing.

(56) References Cited

PUBLICATIONS

Bainbridge et al., "Long-term effect of gene therapy on Leber's congenital amaurosis", New England Journal of Medicine, May 14, 2015, pp. 1887-1897, vol. 372 No. 20, Massachusetts Medical Society, Waltham, MA.
Chow et al., "Pax6 induces ectopic eyes in a vertebrate", Development, Sep. 7, 1999, pp. 4213-4222, 126, The Company of Biologists Limited, Cambridge, United Kingdom.
De Leeuw et al., "Targeted CNS delivery using human MiniPromoters and demonstrated compatibility with adeno-associated viral vectors", Molecular Therapy, 2014, vol. 1, 2014, Article 5, The American Society of Gene & Cell Therapy, Milwaukee, WI.
Manuel et al. Overexpression of Pax6 results in microphthalmia, retinal dysplasia and defective retinal ganglion cell axon guidance BMC Developmental Biology, May 28, 2008, pp. 1-21, 8(59), Biomed Central, London, United Kingdom.
Portales-Casamar et al., "A regulatory toolbox of MiniPromoters to drive selective expression in the brain", PNAS, Sep. 21, 2010, pp. 16589-16594, pp. 1-15, vol. 107, No. 38, PNAS, Washington, DC.
Schedl et al. "Influence of PAX6 Gene Dosage on Development: Overexpression Causes Severe Eye Abnormalities", Cell, Jul. 12, 1996, pp. 71-82, vol. 86, Issue 1, Elsevier Inc., Amsterdam, Netherlands.

\* cited by examiner a
PAX6 mRNA transcripts b
All human tissues

CNS tissues

Ocular tissues c
Promoters: P0    P1       Pα   (P4)

Figure 10

SEQUENCE LISTING

<160> NUMBER OF SEQ ID NOS: 21

<210> SEQ ID NO 1
<211> LENGTH: 2134
<212> TYPE: DNA
<213> ORGANISM: Homo sapiens

<400> SEQUENCE: 1

```
cagactggga attgccgtgg ctatgcccga agtttggaaa gtctctctcg gtctctttct    60
gggacagcct ttcttttcc gggaagcttc ctgtgcctag aggtgggct ctgtagctgg    120 aggggtagat ggaacttgcg aagcaaagga aggcaataaa aggaagttag gagaaaccgg    180
aaacgtgggc caggccttgc tctgttggag aagcggtgtc cccgcaaagt ccctgcttgc    240
gctggtcccg gccggagccc agatccccca aacgcctgtc acttctcatc gagttgaggc    300
tccggccccc acccgcgcct tggtgagggc cccccctcag ccccaagcct tcggctaccc    360
tgaaaacgcg gctcccctcg aagggaaac aagtgcagtt caatctcgtc tgagtgatct    420
acaaataagg acgaaaggg tcgttttatc acggtcccgt ttgtcgtgac gatgcaattt    480
cccggagcgg agcactgtca caaagtgaca aggctgccac aagcgccccg actgatcttt    540
tcaattagcc ttccatgcat gatccggagc gacttccgcc tatttccaga aattaagctc    600
aaacttgacg tgcagctagt tttatttaa agacaaatgt cagagaggct catcatattt    660 tccccctct tctatatttg gagcttattt attgctaaga agctcaggct cctggcgtca    720
atttatcagt aggctccaag gagaagagag gagaggagag gagagctgaa cagggagcca    780 cgtctttcc tgggagggct gctatctaag tcggggctgc aggttggaga ttttaagga    840 agtggaaatt ggcaattggc tttgtgtgtc tgtggttttt gggggagggg actacaaaga    900
ggggctaact ccctctccct attctctaag gttggaccac agggatgagg ttgtgagata    960
caaagataaa ggagggatgg ggaacactat gatgtggtat ttttctttc tgtttttct   1020 ttttgataat atctatcctt ggctaagggg agggcggagt tcagcggcgg aaataaagcg   1080
agcagtggct ggtgcgaacc gactcccggc tctaagcctt acttgcggtg gccggacttg   1140
tctgtggctg aagccgagcc cgggctctga ctctcacgtc tgcactggag gtgcggaaac   1200
ctggactggg gttcaccagc cacatactgg ctgctctggt tgttctctcc tcttccttct   1260
tctattctaa ccaaacaaaa cccaactcga tgcttgtgcc aggccttggc cagtttggac   1320
ggtgatggaa acatttctgg attttagcgt ctaagggagc actcaagggc tgtaaggttt   1380
gctatcactg tcccaacact gcagagacct tgaaggttca gtgtgggatc tgtagaaccc   1440
atggtttgcg gtgacactca gaggggatct ttgggagatt tatagagccg gttcttagcg   1500
ctttgtgggt tcagaggctg gctgcagtgt ttatgaagag gggcagtggg ctggggacac   1560 tgctgggggtt atggctgtag tgaggtccat gtgtacttgt tccttggcat gtgtctgact   1620
ctgtgttgct gctgcagtac agtgggcagg ggcacggttg cttggactgg gctgcccgat   1680
cttggggatc ggaggagggg acagggtgat tacccagaga ggtagctggc cagcctaagg   1740
gcagagatct tggggcccta gtgcccgaag gtgcggagga gcgcactcgg caagactagt   1800
ttcctgggga tcgactctac gccatacagg acggcggccc aggctggacc gggccgggct   1860
agagcagtca caggccgggc caaggaaggc caaagcaggg gttggagccg ccggaccct   1920 gggtggggag aagcaggctc cgcccgcc ggaaaactag tcggcgcaga gctgtgccca   1980
actctagccg ccatgacgtc acgcgggccg ggcagccaat gaggacggcg ctggcgtgga   2040
tattaaggaa agttagcgcc tgcctgagca ccctcttttc ttatcattga catttaaact   2100
ctggggcagg tcctcgcgta gaacgcggct gtca                               2134
```

<210> SEQ ID NO 2
<211> LENGTH: 2049
<212> TYPE: DNA
<213> ORGANISM: Homo sapiens

<400> SEQUENCE: 2

```
tgagtaactt agttatgaat aaataaatag tgcaatgtaa aaatattaga ccctaagttc      60
aatttataaa atgaagattt ttatataaaa attacggtca aggtgtcata tttaattat      120
atttctcaaa gaaagatgat tcatttgata taactaatta taagtttcat atcctacgtg     180
ttgatgacca cacagaaact ttaagacata taatagccaa atatgaatct actcttcctt     240
gccaaatgaa gcaatgatgt tctgccagcc aaactaacag gaagcatgtg aaatgaacac     300
agaagcaaac aggacttaca ctgcctaagg gaaagtcagc aagatggcag tttcaatcat     360
ttggaataat actaaagcag ccttaggctt ttctcagaat ggaaacatgt cactattact     420
gcaatatttc aacaaatcag aatgcagaga aaagaacact tatgcaacca catcttggaa     480
gggcacttta ctcaacattt aagtggaaaa caattataaa gaaatttcag aaaaactgtc     540
agtgaacata aatgactcag ggaaaaatgt tttttcttcc aaagtgctta atagattttt     600
caaaagctta ccacttagaa acaatttcct tatatattct ccttaaggaa ttattaatat     660
aaagacaaat ttatataaag aggtaagtga aaagtttgat attcaggttg ccggtaagaa     720
atgctcattt ttccccagta cagtactatt actttggaag gtttgatcaa agggaataag     780
ctttcacaac atttatatag gaagttaaaa aatacttcaa atattttggg aacttaccta     840
atcaggatac ttttagcatg tgtctagtca tgtagccatc tttggtcaat catcaaaaaa     900
tcaagggaa attggcatga ctcaacccta actttaatac cgcatgattg tgtcgtgtaa      960
gcttgttttg tgtgagagct gctgtggttt tagcagagag attaacaacc ggacctaagc    1020
tggcctccaa accttgccct gctgatgcct caagctcttt gaagtctgac catcatacct    1080
ggcaaaacaa cagtgggaac taggatggtg tcagatctaa tcaaattgtt tgctgcagca    1140
tagctaacta tggggttcac taattggccc aattgcggat tatacctttt gctacagatt    1200
caagacaata atttagttaa atgatgtttt ttttttttctt atctcttcta attaagattc   1260
caaagtggga agaaatagga ttagacagat tctcaaaact gtgttctcct taaggtggta    1320
tgcactttg ataggttaac tatggcatgt gaaatatata aagtgtagta agtattaaac     1380
caacttctga tgattctttg aaacctatgt aatgctatta tatgctgata tcacttgaga    1440
ataaaagcat aaacatgaga atgataatat aatgaatata tcaaaatgta cacatgtaaa    1500
aaattagatt tccattgtta aaaaatgtta atttgggttt attttgaca actgatttaa     1560
tctaaatgaa tagatgccta tgttcaactt tgattcttgg ggatcggagg aggggacagg    1620
gtgattaccc agagaggtag ctggccagcc taagggcaga gatcttgggg ccctagtgcc    1680
cgaaggtgcg gaggagcgca ctcggcaaga ctagtttcct ggggatcgac tctacgccat    1740
acaggacggc ggcccaggct ggaccgggcc gggctagagc agtcacaggc cgggccaagg    1800
aaggccaaag caggggttgg agccggccgg accctgggtg gggagaagca ggctcccgcc    1860
cggccggaaa actagtcggc gcagagctgt gcccaactct agccgccatg acgtcacgcg    1920
ggccgggcag ccaatgagga cggcgctggc gtggatatta aggaaagtta gcgcctgcct    1980
gagcacctc ttttcttatc attgacattt aaactctggg gcaggtcctc gcgtagaacg     2040
cggctgtca                                                            2049
```

<210> SEQ ID NO 3
<211> LENGTH: 2076
<212> TYPE: DNA
<213> ORGANISM: Homo sapiens

<400> SEQUENCE: 3

-continued

```
ggacacatcg accacattgt atgtaggtgg tgtttgttga accattttgt tggcctggga    60
atgtgagggt tgtgtatgtc aggagcggta tgaaggtggc tggtgggtgc gtgtgtgtgt   120
ttgtgggcag cactgtgtgc ataagaacga gctgcgtggt gcactattca aatttgacat   180
tagaatgcag ggagagcccc cttgtagaag tgtgacaaga taacgcactg acagactgcg   240
aggttaacat aattgtatcc tgttgctttt tgctgtaatt gacaaattat gtgactatga   300
gtagggtgca catgaaaagg tgagcaggga gatgcagggc gagtcgggga tggggcattg   360
gaagtggtgg tctcccaact aaaaccaccc cactatcctt gcccctcccc cgttcgcccc   420
tctgggtccc actttctcac tctctgtggg tggcgactat gtggaagtgg tgaggtgaag   480
atactgtgag caggacggcg ggatgccggg agccgctctg gtctgggagg agagatggga   540
cctgaaacac cccaggttct gtgagaaggg ctggaggaag aagagcgggg gatgggggg    600 gtggggcgga gggagggtc agttggctcc cctccgctcc cctccacacc ccgaggtagc    660
ttggtcaaga ataggaaaca gtttactccg aagattaatc ggtatttgtt gtcctcgtga   720
caaggagata atatgcggga taatgggacg tggcgtctca ctcccaggag cacaacggag   780
ccgaggggct cggggccagg ggcggcgcgc gggactgcga ggaggctgcc ggcgcatccg   840
tgagctctcg gaccggctcc ggatgcccgg cgcctccatg gagtcgggcg agggaaggga   900
aaatcggtaa cagtatgcga aatatctggt acaaaggatg cttctgtcac tcgcaagaat   960
ttgttatggg aacaatcctg tcgctctgta attgctcatt agagaacgtt ttgtttctca  1020
ttaaggcgac atgaataagc gtctagttga aggagacagc tgtagaaatg ttccacaaga  1080
gacctctgga cacgattcgg caccaattgc caattagaca tgtcagtttt aagagcagaa  1140
aacaatatag gacggacact gggaagatag ggagcaaagc gctcgcttct tgtttcccag  1200
cgcggccgct cggccggcgg aggcctcctg acgcgcgggg cccgggctcc cctgggcgac  1260
cccgcccgca cgggcccga acccgccgcc tccgcgagct cagagggccc ccaggcccgc  1320
tcccgcctct ggtgagacta gcgattgacc ccaccgagtg taggcaaccc catccctgcc  1380
tgacttttga aaccgtagga ttcccacttg tagacactgg acacacccaa gtgacacccg  1440
aacttcgcac tcacgagcgt ccaccctcc gcccccagca atctgaggtc ctggtgatcc   1500
ctcccctgac aagagtctgg cccacttagt ccgagaagtc ttggggaggg actcagggca  1560
cggtggccta ggcctgggag ggctgagccc agagcctcca ctccgggctc tccccggtgc  1620 gtcttggga tcggaggagg ggacagggtg attacccaga gaggtagctg gccagcctaa   1680
gggcagagat cttggggccc tagtgcccga aggtgcggag gagcgcactc ggcaagacta  1740
gtttcctggg gatcgactct acgccataca ggacggcggc ccaggctgga ccgggccggg  1800
ctagagcagt cacaggccgg gccaaggaag gccaaagcag gggttggagc cggccggacc  1860
ctgggtgggg agaagcaggc tcccgcccgg ccggaaaact agtcggcgca gagctgtgcc  1920
caactctagc cgccatgacg tcacgcgggc cgggcagcca atgaggacgg cgctggcgtg  1980
gatattaagg aaagttagcg cctgcctgag caccctcttt tcttatcatt gacatttaaa  2040
ctctggggca ggtcctcgcg tagaacgcgg ctgtca                            2076
```

<210> SEQ ID NO 4
<211> LENGTH: 2146
<212> TYPE: DNA
<213> ORGANISM: Homo sapiens

<400> SEQUENCE: 4

```
ctccactcct atcccatccc cacgtccccg aaatgaataa tgcaggcagg agccaagatt      60
tctgcattag cgccacgttg ccccggcggc tggcgctagg atcccgaagt cggataatgg     120
aaattaaact gttgttgtgt ggcggggatg tcattatgtg actgttcata ttcaaagtca     180
ggcagcaatg aattgtaatc atttcaatta tcttcaatac actttcttta ggacacaagt     240
tgtcaaggat aaaaaaaaaa agtacattct gcggctccg  tgggtccatt ttccagatgg     300
tttgttactc ttgctgcctg atttagtttc ggcttttatt ccccagcctc agattctctt     360
gcagagactc cgccggagtg agcggcttct ctggcgctgc gggccggcta cgctggtcgg     420
caatcggcct ccgtgggcct ggcgtgcgca ttttggttgc tttcaggtat aattaacttt     480
gaacaacaaa tatgcctgga gctctggatc tagtgtcccc ttggggaagg gggccgtcgt     540
attatactct gcgtccttcc cagcctgggg cggggtgggg gctggctgca gcagctgcac     600
ccactcccca ggcagcgct  cgcgtcaga  aaagcatgtg ctgggctgta cccactcctc     660
cgacagagcc cggaccctct ccttccaacc cagagaactc agggaaaagc cgggatcccc     720
ggagcctgcc gtcctttgtt gaaattaccc tctgcccaat gttcgctccc tcctgtgcct     780
gaacgtgggg ctgcgacaag ttggatgtgg tgtccttgaa gtatcccttc gagcgccctc     840
cgcccccaga ctgggcaaaa agagtagggg tcgcctttga agcccaagtc cgcggctcct     900
atttggacta atcccgatct ttacactaat atcgcctctc gggttttcat tatactcatt     960
tgggaggaaa tgagcttttg ctgggcaaat agcaccctgc accccacttc tcatagctgt    1020
gcaggcccgg ggcctgaaca accccgcagg caatccggga gctgccgata ttatatttgt    1080
gaaatgtcct tttgttgagg cttttaacac cttcttataa cgaatcattt gttctttttct   1140 ctttaatttt gatagacaat tagccatcag agatacacca gttgactgta accgagcatt    1200
aaactcgcct ttatgtaacg ctaatttagc atagctgctt tgtttaactt tgctatataa    1260
gaaccaggtt ttgtagcaaa aaaaaaaagg tgtaatttta tgtggggctt catttctttt    1320
ggccctgtac acagctagcc ctctcctctt tgtgaagcgt tctgctgggg cctgacgcca    1380
tttcccgtgc ctagcacctg caggctgggg ggagagaggg aattagcatt gatatagatt    1440
tagttgaaat gtaatctctt aaatctgtcc aagattcggg gagataatta cactttcact    1500
gaattgccag gggtcagcgt ctctgaggac ctgaggagtt gatttactaa caatagtgtt    1560
acataaaaaa tggcgtttga gattataatg ttaatggctg cggtcgctgg ggaatgcgcc    1620
cgcttccaac taattccatg taacttgttt ttttttcctcc cttttcctcc ctcccttttct   1680 tccaggctcc gtcttgggga tcggaggagg ggacagggtg attacccaga gaggtagctg    1740
gccagcctaa gggcagagat cttggggccc tagtgcccga aggtgcggag gagcgcactc    1800
ggcaagacta gtttcctggg gatcgactct acgccataca ggacggcggc ccaggctgga    1860
ccgggccggg ctagagcagt cacaggccgg gccaaggaag gccaaagcag gggttggagc    1920
cggccggacc ctgggtgggg agaagcaggc tcccgcccgg ccggaaaact agtcggcgca    1980
gagctgtgcc caactctagc cgccatgacg tcacgcgggc cgggcagcca atgaggacgg    2040
cgctggcgtg gatattaagg aaagttagcg cctgcctgag caccctcttt tcttatcatt    2100
gacatttaaa ctctggggca ggtcctcgcg tagaacgcgg ctgtca                   2146
```

<210> SEQ ID NO 5
<211> LENGTH: 2098
<212> TYPE: DNA
<213> ORGANISM: Homo sapiens

<400> SEQUENCE: 5

```
ttaataaatg tcacattttg ccagatcaaa acaataggtt aatatgttta taaacatagt        60
atgtccagtt attaagtagc aaaagttcta aatactaag aatctcctgg ctataagaat        120
ataatcatca aatatctggt agggtttttt tttttaattc tttaattact ggaaatctag       180
tattcctttt agcccctgac agggtggtag attagaaaac tgtgattata tgctatgatg      240
tcttagacaa ttttttgctt ggcagatcta gataagctga aaatgttttt tgtaaaattt     300
tgcaattttg aaactctcat tttatacaat ggtaatgccc accagtttaa aactaatctt    360
tgaagaagag aatgggaaat ataaaacagt caagaaaatt tatcagcctg ctatatcccc   420
tgttagaaag aggtcaaata taataaaaga ttttcatttt ctgggaacat gattacaact   480
gagcttacta atattcttgt ttcttaagtc cctttataaa gatggcctaa gaatgaaaaa   540
ttaaagaggg ctggtcaatg ttacctgact tggtattatg aaacacatag tagcctgtgt   600
caccaaacat tctgttgaaa tgactggtta actcacacct agagcagtat ttgaaactcc   660
ttcataagtt ggaatgtgtg ttatataaag aatgtttcag cattatacaa ggaatgtttc   720
agcctttgga tcagtgttgt taaaaagaat cagtaaaaat aattattctt aattgtcttt   780
aatatgttca atcacgtggg cacactaagt atagaaaaac atagtttgga aatgcctatt   840
ttttctaagg caattttttca ttcaatggtg agaaaataat ccagattgat tccttacttt   900
cagttctgtg ccacagggga tggtcctact ccaggaataa caggggcttc agaggccata   960
aacatgttcc tctcaatatt tctttagcca aagaccatta tatcaaactc atccaggttg   1020
ggtttcagcc agttattctt cacccaaaca aaaatgtctg ccagacattc caacagctgg   1080
gatacagttc acaatgagtc aacttgaaaa tgattcattg tgctgagtac tgaacaatgt   1140
tggggtgggg gtggggtgtg gctgggttgg tagtaaaggg tgagaacaag tgggagatga   1200
agaataacca tgtggctccc ccattaagaa gaatcatgga taataaccag caggctctta   1260
tcatttcatt tttaggataa actcaactgg gaagagtact cctgtcatgg accctcagat   1320
gaacaagcat ttataaaggc tactgacaat atttcttaat caaaaggtca gatttccttt   1380
tatctataaa taaagactaa gccttttta tctaaatatc tgaaactaaa atgatacaag   1440 tcaattttg ttagaactca tctattcaag atttcagtga tataaactag gactttctca   1500
attatatgaa taacagaaat tgcaaggttt aaagatgaga taaatttcca ttctgatagt   1560
acataagcaa agtactgtgt atttaaatgg tcaacctgac atttgcttat ttcaaagagg   1620
atttacttct ttcatttaat cttacttggg gatcggagga ggggacaggg tgattaccca   1680
gagaggtagc tggccagcct aagggcagag atcttgggc cctagtgccc gaaggtgcgg   1740
aggagcgcac tcggcaagac tagtttcctg gggatcgact ctacgccata caggacggcg   1800
gcccaggctg gaccgggccg ggctagcagca gtcacaggcc gggccaagga aggccaaagc   1860
aggggttgga gccggccgga ccctgggtgg ggagaagcag gctcccgccc ggccggaaaa   1920
ctagtcggcg cagagctgtg cccaactcta gccgccatga cgtcacgcgg gccgggcagc   1980
caatgaggac ggcgctggcg tggatattaa ggaaagttag cgcctgcctg agcaccctct   2040
tttcttatca ttgacattta aactctgggg caggtcctcg cgtagaacgc ggctgtca   2098
```

<210> SEQ ID NO 6
<211> LENGTH: 2087
<212> TYPE: DNA
<213> ORGANISM: Homo sapiens

<400> SEQUENCE: 6

```
gggtgccggg actgagagac aggaaggaag cattggagag ccaacctaga taagggtaac      60
tagtaaccct ctgctgtggc cagtatttac ccaatgctga gaaaaagtcc tcattttcgg     120 tttatttttta tggatttaag ctgtctacca agtagttaaa aagtagacca ggaatggcct    180
tgtagagtaa aatgtgcttc ttgaaattct ttgcttgcag gcaggcagat caataatcac    240
cataggtaaa acagaaaaaa taatgcattt aaaaaaaaac agagagaaat gatgctgtga    300
ctgttttgtt attttacctc tttttggggg gcagacctct tgaatgggct ctttattgta    360
actctctctt cccaattgag ctccccacgg tgccgttgta tcttttttaca gcccctaaca    420 actcacacca gtaacacaat tacctccaga tatttacaac aagaaattac tttctatttt    480
tctccactca cccaaaagac tttttttttt tttcctttgg gaaaggtagg gaggtgttcg    540
tacgggagca gcctcgggga cccctgcact gggtcagggc ttatgaagct agaagcgtcc    600
ctctgttccc tttgtgagtt ggtgggttgt tggtacattt ggttggaagc tgtgttgctg    660
gttagggaga ctcggttttg ctccttgggt tcgaggaaag ctggagaata gaagccattg    720
tttgccgtct gtcggctttg tcgaccacgc tcacccctc ctgttcgtac tttttaaagc    780
agtgaggcga ggtagacagg gtgtgtcaca gtacagttaa aggggtgaag atctaaacgc    840
caaaagagaa gttaatcaca ataagtgagg tttgggataa aaagttgggc ttgccccttt    900
caaagtccca gaaagctggg aggtagatgg agagggggcc attgggaagt ttttttggtg    960
tagggagagg agtagaagat aaagggtaag cagagtgttc ctgcgttcta gacagaaaag   1020 cccccttctga ccatgcatta gtagtactac tccattattc ctgttagaac aagttaaaag   1080
taagggttga gcccaaaggc cccaggaggg gggtcatgtg cgccccagtc actcaggctc   1140
ccctcgcttc tccggttcga gttatgccat caagctaata tattgtgact gctcttctct   1200
cctgtgacaa aggcttgcag ctgcctccaa atcaatagat gtcaaagaaa tatgaaaaca   1260
atcatgacac aaaacttaaa tcctggctgg agcctacata atcagaaatg tgctactgtt   1320
cttcaagcca ccgattaatt tatcccaaac tttagtcaaa ttttttattcc ggtaccttt    1380 tcccagcaga tcctgctacg tctgtcgggt ttgtaatgta atttgtaatt actgcccttc   1440
atgtggtccg gtgccttgaa ccatctttaa ttaaaagcat aattaaggga agatctaaag   1500
aaagacaatt accagatggt ctttttttta gaggcggtag ttgcgcagag aggggctcgg   1560
ggtctgtccc cggaccccca cgccttggga ggggcggcg ggcccgaacg cgcctgcgc    1620 actgaggagg cctcttgggg atcggaggag gggacagggt gattacccag agaggtagct   1680
ggccagccta agggcagaga tcttggggcc ctagtgcccg aaggtgcgga ggagcgcact   1740
cggcaagact agtttcctgg ggatcgactc tacgccatac aggacggcgg cccaggctgg   1800
accgggccgg gctagagcag tcacaggccg ggccaaggaa ggccaaagca ggggttggag   1860
ccggccggac cctgggtggg gagaagcagg ctcccgcccg gccggaaaac tagtcggcgc   1920
agagctgtgc ccaactctag ccgccatgac gtcacgcggg ccgggcagcc aatgaggacg   1980
gcgctggcgt ggatattaag gaaagttagc gcctgcctga gcaccctctt ttcttatcat   2040
tgacatttaa actctggggc aggtcctcgc gtagaacgcg gctgtca                 2087
```

<210> SEQ ID NO 7
<211> LENGTH: 2134
<212> TYPE: DNA
<213> ORGANISM: Homo sapiens

<400> SEQUENCE: 7

```
cagactggga attgccgtgg ctatgcccga agtttggaaa gtctctctcg gtctctttct      60
```

```
gggacagcct tcttttttcc gggaagcttc ctgtgcctag aggtggggct ctgtagctgg      120
aggggtagat ggaacttgcg aagcaaagga aggcaataaa aggaagttag agaaaccgg       180 aaacgtgggc caggccttgc tctgttggag aagcggtgtc cccgcaaagt ccctgcttgc      240
gctggtcccg gccggagccc agatccccca acgcctgtc acttctcatc gagttgaggc       300
tccggccccc acccgcgcct tggtgagggc ccccctcag ccccaagcct tcggctaccc       360
tgaaaacgcg gctcccctcg aaggggaaac aagtgcagtt caatctcgtc tgagtgatct      420
acaaataagg acggaaaggg tcgttttatc acggtcccgt tgtcgtgac gatgcaattt       480 cccggagcgg agcactgtca caaagtgaca aggctgccac aagcgccccg actgatcttt      540
tcaattagcc ttccatgcat gatccggagc gacttccgcc tatttccaga aattaagctc      600
aaacttgacg tgcagctagt tttattttaa agacaaatgt cagagaggct catcatattt      660 tccccctct tctatatttg gagcttattt attgctaaga agctcaggct cctggcgtca       720
atttatcagt aggctccaag gagaagagag gagaggagag gagagctgaa cagggagcca     780
cgtcttttcc tgggagggct gctatctaag tcggggctgc aggttggaga ttttaagga      840 agtgaaaatt ggcaattggc tttgtgtgtc tgtggttttt gggagggggg actacaaaga     900
ggggctaact ccctctccct attctctaag gttggaccac agggatgagg ttgtgagata     960
caaagataaa ggagggatgg ggaacactat gatgtggtat ttttcttttc tgttttttct    1020
ttttgataat atctatcctt ggctaagggg agggcggagt tcagcggcgg aaataaagcg    1080
agcagtggct ggtgcgaacc gactcccggc tctaagcctt acttgcggtg gccggacttg    1140
tctgtggctg aagccgagcc cgggctctga ctctcacgtc tgcactggag gtgcggaaac    1200
ctggactggg gttcaccagc cacatactgg ctgctctggt tgttctctcc tcttccttct    1260
tctattctaa ccaaacaaaa cccaactcga tgcttgtgcc aggccttggc cagtttggac    1320
ggtgatggaa acatttctgg attttagcgt ctaaggagc actcaaggc tgtaaggttt      1380 gctatcactg tcccaacact gcagagacct tgaaggttca gtgtgggatc tgtagaaccc    1440
atggtttgcg gtgacactca gagggatct ttgggagatt tatagagccg gttcttagcg     1500 cttttgtgggt tcagaggctg gctgcagtgt ttatgaagag gggcagtggg ctggggacac   1560
tgctggggtt atggctgtag tgaggtccat gtgtacttgt tccttggcat gtgtctgact    1620
ctgtgttgct gctgcagtac agtgggcagg ggcacggttg cttggactgg gctgcccgat    1680
caccctccga ggactgggag tcccgagtcc agcttagggg gagtgggggc gcgaccccca    1740
acccagaaac cttcacttga ccgctcaagt tcgcggcagc agggcgggcc cgccgaatc     1800 tcggcgtgcg cggagcgggg agatgcaggc gagcgccaga gcccgggctc ggggggcctg   1860
cgccggggag aggagccggg acccaccggc ggagccgaaa acaagtgtat tcatattcaa    1920
acaaacggac caattgcacc aggcggggag agggagcatc caatcggctg gcgcgaggcc    1980
ccggcgctgc tttgcataaa gcaatatttt gtgtgagagc gagcggtgca tttgcatgtt    2040
gcggagtgat tagtgggttt gaaaagggaa ccgtggctcg gcctcatttc ccgctctggt    2100
tcaggcgcag gaggaagtgt tttgctggag gatg                                2134
```

<210> SEQ ID NO 8
<211> LENGTH: 454
<212> TYPE: DNA
<213> ORGANISM: Homo sapiens

<400> SEQUENCE: 8

```
cttgggatc ggaggagggg acagggtgat tacccagaga ggtagctggc cagcctaagg    60
gcagagatct tgggccccta gtgcccgaag gtgcggagga gcgcactcgg caagactagt   120
ttcctgggga tcgactctac gccatacagg acggcggccc aggctggacc gggccgggct   180
agagcagtca caggccgggc caaggaaggc caaagcaggg gttggagccg gccggaccct   240
gggtggggag aagcaggctc ccgcccggcc ggaaaactag tcggcgcaga gctgtgccca   300
actctagccg ccatgacgtc acgcgggccg ggcagccaat gaggacgcg ctggcgtgga    360 tattaaggaa agttagcgcc tgcctgagca ccctcttttc ttatcattga catttaaact   420
ctggggcagg tcctcgcgta gaacgcggct gtca                               454
```

```
<210> SEQ ID NO 9
<211> LENGTH: 454
<212> TYPE: DNA
<213> ORGANISM: Homo sapiens

<400> SEQUENCE: 9
caccctccga ggactgggag tcccgagtcc agcttagggg gagtgggggc gcgaccccca   60
acccagaaac cttcacttga ccgctcaagt tcgcggcagc agggcgggcc gcgccgaatc   120
tcggcgtgcg cggagcgggg agatgcaggc gagcgccaga gcccgggctc gggggccctg   180
cgccggggag aggagccggg acccaccggc ggagccgaaa acaagtgtat tcatattcaa   240
acaaacggac caattgcacc aggcggggag agggagcatc caatcggctg gcgcgaggcc   300
ccggcgctgc tttgcataaa gcaatatttt gtgtgagagc gagcggtgca tttgcatgtt   360
gcggagtgat tagtgggttt gaaaagggaa ccgtggctcg gcctcatttc ccgctctggt   420
tcaggcgcag gaggaagtgt tttgctggag gatg                               454
```

```
<210> SEQ ID NO 10
<211> LENGTH: 634
<212> TYPE: DNA
<213> ORGANISM: Homo sapiens

<400> SEQUENCE: 10
cctgcgttct agacagaaaa gccccttctg accatgcatt agtagtacta ctccattatt   60
cctgttagaa caagttaaaa gtaagggttg agcccaaagg ccccaggagg ggggtcatgt   120
gcgccccagt cactcaggct cccctcgctt ctccggttcg agttatgcca tcaagctaat   180
atattgtgac tgctcttctc tcctgtgaca aaggcttgca gctgcctcca aatcaataga   240
tgtcaaagaa atatgaaaac aatcatgaca caaaacttaa atcctggctg gagcctacat   300
aatcagaaat gtgctactgt tcttcaagcc accgattaat ttatcccaaa ctttagtcaa   360 attttattc cggtaccttt ttcccagcag atcctgctac gtctgtcggg tttgtaatgt     420
aatttgtaat tactgcccctt catgtggtcc ggtgccttga accatcttta attaaaagca   480
taattaaggg aagatctaaa gaaagacaat taccagatgg tcttttttttt agaggcggta   540 gttgcgcaga gaggggctcg gggtctgtcc ccgggacccc acgccttggg aggggcggc    600 gggcccgaac ggcgcctgcg cactgaggag gcct                               634
```

```
<210> SEQ ID NO 11
<211> LENGTH: 1692
<212> TYPE: DNA
<213> ORGANISM: Homo sapiens

<400> SEQUENCE: 11
ctccactcct atcccatccc cacgtccccg aaatgaataa tgcaggcagg agccaagatt   60
```

```
tctgcattag cgccacgttg ccccggcggc tggcgctagg atcccgaagt cggataatgg    120
aaattaaact gttgttgtgt ggcggggatg tcattatgtg actgttcata ttcaaagtca    180
ggcagcaatg aattgtaatc atttcaatta tcttcaatac actttcttta ggacacaagt    240
tgtcaaggat aaaaaaaaaa agtacattct tgcggctccg tgggtccatt ttccagatgg    300
tttgttactc ttgctgcctg atttagtttc ggcttttatt ccccagcctc agattctctt    360
gcagagactc cgccggagtg agcggcttct ctggcgctgc gggccggcta cgctggtcgg    420
caatcggcct ccgtgggcct ggcgtgcgca ttttggttgc tttcaggtat aattaacttt    480
gaacaacaaa tatgcctgga gctctggatc tagtgtcccc ttggggaagg gggccgtcgt    540
attatactct gcgtccttcc cagcctgggg cggggtgggg gctggctgca gcagctgcac    600
ccactcccca ggccagcgct cgcgtcaga aaagcatgtg ctgggctgta cccactcctc    660
cgacagagcc cggaccctct ccttccaacc cagagaactc agggaaaagc cgggatcccc    720
ggagcctgcc gtcctttgtt gaaattaccc tctgcccaat gttcgctccc tcctgtgcct    780
gaacgtgggg ctgcgacaag ttggatgtgg tgtccttgaa gtatcccttc gagcgccctc    840
cgcccccaga ctgggcaaaa agagtagggg tcgcctttga agcccaagtc cgcggctcct    900
atttggacta atcccgatct ttacactaat atcgcctctc gggttttcat tatactcatt    960
tgggaggaaa tgagcttttg ctgggcaaat agcaccctgc accccacttc tcatagctgt   1020
gcaggcccgg ggcctgaaca accccgcagg caatccggga gctgccgata ttatatttgt   1080
gaaatgtcct tttgttgagg cttttaacac cttcttataa cgaatcattt gttcttttct   1140
ctttaatttt gatagacaat tagccatcag agatacacca gttgactgta accgagcatt   1200
aaactcgcct ttatgtaacg ctaatttagc atagctgctt tgtttaactt tgctatataa   1260
gaaccaggtt ttgtagcaaa aaaaaaagg tgtaattttta tgtggggctt catttctttt   1320
ggccctgtac acagctagcc ctctcctctt tgtgaagcgt tctgctgggg cctgacgcca   1380
tttcccgtgc ctagcacctg caggctgggg ggagagaggg aattagcatt gatatagatt   1440
tagttgaaat gtaatctctt aaatctgtcc aagattcggg gagataatta cactttcact   1500
gaattgccag gggtcagcgt ctctgaggac ctgaggagtt gatttactaa caatagtgtt   1560
acataaaaaa tggcgtttga gattataatg ttaatggctg cggtcgctgg ggaatgcgcc   1620
cgcttccaac taattccatg taacttgttt tttttcctcc cttttcctcc ctcccttct    1680 tccaggctcc gt                                                       1692

<210> SEQ ID NO 12
<211> LENGTH: 999
<212> TYPE: DNA
<213> ORGANISM: Homo sapiens

<400> SEQUENCE: 12
gggtgccggg actgagagac aggaaggaag cattggagag ccaacctaga taagggtaac     60
tagtaaccct ctgctgtggc cagtatttac ccaatgctga gaaaaagtcc tcattttcgg    120 tttatttta tggatttaag ctgtctacca agtagttaaa aagtagacca ggaatggcct    180
tgtagagtaa aatgtgcttc ttgaaattct ttgcttgcag gcaggcagat caataatcac    240
cataggtaaa acagaaaaaa taatgcattt aaaaaaaaac agagagaaat gatgctgtga    300
ctgttttgtt attttacctc ttttggggg gcagacctct tgaatgggct ctttattgta    360
actctctctt cccaattgag ctccccacgg tgccgttgta tcttttttaca gccccctaaca   420
```

| | |
|---|---|
| actcacacca gtaacacaat tacctccaga tatttacaac aagaaattac ttttctattt | 480 |
| tctccactca cccaaaagac ttttttttttt tttcctttgg gaaaggtagg gaggtgttcg | 540 |
| tacgggagca gcctcgggga cccctgcact gggtcagggc ttatgaagct agaagcgtcc | 600 |
| ctctgttccc tttgtgagtt ggtgggttgt tggtacattt ggttgaagc tgtgttgctg | 660 |
| gttagggaga ctcggttttg ctccttgggt tcgaggaaag ctggagaata aagccattg | 720 |
| tttgccgtct gtcggctttg tcgaccacgc tcacccctc ctgttcgtac tttttaaagc | 780 |
| agtgaggcga ggtagacagg gtgtgtcaca gtacagttaa aggggtgaag atctaaacgc | 840 |
| caaaagagaa gttaatcaca ataagtgagg tttgggataa aaagttgggc ttgccccttt | 900 |
| caaagtccca gaaagctggg aggtagatgg agaggggggcc attgggaagt ttttttggtg | 960 |
| tagggagagg agtagaagat aaagggtaag cagagtgtt | 999 |

<210> SEQ ID NO 13
<211> LENGTH: 1680
<212> TYPE: DNA
<213> ORGANISM: Homo sapiens

<400> SEQUENCE: 13

| | |
|---|---|
| cagactggga attgccgtgg ctatgcccga agtttggaaa gtctctctcg gtctctttct | 60 |
| gggacagcct ttcttttttcc gggaagcttc ctgtgcctag aggtggggct ctgtagctgg | 120 |
| aggggtagat ggaacttgcg aagcaaagga aggcaataaa aggaagttag gagaaaccgg | 180 |
| aaacgtgggc caggccttgc tctgttggag aagcggtgtc cccgcaaagt ccctgcttgc | 240 |
| gctggtcccg gccggagccc agatccccca aacgcctgtc acttctcatc gagttgaggc | 300 |
| tccggccccc acccgcgcct tggtgagggc ccccctcag ccccaagcct tcggctaccc | 360 |
| tgaaaacgcg gctcccctcg aaggggaaac aagtgcagtt caatctcgtc tgagtgatct | 420 |
| acaaataagg acggaaaggg tcgttttatc acggtcccgt tgtcgtgac gatgcaattt | 480 |
| cccggagcga agcactgtca caaagtgaca aggctgccac aagcgccccg actgatcttt | 540 |
| tcaattagcc ttccatgcat gatccggagc gacttccgcc tatttccaga aattaagctc | 600 |
| aaacttgacg tgcagctagt tttatttttaa agacaaatgt cagagaggct catcatattt | 660 |
| tccccctct tctatatttg gagcttattt attgctaaga agctcaggct cctggcgtca | 720 |
| atttatcagt aggctccaag gagaagagag gagaggagag gagagctgaa cagggagcca | 780 |
| cgtcttttcc tgggagggct gctatctaag tcggggctgc aggttggaga ttttttaagga | 840 |
| agtggaaatt ggcaattggc tttgtgtgtc tgtggttttt ggggaggggg actacaaaga | 900 |
| ggggctaact ccctctccct attctctaag gttggaccac agggatgagg ttgtgagata | 960 |
| caaagataaa ggagggatgg ggaacactat gatgtggtat ttttcttttc tgttttttct | 1020 |
| ttttgataat atctatcctt ggctaagggg agggcggagt tcagcggcgg aaataaagcg | 1080 |
| agcagtggct ggtgcgaacc gactcccggc tctaagcctt acttgcggtg gccggacttg | 1140 |
| tctgtggctg aagccgagcc cgggctctga ctctcacgtc tgcactggag gtgcggaaac | 1200 |
| ctggactggg gttcaccagc cacatactgg ctgctctggt tgttctctcc tcttccttct | 1260 |
| tctattctaa ccaaacaaaa cccaactcga tgcttgtgcc aggccttggc cagtttggac | 1320 |
| ggtgatggaa acatttctgg attttagcgt ctaagggagc actcaagggc tgtaaggttt | 1380 |
| gctatcactg tcccaacact gcagagacct tgaaggttca gtgtgggatc tgtagaaccc | 1440 |
| atggtttgcg gtgacactca gaggggatct ttggagagatt tatagagccg gttcttagcg | 1500 |
| ctttgtgggt tcagaggctg gctgcagtgt ttatgaagag gggcagtggg ctggggacac | 1560 |

```
tgctggggtt atggctgtag tgaggtccat gtgtacttgt tccttggcat gtgtctgact    1620
ctgtgttgct gctgcagtac agtgggcagg ggcacggttg cttggactgg gctgcccgat    1680
```

<210> SEQ ID NO 14
<211> LENGTH: 1622
<212> TYPE: DNA
<213> ORGANISM: Homo sapiens

<400> SEQUENCE: 14

```
ggacacatcg accacattgt atgtaggtgg tgtttgttga accattttgt tggcctggga      60
atgtgagggt tgtgtatgtc aggagcggta tgaaggtggc tggtgggtgc gtgtgtgtgt     120
ttgtgggcag cactgtgtgc ataagaacga gctgcgtggt gcactattca aatttgacat     180
tagaatgcag ggagagcccc cttgtagaag tgtgacaaga taacgcactg acagactgcg     240
aggttaacat aattgtatcc tgttgctttt tgctgtaatt gacaaattat gtgactatga     300
gtagggtgca catgaaaagg tgagcaggga gatgcagggc gagtcgggga tggggcattg     360
gaagtggtgg tctcccaact aaaaccaccc cactatcctt gcccctcccc cgttcgcccc     420
tctgggtccc actttctcac tctctgtggg tggcgactat gtggaagtgg tgaggtgaag     480
atactgtgag caggacggcg ggatgccggg agccgctctg gtctgggagg agagatggga     540
cctgaaacac cccaggttct gtgagaaggg ctggaggaag aagagcgggg gatgggggg     600
gtgggcgga gggagggtc agttggctcc cctccgctcc cctccacacc ccgaggtagc     660
ttggtcaaga ataggaaaca gtttactccg aagattaatc ggtatttgtt gtcctcgtga     720
caaggagata atatgcggga taatgggacg tggcgtctca ctcccaggag cacaacggag     780
ccgaggggct cggggccagg ggcggcgcgc gggactgcga ggaggctgcc ggcgcatccg     840
tgagctctcg gaccggctcc ggatgccggg cgcctccatg gagtcgggcg agggaaggga     900
aaatcggtaa cagtatgcga aatatctggt acaaggatg cttctgtcac tcgcaagaat     960
ttgttatggg aacaatcctg tcgctctgta attgctcatt agagaacgtt ttgtttctca    1020
ttaaggcgac atgaataagc gtctagttga aggagacagc tgtagaaatg ttccacaaga    1080
gacctctgga cacgattcgg caccaattgc caattagaca tgtcagtttt aagagcagaa    1140
aacaatatag gacggacact gggaagatag ggagcaaagc gctcgcttct tgtttcccag    1200
cgcggccgct cggccggcgg aggcctcctg acgcgcgggg cccgggctcc cctgggcgac    1260
cccgcccgca cgggccccga acccgccgcc tccgcgagct cagagggccc ccaggcccgc    1320
tcccgcctct ggtgagacta gcgattgacc ccaccgagtg taggcaaccc catccctgcc    1380
tgacttttga aaccgtagga ttcccacttg tagacactgg acacacccaa gtgacacccg    1440
aacttcgcac tcacgagcgt ccaccccctcc gcccccagca atctgaggtc ctggtgatcc    1500
ctcccctgac aagagtctgg cccacttagt ccgagaagtc ttggggaggg actcagggca    1560
cggtggccta ggcctgggag ggctgagccc agagcctcca ctccgggctc tccccggtgc    1620
gt                                                                    1622
```

<210> SEQ ID NO 15
<211> LENGTH: 1595
<212> TYPE: DNA
<213> ORGANISM: Homo sapiens

<400> SEQUENCE: 15

```
tgagtaactt agttatgaat aaataaatag tgcaatgtaa aaatattaga ccctaagttc      60
```

-continued

```
aatttataaa atgaagattt ttatataaaa attacggtca aggtgtcata tttaattat      120 atttctcaaa gaaagatgat tcatttgata taactaatta taagtttcat atcctacgtg     180
ttgatgacca cacagaaact ttaagacata taatagccaa atatgaatct actcttcctt     240
gccaaatgaa gcaatgatgt tctgccagcc aaactaacag gaagcatgtg aaatgaacac     300
agaagcaaac aggacttaca ctgcctaagg gaaagtcagc aagatggcag tttcaatcat     360
ttggaataat actaaagcag ccttaggctt ttctcagaat ggaaacatgt cactattact     420
gcaatatttc aacaaatcag aatgcagaga aaagaacact tatgcaacca catcttggaa     480
gggcacttta ctcaacattt aagtggaaaa caattataaa gaaatttcag aaaaactgtc     540
agtgaacata aatgactcag ggaaaaatgt ttttctttcc aaagtgctta atagatttt      600 caaaagctta ccacttagaa acaatttcct tatatattct ccttaaggaa ttattaatat     660
aaagacaaat ttatataaag aggtaagtga aaagtttgat attcaggttg ccggtaagaa     720
atgctcattt ttccccagta cagtactatt actttggaag gtttgatcaa agggaataag    780
ctttcacaac atttatatag gaagttaaaa aatacttcaa atattttggg aacttaccta    840
atcaggatac ttttagcatg tgtctagtca tgtagccatc tttggtcaat catcaaaaaa    900 tcaagggaa attggcatga ctcaacccta actttaatac cgcatgattg tgtcgtgtaa     960
gcttgttttg tgtgagagct gctgtggttt tagcagagag attaacaacc ggacctaagc    1020
tggcctccaa accttgccct gctgatgcct caagctcttt gaagtctgac catcatacct    1080
ggcaaaacaa cagtgggaac taggatggtg tcagatctaa tcaaattgtt gctgcagca     1140 tagctaacta tggggttcac taattggccc aattgcggat tatacctttt gctacagatt    1200
caagacaata atttagttaa atgatgtttt ttttttttctt atctcttcta attaagattc    1260
caaagtggga agaaatagga ttagacagat tctcaaaact gtgttctcct taaggtggta    1320 tgcactttg ataggttaac tatggcatgt gaaatatata aagtgtagta agtattaaac     1380
caacttctga tgattctttg aaacctatgt aatgctatta tatgctgata tcacttgaga    1440
ataaaagcat aaacatgaga atgataatat aatgaatata tcaaaatgta cacatgtaaa    1500
aaattagatt tccattgtta aaaaatgtta atttgggttt attttttgaca actgatttaa   1560 tctaaatgaa tagatgccta tgttcaactt tgatt                               1595
```

<210> SEQ ID NO 16
<211> LENGTH: 1644
<212> TYPE: DNA
<213> ORGANISM: Homo sapiens

<400> SEQUENCE: 16

```
ttaataaatg tcacattttg ccagatcaaa acaataggtt aatatgttta taaacatagt      60
atgtccagtt attaagtagc aaaagttcta aaatactaag aatctcctgg ctataagaat     120
ataatcatca aatatctggt agggtttttt tttttaattc tttaattact ggaaatctag     180
tattcctttt agcccctgac agggtggtag attagaaaac tgtgattata tgctatgatg     240
tcttagacaa ttttttgctt ggcagatcta gataagctga aaatgttttt tgtaaaattt     300
tgcaattttg aaactctcat tttatacaat ggtaatgccc accagtttaa aactaatctt     360
tgaagaagag aatgggaaat ataaaacagt caagaaaatt tatcagcctg ctatatcccc    420
tgttagaaag aggtcaaata taataaaaga ttttcatttt ctgggaacat gattacaact     480
gagcttacta atattcttgt ttcttaagtc ccctttataaa gatggcctaa gaatgaaaaa    540
ttaaagaggg ctggtcaatg ttacctgact tggtattatg aaacacatag tagcctgtgt     600
```

```
caccaaacat tctgttgaaa tgactggtta actcacacct agagcagtat ttgaaactcc      660
ttcataagtt ggaatgtgtg ttatataaag aatgtttcag cattatacaa ggaatgtttc      720
agcctttgga tcagtgttgt taaaaagaat cagtaaaaat aattattctt aattgtcttt      780
aatatgttca atcacgtggg cacactaagt atagaaaaac atagtttgga aatgcctatt      840
ttttctaagg caatttttca ttcaatggtg agaaaataat ccagattgat tccttacttt      900
cagttctgtg ccacagggga tggtcctact ccaggaataa caggggcttc agaggccata      960
aacatgttcc tctcaatatt tctttagcca aagaccatta tatcaaactc atccaggttg     1020
ggtttcagcc agttattctt cacccaaaca aaaatgtctg ccagacattc aacagctgg      1080 gatacagttc acaatgagtc aacttgaaaa tgattcattg tgctgagtac tgaacaatgt     1140
tggggtgggg gtggggtgtg gctgggttgg tagtaaaggg tgagaacaag tgggagatga     1200
agaataacca tgtggctccc ccattaagaa gaatcatgga taataaccag caggctctta     1260
tcatttcatt tttaggataa actcaactgg gaagagtact cctgtcatgg accctcagat     1320
gaacaagcat ttataaaggc tactgacaat atttcttaat caaaaggtca gatttccttt     1380
tatctataaa taaagactaa agccttttta tctaaatatc tgaaactaaa atgatacaag     1440 tcaattttg ttagaactca tctattcaag atttcagtga tataaactag gactttctca     1500
attatatgaa taacagaaat tgcaaggttt aaagatgaga taaatttcca ttctgatagt     1560
acataagcaa agtactgtgt atttaaatgg tcaacctgac atttgcttat ttcaaagagg     1620
atttacttct ttcatttaat ctta                                            1644

<210> SEQ ID NO 17
<211> LENGTH: 1269
<212> TYPE: DNA
<213> ORGANISM: Homo sapiens

<400> SEQUENCE: 17
atgcagaaca gtcacagcgg agtgaatcag ctcggtggtg tctttgtcaa cgggcggcca       60
ctgccggact ccacccggca gaagattgta gagctagctc acagcggggc ccggccgtgc      120
gacatttccc gaattctgca ggtgtccaac ggatgtgtga gtaaaattct gggcaggtat      180
tacgagactg gctccatcag acccagggca atcggtggta gtaaaccgag agtagcgact      240
ccagaagttg taagcaaaat agcccagtat aagcgggagt gcccgtccat ctttgcttgg      300
gaaatccgag acagattact gtccgagggg gtctgtacca acgataacat accaagcgtg      360
tcatcaataa acagagttct tcgcaacctg gctagcgaaa agcaacagat gggcgcagac      420
ggcatgtatg ataaactaag gatgttgaac gggcagaccg gaagctgggg cacccgccct      480
ggttggtatc cggggacttc ggtgccaggg caacctacgc aagatggctg ccagcaacag      540
gaaggagggg gagagaatac caactccatc agttccaacg agaagattc agatgaggct      600 caaatgcgac ttcagctgaa gcggaagctg caaagaaata aacatccctt acccaagag      660 caaattgagg ccctggagaa agagtttgag agaacccatt atccagatgt gtttgcccga      720
gaaagactag cagccaaaat agatctacct gaagcaagaa tacaggtatg gttttctaat      780
cgaagggcca aatggagaag agaagaaaaa ctgaggaatc agagaagaca ggccagcaac      840
acacctagtc atattcctat cagcagtagt ttcagcacca gtgtctacca accaattcca      900
caacccacca caccggtttc ctccttcaca tctggctcca tgttgggccg aacagacaca      960
gccctcacaa acacctacag cgctctgccg cctatgccca gcttcaccat ggcaaataac     1020
```

```
ctgcctatgc aaccccccagt ccccagccag acctcctcat actcctgcat gctgcccacc      1080
agcccttcgg tgaatgggcg gagttatgat acctacaccc ccccacatat gcagacacac      1140
atgaacagtc agccaatggg cacctcgggc accacttcaa caggactcat ttcccctggt      1200
gtgtcagttc cagttcaagt tcccggaagt gaacctgata tgtctcaata ctggccaaga      1260
ttacagtaa                                                              1269

<210> SEQ ID NO 18
<211> LENGTH: 3662
<212> TYPE: DNA
<213> ORGANISM: Homo sapiens

<400> SEQUENCE: 18
cagactggga attgccgtgg ctatgcccga gtttggaaaa gtctctctcg gtctctttct        60
gggacagcct ttcttttttcc gggaagcttc ctgtgcctag aggtggggct ctgtagctgg       120
aggggtagat ggaacttgcg aagcaaagga aggcaataaa aggaagttag gagaaaccgg       180
aaacgtgggc caggccttgc tctgttggag aagcggtgtc cccgcaaagt ccctgcttgc       240
gctggtcccg gccggagccc agatccccca aacgcctgtc acttctcatc gagttgaggc       300
tccggccccc acccgcgcct tggtgagggc ccccccctcag ccccaagcct tcggctaccc       360
tgaaaacgcg gctcccctcg aaggggaaac aagtgcagtt caatctcgtc tgagtgatct       420
acaaataagg acgaaagggg tcgttttatc acggtcccgt ttgtcgtgac gatgcaattt       480
cccggagcgg agcactgtca caaagtgaca aggctgccac aagcgccccg actgatcttt       540
tcaattagcc ttccatgcat gatccggagc gacttccgcc tatttccaga aattaagctc       600
aaacttgacg tgcagctagt tttattttaa agacaaatgt cagagaggct catcatattt       660 tccccccctct tctatatttg gagcttattt attgctaaga agctcaggct cctggcgtca       720
atttatcagt aggctccaag gagaagagag gagaggagag gagagctgaa cagggagcca       780
cgtcttttcc tgggagggct gctatctaag tcggggctgc aggttggaga ttttttaagga       840 agtggaaatt ggcaattggc tttgtgtgtc tgtggttttt ggggagggggg actacaaaga       900 ggggctaact ccctctcccct attctctaag gttggaccac agggatgagg ttgtgagata       960
caaagataaa ggagggatgg ggaacactat gatgtggtat ttttcttttc tgttttttct      1020
ttttgataat atctatcctt ggctaagggg agggcggagt tcagcggcgg aaataaagcg      1080
agcagtggct ggtgcgaacc gactcccggc tctaagcctt acttgcggtg gccggacttg      1140
tctgtggctg aagccgagcc cgggctctga ctctcacgtc tgcactggag gtgcggaaac      1200
ctggactggg gttcaccagc cacatactgg ctgctctggt tgttctctcc tcttccttct      1260
tctattctaa ccaaacaaaa cccaactcga tgcttgtgcc aggccttggc cagtttggac      1320
ggtgatggaa acatttctgg attttagcgt ctaagggagc actcaagggc tgtaaggttt      1380
gctatcactg tcccaacact gcagagacct tgaaggttca gtgtgggatc tgtagaaccc      1440
atggtttgcg gtgacactca gagggggatct ttgggagatt tatagagccg gttcttagcg      1500
ctttgtgggt tcagaggctg gctgcagtgt ttatgaagag gggcagtggg ctggggacac      1560
tgctggggtt atggctgtag tgaggtccat gtgtacttgt tccttggcat gtgtctgact      1620
ctgtgttgct gctgcagtac agtgggcagg ggcacggttg cttggactgg gctgcccgat      1680
cttggggatc ggaggagggg acagggtgat tacccagaga ggtagctggc cagcctaagg      1740
gcagagatct tggggcccta gtgcccgaag gtgcggagga gcgcactcgg caagactagt      1800
ttcctgggga tcgactctac gccatacagg acggcggccc aggctggacc gggccgggct      1860
```

```
agagcagtca caggccgggc caaggaaggc caaagcaggg gttggagccg gccggaccct      1920
gggtggggag aagcaggctc ccgcccggcc ggaaaactag tcggcgcaga gctgtgccca      1980
actctagccg ccatgacgtc acgcgggccg ggcagccaat gaggacggcg ctggcgtgga      2040
tattaaggaa agttagcgcc tgcctgagca ccctctttc ttatcattga catttaaact       2100
ctggggcagg tcctcgcgta gaacgcggct gtcaggcgcg ccgaagttgg tcgtgaggca      2160
ctgggcaggt aagtatcaag gttacaagac aggtttaagg agaccaatag aaactgggct      2220
tgtcgagaca gagaagactc ttgcgtttct gataggcacc tattggtctt actgacatcc      2280
actttgcctt tctctccaca ggtgtccact cccaggcggc cgccaccatg gactacaaag      2340
accatgacgg tgattataaa gatcatgaca tcgattacaa ggatgacgat gacaagcaga      2400
acagtcacag cggagtgaat cagctcgtg gtgtctttgt caacgggcgg ccactgccgg       2460
actccacccg gcagaagatt gtagagctag ctcacagcgg ggcccggccg tgcgacattt      2520
cccgaattct gcaggtgtcc aacgatgtg tgagtaaaat tctgggcagg tattacgaga       2580
ctggctccat cagacccagg gcaatcggtg gtagtaaacc gagagtagcg actccagaag      2640
ttgtaagcaa aatagcccag tataagcggg agtgcccgtc catctttgct tgggaaatcc      2700
gagacagatt actgtccgag ggggtctgta ccaacgataa cataccaagc gtgtcatcaa      2760
taaacagagt tcttcgcaac ctggctagcg aaaagcaaca gatgggcgca gacggcatgt      2820
atgataaact aaggatgttg aacgggcaga ccggaagctg gggcacccgc cctggttggt      2880
atccggggac ttcggtgcca gggcaaccta cgcaagatgg ctgccagcaa caggaaggag      2940
ggggagagaa taccaactcc atcagttcca acggagaaga ttcagatgag gctcaaatgc      3000
gacttcagct gaagcggaag ctgcaaagaa atagaacatc ctttacccaa gagcaaattg      3060
aggccctgga gaaagagttt gagagaaccc attatccaga tgtgtttgcc cgagaaagac      3120
tagcagccaa aatagatcta cctgaagcaa gaatacaggt atggtttttct aatcgaaggg      3180 ccaaatggag aagagaagaa aaactgagga atcagagaag acaggccagc aacacaccta      3240
gtcatattcc tatcagcagt agtttcagca ccagtgtcta ccaaccaatt ccacaaccca      3300
ccacaccggt ttcctccttc acatctggct ccatgttggg ccgaacagac acagccctca      3360
caaacaccta cagcgctctg ccgcctatgc ccagcttcac catggcaaat aacctgccta      3420
tgcaaccccc agtccccagc cagacctcct catactcctg catgctgccc accagccctt      3480
cggtgaatgg gcggagttat gatacctaca cccccccaca tatgcagaca cacatgaaca      3540
gtcagccaat gggcacctcg ggcaccactt caacaggact catttcccct ggtgtgtcag      3600
ttccagttca agttcccgga agtgaacctg atatgtctca atactggcca agattacagt      3660
aa                                                                    3662

<210> SEQ ID NO 19
<211> LENGTH: 3577
<212> TYPE: DNA
<213> ORGANISM: Homo sapiens

<400> SEQUENCE: 19
tgagtaactt agttatgaat aaataaatag tgcaatgtaa aaatattaga ccctaagttc        60
aatttataaa atgaagattt ttatataaaa attacggtca aggtgtcata ttttaattat       120
atttctcaaa gaaagatgat tcatttgata taactaatta taagtttcat atcctacgtg       180
ttgatgacca cacagaaact ttaagacata taatagccaa atatgaatct actcttcctt       240
```

```
gccaaatgaa gcaatgatgt tctgccagcc aaactaacag gaagcatgtg aaatgaacac     300
agaagcaaac aggacttaca ctgcctaagg gaaagtcagc aagatggcag tttcaatcat     360
ttggaataat actaaagcag ccttaggctt ttctcagaat ggaaacatgt cactattact     420
gcaatatttc aacaaatcag aatgcagaga aagaacact tatgcaacca catcttggaa      480
gggcacttta ctcaacattt aagtggaaaa caattataaa gaaatttcag aaaaactgtc     540
agtgaacata aatgactcag ggaaaaatgt tttttcttcc aaagtgctta atagattttt     600
caaaagctta ccacttagaa acaatttcct tatatattct ccttaaggaa ttattaatat     660
aaagacaaat ttatataaag aggtaagtga aagtttgat attcaggttg ccggtaagaa      720
atgctcattt ttccccagta cagtactatt actttggaag gtttgatcaa agggaataag     780
ctttcacaac atttatatag gaagttaaaa aatacttcaa atattttggg aacttaccta    840
atcaggatac ttttagcatg tgtctagtca tgtagccatc tttggtcaat catcaaaaaa    900
tcaaagggaa attggcatga ctcaacccta actttaatac cgcatgattg tgtcgtgtaa    960
gcttgttttg tgtgagagct gctgtggttt tagcagagag attaacaacc ggacctaagc   1020
tggcctccaa accttgccct gctgatgcct caagctcttt gaagtctgac catcatacct   1080
ggcaaaacaa cagtgggaac taggatggtg tcagatctaa tcaaattgtt tgctgcagca   1140
tagctaacta tggggttcac taattggccc aattgcggat tatacctttt gctacagatt   1200
caagacaata atttagttaa atgatgtttt tttttttctt atctcttcta attaagattc   1260
caaagtggga agaaatagga ttagacagat tctcaaaact gtgttctcct taaggtggta   1320 tgcactttg ataggttaac tatggcatgt gaaatatata aagtgtagta agtattaaac    1380
caacttctga tgattctttg aaacctatgt aatgctatta tatgctgata tcacttgaga   1440
ataaaagcat aaacatgaga atgataatat aatgaatata tcaaaatgta cacatgtaaa   1500
aaattagatt tccattgtta aaaaatgtta atttgggttt attttttgaca actgatttaa   1560 tctaaatgaa tagatgccta tgttcaactt tgattcttgg ggatcggagg aggggacagg    1620
gtgattaccc agagaggtag ctggccagcc taagggcaga gatcttgggg ccctagtgcc    1680
cgaaggtgcg gaggagcgca ctcggcaaga ctagtttcct ggggatcgac tctacgccat    1740
acaggacggc ggcccaggct ggaccgggcc gggctagagc agtcacaggc cgggccaagg    1800
aaggccaaag cagggggttgg agccggccgg accctgggtg gggagaagca ggctcccgcc   1860
cggccggaaa actagtcggc gcagagctgt gcccaactct agccgccatg acgtcacgcg    1920
ggccgggcag ccaatgagga cggcgctggc gtggatatta aggaaagtta gcgcctgcct    1980
gagcaccctc tttcttatc attgacattt aaactctggg gcaggtcctc gcgtagaacg     2040
cggctgtcag gcgcgccgaa gttggtcgtg aggcactggg caggtaagta tcaaggttac    2100
aagacaggtt taaggagacc aatagaaact gggcttgtcg agacagagaa gactcttgcg    2160
tttctgatag gcacctattg gtcttactga catccacttt gcctttctct ccacaggtgt    2220
ccactcccag gcggccgcca ccatggacta caaagaccat gacggtgatt ataaagatca    2280
tgacatcgat tacaaggatg acgatgacaa gcagaacagt cacagcggag tgaatcagct    2340
cggtggtgtc tttgtcaacg ggcggccact gccggactcc acccggcaga agattgtaga    2400
gctagctcac agcggggccc ggcgtgcga catttcccga attctgcagg tgtccaacgg     2460
atgtgtgagt aaaattctgg gcaggtatta cgagactggc tccatcagac ccagggcaat    2520
cggtggtagt aaaccgagag tagcgactcc agaagttgta agcaaaatag cccagtataa    2580
gcgggagtgc ccgtccatct ttgcttggga aatccgagac agattactgt ccgaggggt     2640
```

```
ctgtaccaac gataacatac caagcgtgtc atcaataaac agagttcttc gcaacctggc      2700
tagcgaaaag caacagatgg gcgcagacgg catgtatgat aaactaagga tgttgaacgg      2760
gcagaccgga agctggggca cccgccctgg ttggtatccg gggacttcgg tgccagggca      2820
acctacgcaa gatggctgcc agcaacagga aggaggggga gagaatacca actccatcag      2880
ttccaacgga gaagattcag atgaggctca aatgcgactt cagctgaagc ggaagctgca      2940
aagaaataga acatccttta cccaagagca aattgaggcc ctggagaaag agtttgagag      3000
aacccattat ccagatgtgt tgcccgaga aagactagca gccaaaatag atctacctga      3060
agcaagaata caggtatggt tttctaatcg aagggccaaa tggagaagag aagaaaaact      3120
gaggaatcag agaagacagg ccagcaacac acctagtcat attcctatca gcagtagttt      3180
cagcaccagt gtctaccaac caattccaca acccaccaca ccggtttcct ccttcacatc      3240
tggctccatg ttgggccgaa cagacacagc cctcacaaac acctacagcg ctctgccgcc      3300
tatgcccagc ttcaccatgg caaataaacct gcctatgcaa cccccagtcc ccagccagac      3360
ctcctcatac tcctgcatgc tgcccaccag cccttcggtg aatgggcgga gttatgatac      3420
ctacaccccc ccacatatgc agacacacat gaacagtcag ccaatgggca cctcgggcac      3480
cacttcaaca ggactcattt cccctggtgt gtcagttcca gttcaagttc ccggaagtga      3540
acctgatatg tctcaatact ggccaagatt acagtaa                              3577

<210> SEQ ID NO 20
<211> LENGTH: 3615
<212> TYPE: DNA
<213> ORGANISM: Homo sapiens

<400> SEQUENCE: 20
gggtgccggg actgagagac aggaaggaag cattggagag ccaacctaga taagggtaac        60
tagtaaccct ctgctgtggc cagtatttac ccaatgctga gaaaaagtcc tcattttcgg       120 tttatttta tggatttaag ctgtctacca agtagttaaa aagtagacca ggaatggcct       180
tgtagagtaa aatgtgcttc ttgaaattct ttgcttgcag gcaggcagat caataatcac       240
cataggtaaa acagaaaaaa taatgcattt aaaaaaaaac agagagaaat gatgctgtga       300
ctgttttgtt attttacctc tttttggggg gcagacctct tgaatgggct ctttattgta       360
actctctctt cccaattgag ctccccacgg tgccgttgta tcttttttaca gcccctaaca       420 actcacacca gtaacacaat tacctccaga tatttacaac aagaaattac ttttctattt       480
tctccactca cccaaaagac ttttttttttt tttcctttgg gaaaggtagg gaggtgttcg       540
tacgggagca gcctcgggga cccctgcact gggtcagggc ttatgaagct agaagcgtcc       600
ctctgttccc tttgtgagtt ggtggttgt tggtacattt ggttggaagc tgtgttgctg       660
gttagggaga ctcggttttg ctccttgggt tcgaggaaag ctggagaata gaagccattg       720
tttgccgtct gtcggctttg tcgaccacgc tcacccccctc ctgttcgtac ttttttaaagc       780 agtgaggcga ggtagacagg gtgtgtcaca gtacagttaa agggtgaag atctaaacgc       840 caaaagagaa gttaatcaca ataagtgagg tttgggataa aaagttgggc ttgccccttt       900
caaagtccca gaaagctggg aggtagatgg agaggggggcc attgggaagt ttttttggtg       960
tagggagagg agtagaagat aaagggtaag cagagtgttc ctgcgttcta gacagaaaag      1020 cccccttctga ccatgcatta gtagtactac tccattattc ctgttagaac aagttaaaag      1080
taagggttga gcccaaaggc cccaggaggg gggtcatgtg cgccccagtc actcaggctc      1140
```

```
ccctcgcttc tccggttcga gttatgccat caagctaata tattgtgact gctcttctct    1200
cctgtgacaa aggcttgcag ctgcctccaa atcaatagat gtcaaagaaa tatgaaaaca    1260
atcatgacac aaaacttaaa tcctggctgg agcctacata atcagaaatg tgctactgtt    1320
cttcaagcca ccgattaatt tatcccaaac tttagtcaaa ttttttattcc ggtacctttt    1380 tcccagcaga tcctgctacg tctgtcgggt ttgtaatgta atttgtaatt actgcccttc    1440
atgtggtccg gtgccttgaa ccatctttaa ttaaaagcat aattaaggga agatctaaag    1500
aaagacaatt accagatggt cttttttta gaggcggtag ttgcgcagag aggggctcgg    1560
ggtctgtccc cgggaccccca cgccttggga ggggcggcg ggcccgaacg gcgcctgcgc    1620
actgaggagg cctcttgggg atcggaggag gggacagggt gattacccag agaggtagct    1680
ggccagccta agggcagaga tcttggggcc ctagtgcccg aaggtgcgga ggagcgcact    1740
cggcaagact agtttcctgg ggatcgactc tacgccatac aggacggcgg cccaggctgg    1800
accgggccgg gctagagcag tcacaggccg ggccaaggaa ggccaaagca ggggttggag    1860
ccggccggac cctgggtggg gagaagcagg ctcccgcccg gccggaaaac tagtcggcgc    1920
agagctgtgc ccaactctag ccgccatgac gtcacgcggg ccgggcagcc aatgaggacg    1980
gcgctggcgt ggatattaag gaaagttagc gcctgcctga gcaccctctt ttcttatcat    2040
tgacatttaa actctggggc aggtcctcgc gtagaacgcg gctgtcaggc gcgccgaagt    2100
tggtcgtgag gcactgggca ggtaagtatc aaggttacaa gacaggttta aggagaccaa    2160
tagaaactgg gcttgtcgag acagagaaga ctcttgcgtt tctgataggc acctattggt    2220
cttactgaca tccactttgc ctttctctcc acaggtgtcc actcccaggc ggccgccacc    2280
atggactaca aagaccatga cggtgattat aaagatcatg acatcgatta caaggatgac    2340
gatgacaaga gaacagtca cagcggagtg aatcagctcg gtggtgtctt tgtcaacggg    2400
cggccactgc cggactccac ccggcagaag attgtagagc tagctcacag cggggcccgg    2460
ccgtgcgaca tttcccgaat tctgcaggtg tccaacggat gtgtgagtaa aattctgggc    2520
aggtattacg agactggctc catcagaccc agggcaatcg gtggtagtaa accgagagta    2580
gcgactccag aagttgtaag caaaatagcc cagtataagc gggagtgccc gtccatcttt    2640
gcttgggaaa tccgagacag attactgtcc gagggggtct gtaccaacga taacatacca    2700
agcgtgtcat caataaacag agttcttcgc aacctggcta gcgaaaagca acagatgggc    2760
gcagacggca tgtatgataa actaaggatg ttgaacgggc agaccggaag ctggggcacc    2820
cgccctggtt ggtatccggg gacttcggtg ccagggcaac ctacgcaaga tggctgccag    2880
caacaggaag gaggggagag aataccaac tccatcagtt ccaacggaga agattcagat    2940
gaggctcaaa tgcgacttca gctgaagcgg aagctgcaaa gaaatagaac atcctttacc    3000
caagagcaaa ttgaggccct ggagaaagag tttgagagaa cccattatcc agatgtgttt    3060
gcccgagaaa gactagcagc caaaatagat ctacctgaag caagaataca ggtatggttt    3120
tctaatcgaa gggccaaatg gagaagagaa gaaaaactga ggaatcagag aagacaggcc    3180
agcaacacac ctagtcatat tcctatcagc agtagtttca gcaccagtgt ctaccaacca    3240 attcacaac ccaccacacc ggtttcctcc ttcacatctg gctccatgtt gggccgaaca    3300
gacacagccc tcacaaacac ctacagcgct ctgccgccta tgcccagctt caccatggca    3360
aataacctgc ctatgcaacc cccagtcccc agccagacct cctcatactc ctgcatgctg    3420
cccaccagcc cttcggtgaa tgggcggagt tatgataacc acaccccccc acatatgcag    3480
acacacatga acagtcagcc aatgggcacc tcgggcacca cttcaacagg actcatttcc    3540
```

```
cctggtgtgt cagttccagt tcaagttccc ggaagtgaac ctgatatgtc tcaatactgg    3600
ccaagattac agtaa                                                     3615

<210> SEQ ID NO 21
<211> LENGTH: 3661
<212> TYPE: DNA
<213> ORGANISM: Homo sapiens

<400> SEQUENCE: 21
cagactggga attgccgtgg ctatgcccga agtttggaaa gtctctctcg gtctctttct      60
gggacagcct ttcttttttcc gggaagcttc ctgtgcctag aggtggggct ctgtagctgg    120
aggggtagat ggaacttgcg aagcaaagga aggcaataaa aggaagttag gagaaaccgg    180
aaacgtgggc caggccttgc tctgttggag aagcggtgtc cccgcaaagt ccctgcttgc    240
gctggtcccg gccggagccc agatccccca aacgcctgtc acttctcatc gagttgaggc    300
tccggccccc acccgcgcct tggtgagggc cccccctcag ccccaagcct tcggctaccc    360
tgaaaacgcg gctcccctcg aaggggaaac aagtgcagtt caatctcgtc tgagtgatct    420
acaaataagg acggaaaggg tcgttttatc acggtcccgt ttgtcgtgac gatgcaattt    480
cccggagcgg agcactgtca caaagtgaca aggctgccac aagcgccccg actgatcttt    540
tcaattagcc ttccatgcat gatccggagc gacttccgcc tatttccaga aattaagctc    600
aaacttgacg tgcagctagt tttattttaa agacaaatgt cagagaggct catcatattt    660
tcccccctct tctatatttg gagcttattt attgctaaga agctcaggct cctggcgtca    720
atttatcagt aggctccaag gagaagagag gagaggagag gagagctgaa cagggagcca    780
cgtcttttcc tgggagggct gctatctaag tcgggctgc aggttggaga ttttttaagga    840 agtggaaatt ggcaattggc tttgtgtgtc tgtggttttt ggggaggggg actacaaaga    900
ggggctaact ccctctccct attctctaag gttggaccac agggatgagg ttgtgagata    960
caaagataaa ggagggatgg ggaacactat gatgtggtat ttttcttttc tgttttttct   1020
ttttgataat atctatcctt ggctaagggg agggcggagt tcagcggcgg aaataaagcg   1080
agcagtggct ggtgcgaacc gactcccggc tctaagcctt acttgcggtg gccggacttg   1140
tctgtggctg aagccgagcc cgggctctga ctctcacgtc tgcactggag gtgcggaaac   1200
ctggactggg gttcaccagc cacatactgg ctgctctggt tgttctctcc tcttccttct   1260
tctattctaa ccaaacaaaa cccaactcga tgcttgtgcc aggccttggc cagtttggac   1320
ggtgatggaa acatttctgg attttagcgt ctaagggagc actcaagggc tgtaaggttt   1380
gctatcactg tcccaacact gcagagacct tgaaggttca gtgtgggatc tgtagaaccc   1440
atggtttgcg gtgacactca gagggatct ttgggagatt tatagagccg gttcttagcg   1500
ctttgtgggt tcagaggctg gctgcagtgt ttatgaagag gggcagtggg ctggggacac   1560
tgctggggtt atggctgtag tgaggtccat gtgtacttgt tccttggcat gtgtctgact   1620
ctgtgttgct gctgcagtac agtgggcagg gcacggttg cttggactgg gctgcccgat   1680
caccctccga ggactgggag tcccgagtcc agcttagggg gagtgggggc gcgaccccca   1740
acccagaaac cttcacttga ccgctcaagt tcgcggcagc agggcgggcc gcgccgaatc   1800
tcggcgtgcg cggagcgggg agatgcaggc gagcgccaga gcccgggctc gggggccctg   1860
cgccggggag aggagccggg acccaccggc ggagccgaaa acaagtgtat tcatattcaa   1920
acaaacggac caattgcacc aggcggggag agggagcatc caatcggctg gcgcgaggcc   1980
```

```
ccggcgctgc tttgcataaa gcaatatttt gtgtgagagc gagcggtgca tttgcatgtt    2040
gcggagtgat tagtgggttt gaaaagggaa ccgtggctcg gcctcatttc ccgctctggt    2100
tcaggcgcag gaggaagtgt tttgctggag gatggcgcgc cgaagttggt cgtgaggcac    2160
tgggcaggta agtatcaagg ttacaagaca ggtttaagga gaccaataga aactgggctt    2220
gtcgagacag agaagactct tgcgtttctg ataggcacct attggtctta ctgacatcca    2280
ctttgccttt ctctccacag gtgtccactc ccaggcggcc gccaccatgg actacaaaga    2340
ccatgacggt gattataaag atcatgacat cgattacaag gatgacgatg acaagcagaa    2400
cagtcacagc ggagtgaatc agctcggtgg tgtctttgtc aacggcggc cactgccgga     2460 ctccacccgg cagaagattg tagagctagc tcacagcggg gcccggccgt gcgacatttc    2520
ccgaattctg caggtgtcca acggatgtgt gagtaaaatt ctgggcaggt attacgagac    2580
tggctccatc agacccaggg caatcggtgg tagtaaaccg agagtagcga ctccagaagt    2640
tgtaagcaaa atagcccagt ataagcggga gtgcccgtcc atctttgctt gggaaatccg    2700
agacagatta ctgtccgagg gggtctgtac caacgataac ataccaagcg tgtcatcaat    2760
aaacagagtt cttcgcaacc tggctagcga aaagcaacag atgggcgcag acggcatgta    2820
tgataaacta aggatgttga acgggcagac cggaagctgg ggcacccgcc ctggttggta    2880 tccgggggact tcggtgccag ggcaacctac gcaagatggc tgccagcaac aggaaggagg    2940
gggagagaat accaactcca tcagttccaa cggagaagat tcagatgagg ctcaaatgcg    3000
acttcagctg aagcggaagc tgcaaagaaa tagaacatcc tttacccaag agcaaattga    3060
ggccctggag aaaagagtttg agagaaccca ttatccagat gtgtttgccc gagaaagact    3120
agcagccaaa atagatctac ctgaagcaag aatacaggta tggttttcta atcgaagggc    3180
caaatggaga agagaagaaa aactgaggaa tcagagaaga caggccagca acacacctag    3240
tcatattcct atcagcagta gtttcagcac cagtgtctac caaccaattc cacaacccac    3300 cacccggtt tcctccttca catctggctc catgttgggc cgaacagaca cagccctcac    3360
aaacacctac agcgctctgc cgcctatgcc cagcttcacc atggcaaata acctgcctat    3420
gcaaccccca gtccccagcc agacctcctc atactcctgc atgctgccca ccagcccttc    3480
ggtgaatggg cggagttatg atacctacac cccccacat atgcagacac acatgaacag    3540
tcagccaatg ggcacctcgg gcaccacttc aacaggactc atttcccctg gtgtgtcagt    3600
tccagttcaa gttcccggaa gtgaacctga tatgtctcaa tactggccaa gattacagta    3660
a                                                                   3661
```

PAX6 MINIPROMOTERS

CROSS REFERENCE

This application claims benefit of U.S. Provisional Patent Application No. 62/286,988, filed Jan. 26, 2016, which application is incorporated herein by reference in its entirety.

FIELD

The invention relates to gene promoters and regulatory elements. More specifically, the invention relates to novel PAX6 promoter compositions and related methods.

BACKGROUND

Gene therapy for ocular disorders is reaching the clinic, with long-term trials of gene therapies for Leber's congenital amaurosis reporting improvements in patients (Bainbridge, Mehat et al. 2015; Jacobson, Cideciyan et al. 2015). Promoters such as the chicken beta actin and cytomegalovirus are common in current gene therapies, particularly because they are strong, small, and well characterized. However, in applications where restricted expression is desired, such as targeting transcription to a specific tissue or limiting it to particular cells, a toolbox of specific promoters would be advantageous. Previously, we have developed mini-promoters (approximately four kb human regulatory sequences for tissue and cell-specific expression), using bioinformatics, and single copy knock-into the mouse genome (Portales-Casamar, Swanson et al. 2010; de Leeuw, Dyka et al. 2014). Building on, and further refining these techniques, we are expanding the current toolbox by introducing new mini-promoters from PAX6 (paired box 6 (OMIM: 607108)).

Although PAX6 is expressed in a variety of tissues including the CNS, pancreas, and small intestine, it is best known as the essential transcription factor for panocular development in species as diverse as flies (*Drosophila melanogaster*), mice (*Mus musculus*), and humans, see Cvekl et al. 2016 for a review (Cvekl and Callaerts 2016). In humans, loss-of-function mutations produce the ocular disorder aniridia (OMIM: 106210). Current interventions can delay blindness due to aniridia, but new therapies are needed to safe guard or even restore patient vision, and gene therapy is one promising therapeutic approach.

One challenge for PAX6 gene therapy is that transcription of the endogenous gene is complex, and inappropriate PAX6 could be detrimental. Ectopic expression of PAX6 orthologues in *D. melanogaster* and *Xenopus laevis* resulted in the formation of ectopic eyes (Halder, Callaerts et al. 1995; Chow, Altmann et al. 1999). Furthermore, overexpression of PAX6 in mice interfered with ocular development resulting in microphthalmia (Schedl, Ross et al. 1996; Manuel, Pratt et al. 2008). Finally, expression is temporally regulated with, for example, broad and robust developmental expression being restricted to ganglion, amacrine, horizontal, and Müller glia cells in the adult retina. At least 39 cis-regulatory elements have been verified in vivo, see Cvekl et al. 2016 for a review (Cvekl and Callaerts 2016). Of these elements, those with known adult expression, and those amenable to "cut down" are of greatest interest, as they would be suited for gene therapies administered after development, and enable packing in the size restricted 4.9-kb rAAV (recombinant adeno-associated virus) genome.

There is a need for characterized human PAX6 promoters for gene expression, for instance in human gene therapy applications. It is in particular useful to identify small promoter elements that are sufficient to drive expression in certain cell types, for instance retinal cells. Such small promoter elements, or "mini-promoters" are particularly useful in certain applications, for instance they are more amenable to insertion into viral vectors used in gene therapy applications.

SUMMARY

The present invention provides novel nucleic acid sequence compositions and methods relating to minimal human PAX6 promoters. The invention is based in part on the surprising discovery that certain minimal PAX6 promoter elements are capable of expressing in specific cell types in cells eye.

In one embodiment of the invention, there is provided an isolated nucleic acid fragment comprising a PAX6 mini-promoter, wherein the PAX6 mini-promoter comprises one or more PAX6 regulatory elements operably linked in a non-native conformation to a PAX6 basal promoter. The PAX6 mini-promoter may have a nucleic acid sequence substantially similar in sequence and function to SEQ ID NO: 1-7. The PAX6 basal promoter may have a nucleic acid sequence that is substantially similar in sequence and function to SEQ ID NO: 8 or 9. The PAX6 regulatory element may have a nucleic acid sequence that is substantially similar in sequence and function to one or more of SEQ ID NO: 10-16, e.g. comprising one, two, three, four or five of the regulatory elements set forth in the provided sequences. The PAX6 mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expressible sequence may encode a PAX6 protein or an isoform or fragment thereof.

In some embodiments of the invention, the expressible sequence encodes a PAX6-derived cDNA or a PAX6-derived mini-gene, where a PAX6-derived mini-gene comprises PAX6 coding sequences operably linked to one or more non-coding elements, e.g. introns, transcription termination signals, enhancer sequences, and the like. Introns, enhancers, etc. linked to coding sequences may be native PAX6 sequences, or may be an exogenous sequence. In one embodiment, the expressible sequence is a PAX6 coding sequence substantially similar in sequence and function to SEQ ID NO: 17, optionally configured as a mini-gene. In other embodiments, PAX6 mini-promoters that are operably linked to an expressible PAX6 sequence are substantially similar in sequence and function to SEQ ID NO: 18-21.

In one embodiment, there is provided an expression construct comprising a PAX6 mini-promoter, wherein the PAX6 mini-promoter comprises one or more PAX6 regulatory elements operably linked in a non-native conformation to a PAX6 basal promoter. The PAX6 mini-promoter may have a nucleic acid sequence that is substantially similar in sequence and function to SEQ ID NO: 1-7. The PAX6 basal promoter may have a nucleic acid sequence that is substantially similar in sequence and function to one or more of SEQ ID NO: 8 or 9. The one or more PAX6 regulatory elements may have a nucleic acid sequence that is substantially similar in sequence and function to SEQ ID NO: 10-16. The PAX6 mini-promoter may further be operably linked to an expressible sequence as described above. The expression construct may be provided in an expression vector, or may be provided as a sequence for insertion into a genome.

The expressible sequence may encode a PAX6 protein or an isoform or fragment thereof. In some embodiments of the invention, the expressible sequence may encode a PAX6-derived cDNA or a PAX6-derived intron operably joined to a PAX6 cDNA or other PAX6 coding sequence. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21. The expression construct may further comprise a genomic targeting sequence. In one embodiment, there is provided a method for expressing a gene, protein, RNA interference molecule or the like in a cell, the method comprising introducing into the cell an expression construct comprising a PAX6 mini-promoter element, wherein the PAX6 mini-promoter element comprises one or more PAX6 regulatory elements operably linked in a non-native conformation to a PAX6 basal promoter element. Cells of interest for expression include, without limitation, cells in the eye and progenitors thereof, e.g. retinal cells, Müller glia cells, ganglion cells, horizontal cells, amacrine cells, corneal cells, etc. Cells of interest also include, without limitation, cells in the brain, spinal cord, pineal gland, lacrimal gland, teeth, gut, pancreas, etc., and their progenitors.

The PAX6 mini-promoter may have a nucleic acid sequence substantially similar in sequence and function to SEQ ID NO: 1-7. The PAX6 basal promoter may have a nucleic acid sequence, which is substantially similar in sequence and function to SEQ ID NO: 8 or 9. The PAX6 regulatory element may have a nucleic acid sequence that is substantially similar in sequence and function to one or more of SEQ ID NO: 10-16. The PAX6 mini-promoter may further be operably linked to an expressible sequence, e.g. reporter genes, genes encoding a polypeptide of interest, regulatory RNA sequences such as miRNA, siRNA, antisense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression construct may comprise a genomic targeting sequence. The genomic targeting sequence may be HPRT. The expressible sequence may encode a PAX6 protein or an isoform or fragment thereof. The expressible sequence may be a PAX6-derived cDNA or a PAX6-derived mini-gene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

In one embodiment of the invention, there is provided a method for identifying or labeling a cell, the method comprising introducing into the cell an expression vector comprising a PAX6 mini-promoter element, wherein the PAX6 mini-promoter element comprises one or more PAX6 regulatory elements operably linked in a non-native conformation to a PAX6 basal promoter element, and wherein the expressible sequence comprises a reporter gene. The PAX6 mini-promoter element may have a nucleic acid sequence substantially similar in sequence and function to SEQ ID NO: 1-7. The PAX6 basal promoter element may have a nucleic acid sequence substantially similar in sequence and function to SEQ ID NO: 8 or 9. The PAX6 regulatory element may have a nucleic acid sequence substantially similar in sequence and function to one or more of SEQ ID NO: 10-16. In some embodiments, the cell is in the eye and progenitors thereof, e.g. retinal cells, retinal Müller glia, ganglion cells, horizontal cells, amacrine cells, corneal cells, etc. In some embodiments, the cells are in the brain, spinal cord, pineal gland, lacrimal gland, teeth, gut, pancreas, etc., or their progenitors. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like. The expressible sequence may encode a PAX6 protein or an isoform or fragment thereof. In some embodiments of the invention, the expressible sequence may be a PAX6-derived cDNA or a PAX6-derived mini-gene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

In one embodiment of the invention, there is provided a method for monitoring or tracking the development or maturation of a cell, the method comprising: 1) introducing into the cell an expression vector comprising a PAX6 mini-promoter element operably linked to an expressible sequence, wherein the PAX6 mini-promoter element comprises one or more PAX6 regulatory elements operably linked in a non-native conformation to a PAX6 basal promoter element, and wherein the expressible sequence comprises a reporter gene; and 2) detecting the expression of the reporter gene in the cell of in progeny of the cell as a means of determining the lineage, identity or developmental state of the cell or cell progeny. The PAX6 mini-promoter element may have a nucleic acid sequence substantially similar in sequence and function to SEQ ID NO: 1-7. The PAX6 basal promoter element may have a nucleic acid sequence substantially similar in sequence and function to SEQ ID NO: 8 or 9. The PAX6 regulatory element may have a nucleic acid sequence substantially similar in sequence and function to one or more of SEQ ID NO: 10-16. In some embodiments, the cell is an eye cell or progenitor thereof, including without limitation retinal cells, retinal Müller glia, ganglion cells, horizontal cells, amacrine cells, corneal cells, etc. In some embodiments, the cell is, without limitation, a brain, spinal cord, pineal gland, lacrimal gland, teeth, gut, pancreas, etc., cell or progenitors thereof. The expressible sequence may encode a PAX6 protein or an isoform or fragment thereof. In some embodiments of the invention, the expressible sequence may be a PAX6-derived cDNA or a PAX6-derived mini-gene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

In certain embodiments of the invention, there is thus provided a method of treatment of a subject having a disease or condition of the eye, brain, spinal cord, pineal gland, lacrimal gland, teeth, gut, or pancreas, the method comprising administering to the subject a therapeutically effective dose of a composition comprising a PAX6 mini-promoter element, wherein the PAX6 mini-promoter element comprises one or more PAX6 regulatory elements operably linked in a non-native conformation to a PAX6 basal promoter element. The PAX6 mini-promoter element may have a nucleic acid sequence substantially similar in sequence and function to SEQ ID NO: 1-7. The PAX6 basal promoter element may have a nucleic acid sequence substantially similar in sequence and function to SEQ ID NO: 8 or 9. The PAX6 regulatory element may have a nucleic acid sequence substantially similar in sequence and function to SEQ ID NO: 10-16. The disease or condition may include retinal diseases, myopia, retinal degeneration, retinal damage, blindness, macular degeneration, retinitis pigmentosa, inherited retinal genetic diseases, dry eye syndrome, foveal hypoplasia, diabetic retinopathy, cone rod dystrophy, hypertensive/diabetic retinopathy, glaucoma, WAGR syndrome, WAGRO syndrome, chromosome 11p13 deletion syndrome, sjögrens syndrome, keratitis, coloboma, optic nerve hypoplasia, peters anomaly, ectopic pupillae, corneal dysplasia, corneal degeneration, corneal damage, lens dysplasia, lens degeneration, lens damage, or aniridia. The disease or condition may also include brain diseases, intellectual disability, functional conductivity, autism, spinal cord diseases, pineal gland disease, lacrimal gland disease, tooth disease, gastrointestinal disease, or diabetes. The therapeutic or beneficial compound may be a light-sensitive compound, for instance rhodopsin, channel rhodopsin, etc. In one embodiment, the therapeutic or beneficial compound may be a PAX6 protein or an isoform or fragment thereof. In another embodiment, the therapeutic or beneficial compound may be a PAX6-derived cDNA or a PAX6-derived mini-gene. In one embodiment, the therapeutic or beneficial compound is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

ITR (light grey arrow pointing counter clockwise). The plasmid also carries an ampicillin resistance gene (black arrow) and a ColE1 origin of replication (grey rectangle).

Figure 4:
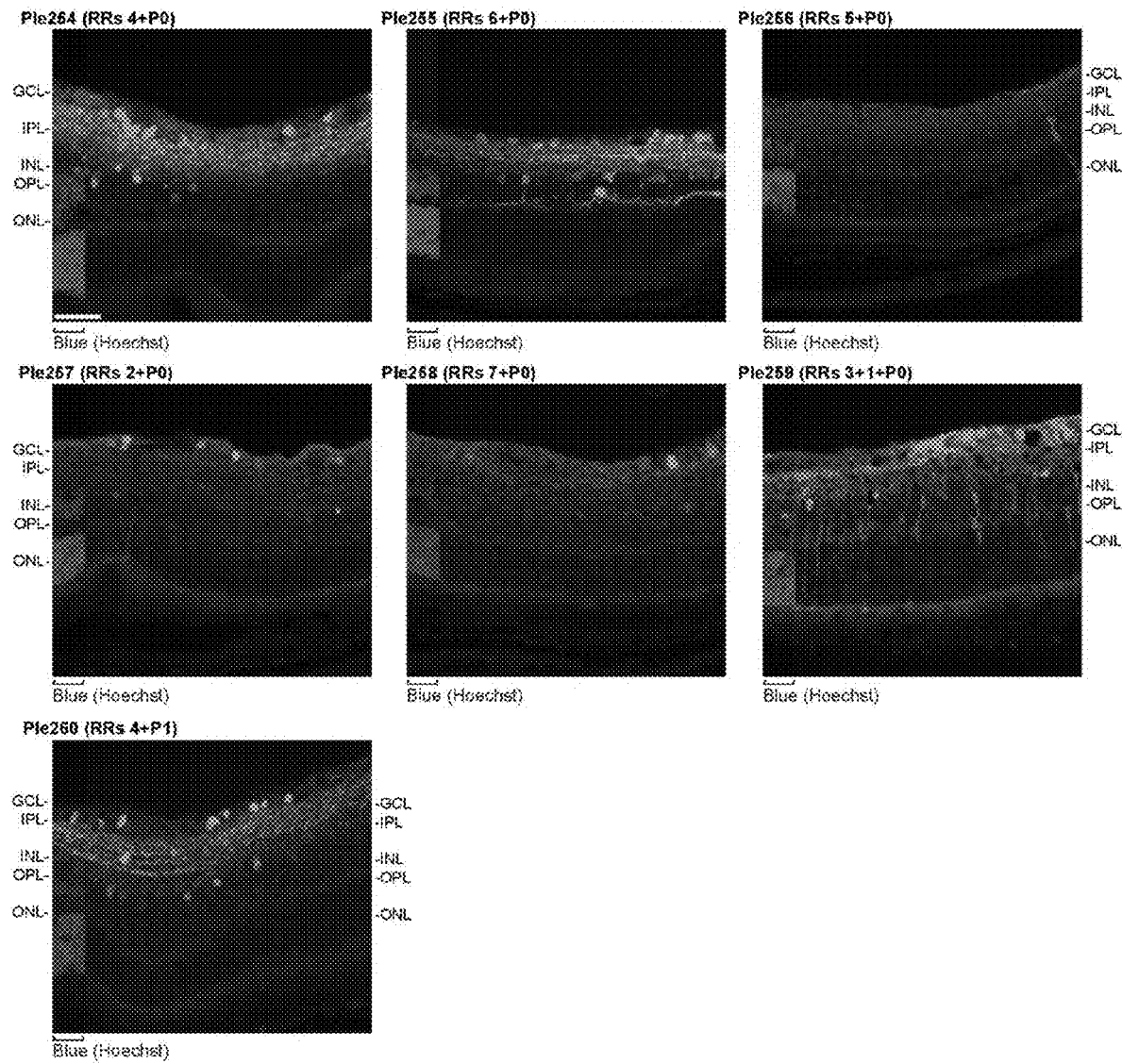

FIG. 4. Four PAX6 MiniPromoters drive EmGFP (Emerald GFP) expression overlapping with PAX6 expression in the adult mouse retina. Green (GFP antibody) labelling of mouse retinas transduced after intravitreal injection with modified rAAV2 encoding PAX6 Mini-Promoters driving EmGFP expression revealed Mini-Promoter expression patterns. Ple254 (SEQ ID NO: 1), Ple255 (SEQ ID NO:2), Ple259 (SEQ ID NO:6), and Ple260 (SEQ ID NO:7) all drive consistent EmGFP expression in the GCL (ganglion cell layer) and INL (inner nuclear layer) whereas Ple256 (SEQ ID NO:3), Ple257 (SEQ ID NO:4), and Ple258 (SEQ ID NO: 5) drive more limited EmGFP expression. IPL, inner plexiform layer; OPL, outer plexiform layer; scale bar, 50 μm.

Figure 5:
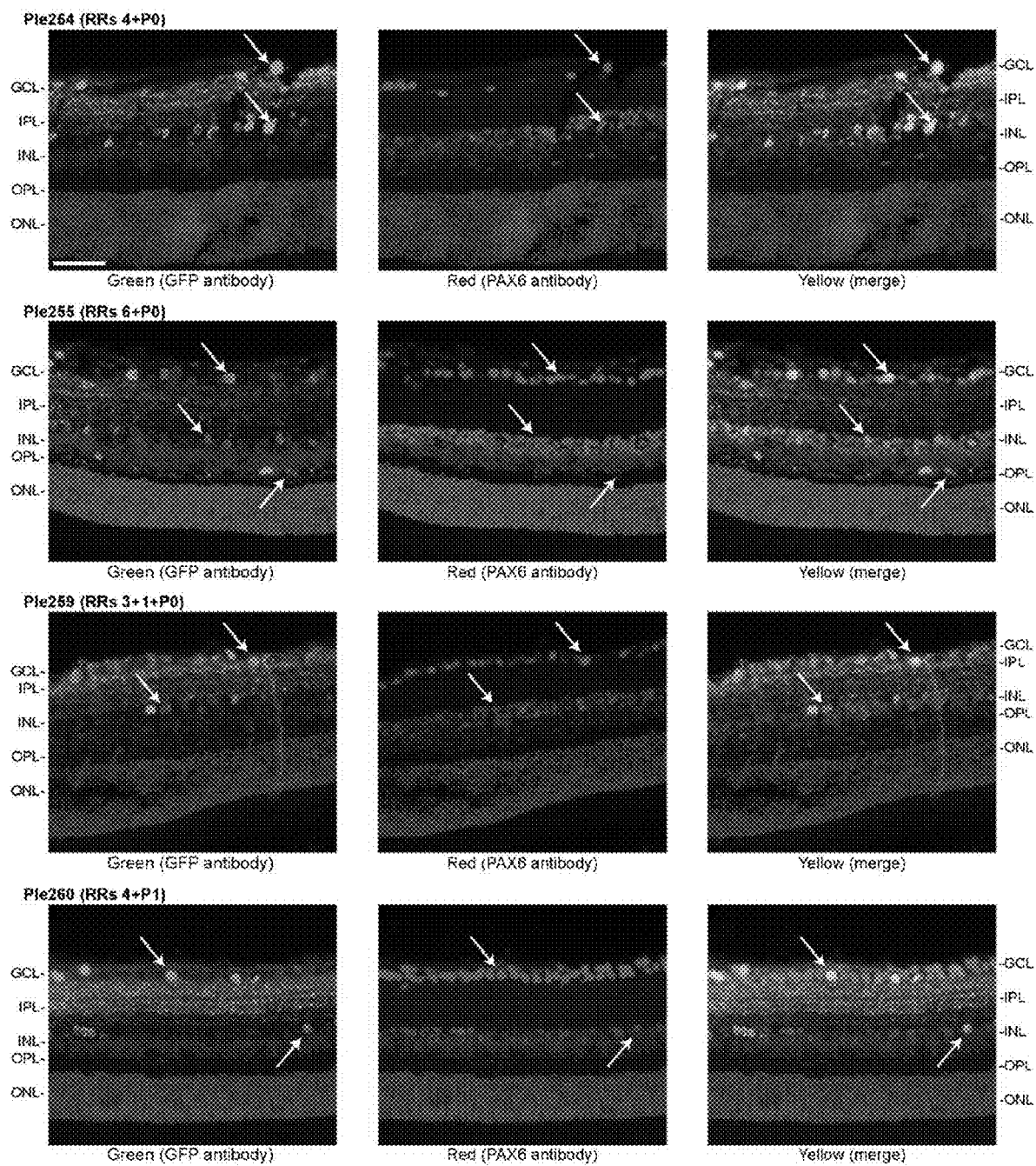

FIG. 5. Ple254 (SEQ ID NO: 1), Ple255 (SEQ ID NO: 2), Ple259 (SEQ ID NO: 6) and Ple260 (SEQ ID NO: 7) drive expression overlapping with the expression pattern of PAX6 in the mouse retina. Representative histological sections of mouse retinas transduced by intravitreally injected modified rAAV2 encoding PAX6 Mini-Promoters driving EmGFP (Emerald GFP). Green (GFP antibody) and red (PAX6 antibody) co-labelling revealed that all four Mini-Promoters drive EmGFP expression overlapping with elements of the PAX6 expression profile in the GCL (ganglion cell layer) and INL (inner nuclear layer). IPL, inner plexiform layer; OPL, outer plexiform layer; ONL, outer nuclear layer; blue, Hoechst; arrows, examples of co-labeled cells; scale bar, 50 μm.

Figure 6:
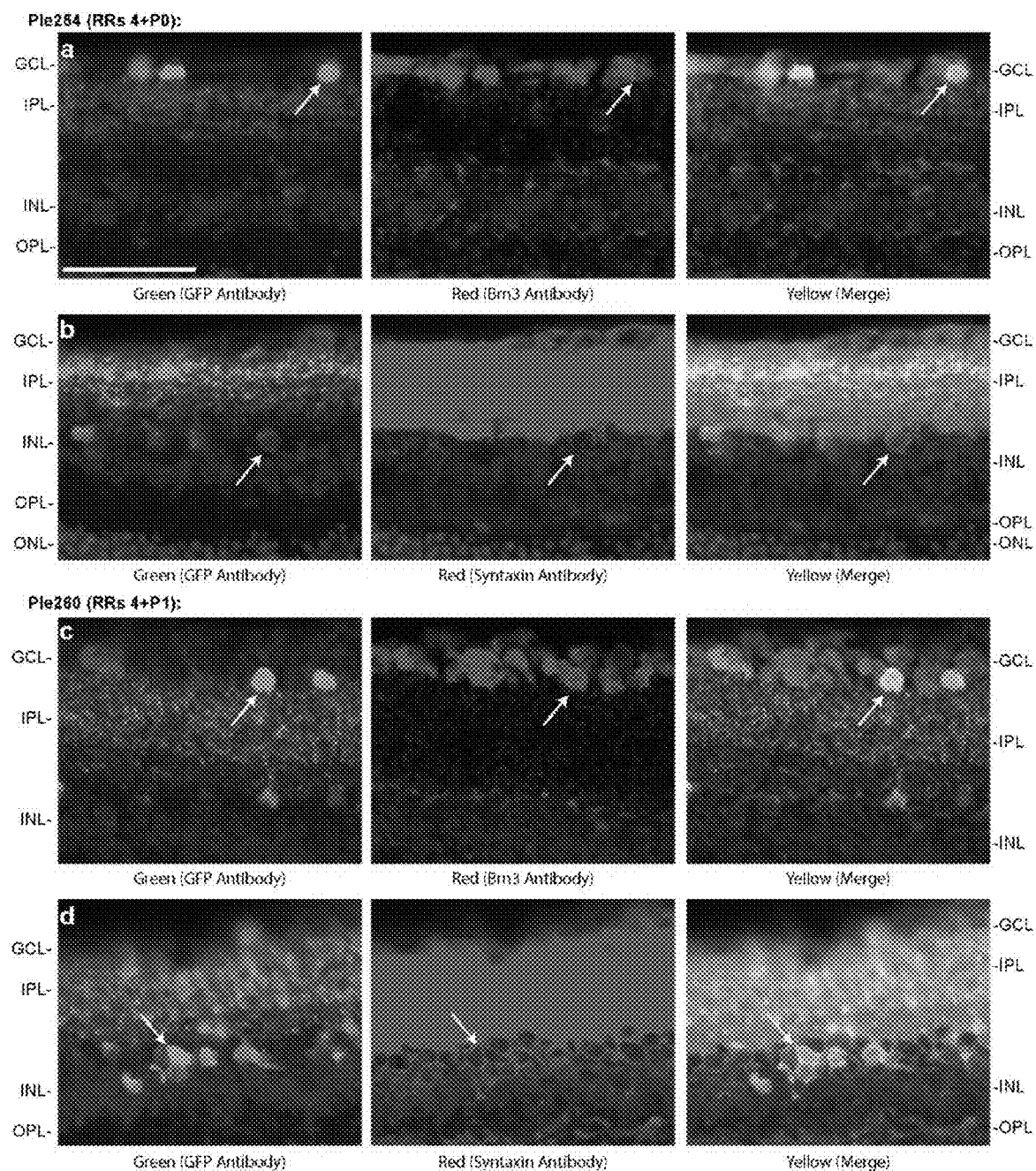

FIG. 6. Ple254 (SEQ ID NO: 1) and Ple260 (SEQ ID NO: 7) drive EmGFP (emerald GFP) expression in mouse retinal ganglion cells and amacrine cells. (a and c) Green (GFP antibody) and red (Brn3 antibody, retinal ganglion cell marker) co-labelling revealed that both Ple254 (SEQ ID NO: 1) and Ple260 (SEQ ID NO: 7) drive expression in retinal ganglion cells. (b and d) Green (GFP antibody) and red (Syntaxin antibody, an amacrine cell marker) co-labelling revealed that Ple254 (SEQ ID NO: 1) and Ple260 (SEQ ID NO: 7) drive expression in amacrine cells. GCL, ganglion cell layer; IPL, inner plexiform layer; INL, inner nuclear layer; OPL, outer plexiform layer; ONL, outer nuclear layer; blue, Hoechst; arrows, examples of co-labeled cells; scale bar, 50 μm.

Figure 7:
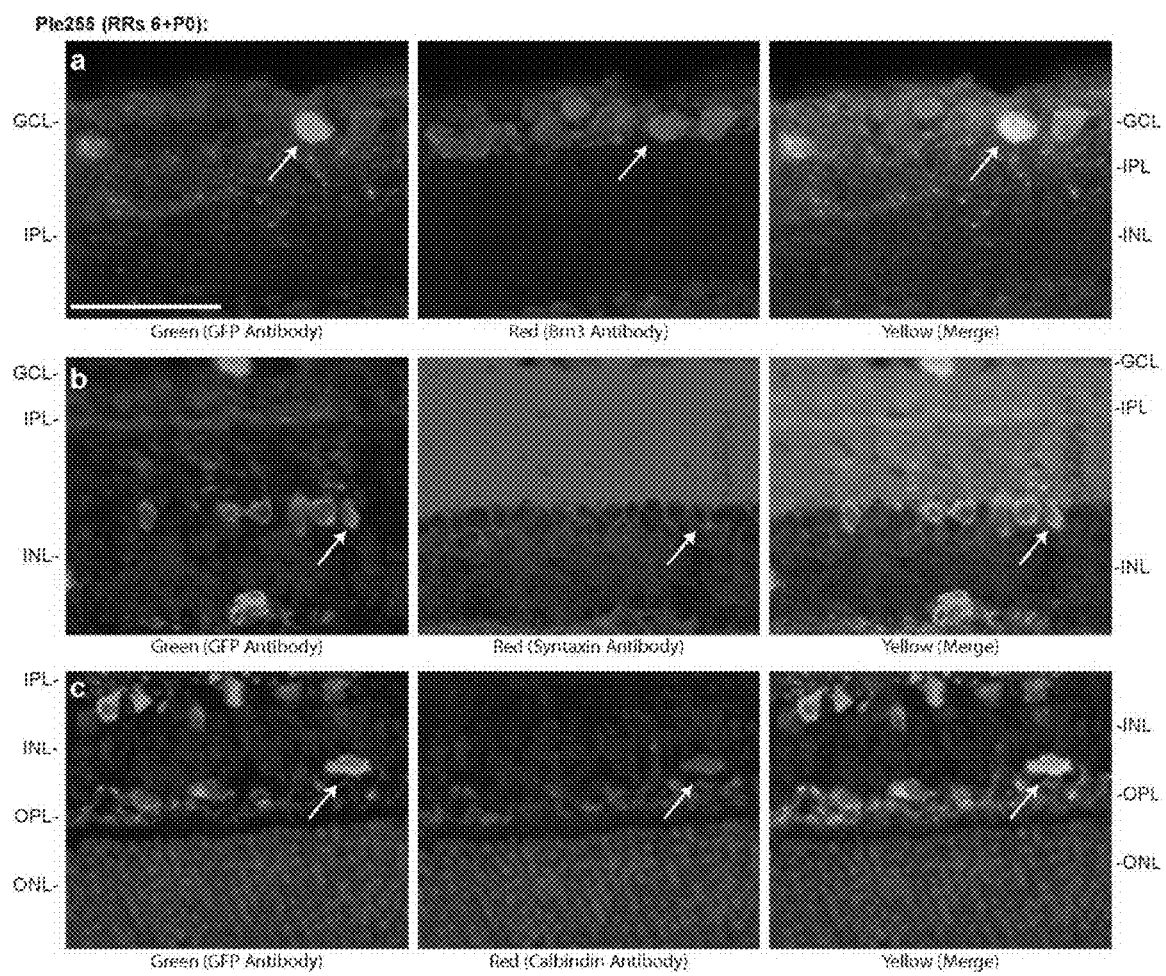

FIG. 7. Ple255 (SEQ ID NO: 2) drives EmGFP (emerald GFP) expression in mouse retinal ganglion, amacrine, and horizontal cells. (a) Green (GFP antibody) and red (Brn3 antibody, a retinal ganglion cell marker) co-labelling revealed that Ple255 (SEQ ID NO: 2) drives expression in retinal ganglion cells. (b) Green (GFP antibody) and red (Syntaxin antibody, an amacrine cell marker) co-labelling revealed that Ple255 (SEQ ID NO: 2) drives expression in amacrine cells. (c) Green (GFP antibody) and red (Calbindin antibody, a horizontal cell marker) co-labelling revealed that Ple255 (SEQ ID NO: 2) drives expression in horizontal cells. GCL, ganglion cell layer; IPL, inner plexiform layer; INL, inner nuclear layer; OPL, outer plexiform layer; ONL, outer nuclear layer; blue, Hoechst; arrows, examples of co-labeled cells; scale bar, 50 μm.

Figure 8:
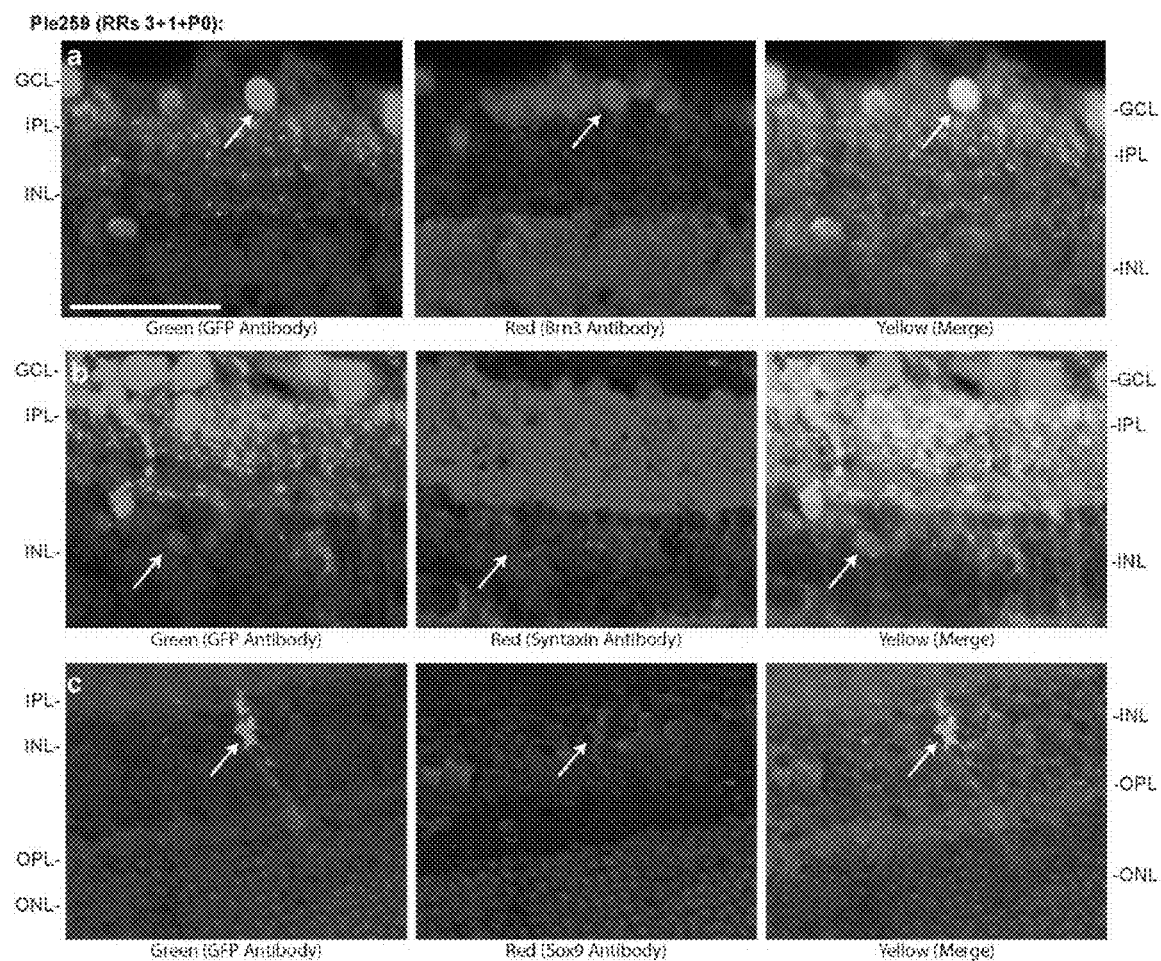

FIG. 8. Ple259 (SEQ ID NO: 6) drives EmGFP (emerald GFP) expression in mouse retinal ganglion, amacrine, and Müller glia cells. (a) Green (GFP antibody) and red (Brn3 antibody, retinal ganglion cell marker) co-labelling revealed that Ple259 (SEQ ID NO: 6) drives expression in retinal ganglion cells. (b) Green (GFP antibody) and red (Syntaxin antibody, amacrine cell marker) co-labelling revealed that Ple259 (SEQ ID NO: 6) drives expression in amacrine cells. (c) Green (GFP antibody) and red (SOX9 antibody, Müller glia marker) co-labelling revealed that Ple259 drives expression in Müller glia. GCL, ganglion cell layer; IPL, inner plexiform layer; INL, inner nuclear layer; OPL, outer plexiform layer; ONL, outer nuclear layer; blue, Hoechst; arrows, examples of co-labeled cells; scale bar, 50 μm.

Figure 9:
Figure 9:
Figure 9:
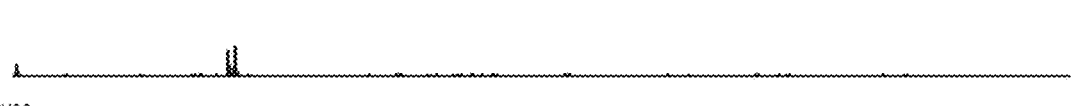
Figure 9:
Figure 9:

FIG. 9. PAX6 ocular transcription is primarily driven by two promoters, as revealed by CAGE (cap analysis gene expression) data. A model of PAX6 was constructed by visually aligning PAX6 mRNA transcripts to define the intron-exon structure, and analyzing CAGE data to define the TSSs (transcriptional start sites). (a) Intron-exon structure of PAX6 captured in ten different transcripts retrieved from UCSC Genes. The coloring is defined by the source database: black transcripts have the highest validation level and a corresponding entry in the Protein Data Bank; grey transcripts have been reviewed or validated by RefSeq, SwissProt, or CCDS. Thick and thin rectangles indicate protein coding and non-protein coding exons respectively, thin lines represent intronic sequences. (b) CAGE data retrieved from the FANTOM5 consortium defines the promoter structure of PAX6 in multiple human tissues (19). Peaks represent common transcription initiation positions, indicative of a promoter. Tracks were curated by source into three groups: 'All human tissues' contained CAGE data from normal human tissues, excluding cancer or induced pluripotent stem cells; 'CNS tissues' contained data from the human central nervous system excluding the neural retina; 'Ocular tissues' contained data from tissues of the eye including the neural retina. All three groups indicated a strong bias for promoters P0 and P1, while Pa (as indicated in c) is supported only by a very small peak in 'all human' and 'ocular' tissues. Evidence for an additional previously described promoter, P4, was not found in this data set. (c) Schematic of the resulting PAX6 model containing 17 exons, transcribed from three promoters. Illustrative features are as in a, with the addition of promoters indicated by arrows above the schematic and aligned to the TSS positions in b. Previously proposed P4 was included in brackets for completeness.

Figure 10:
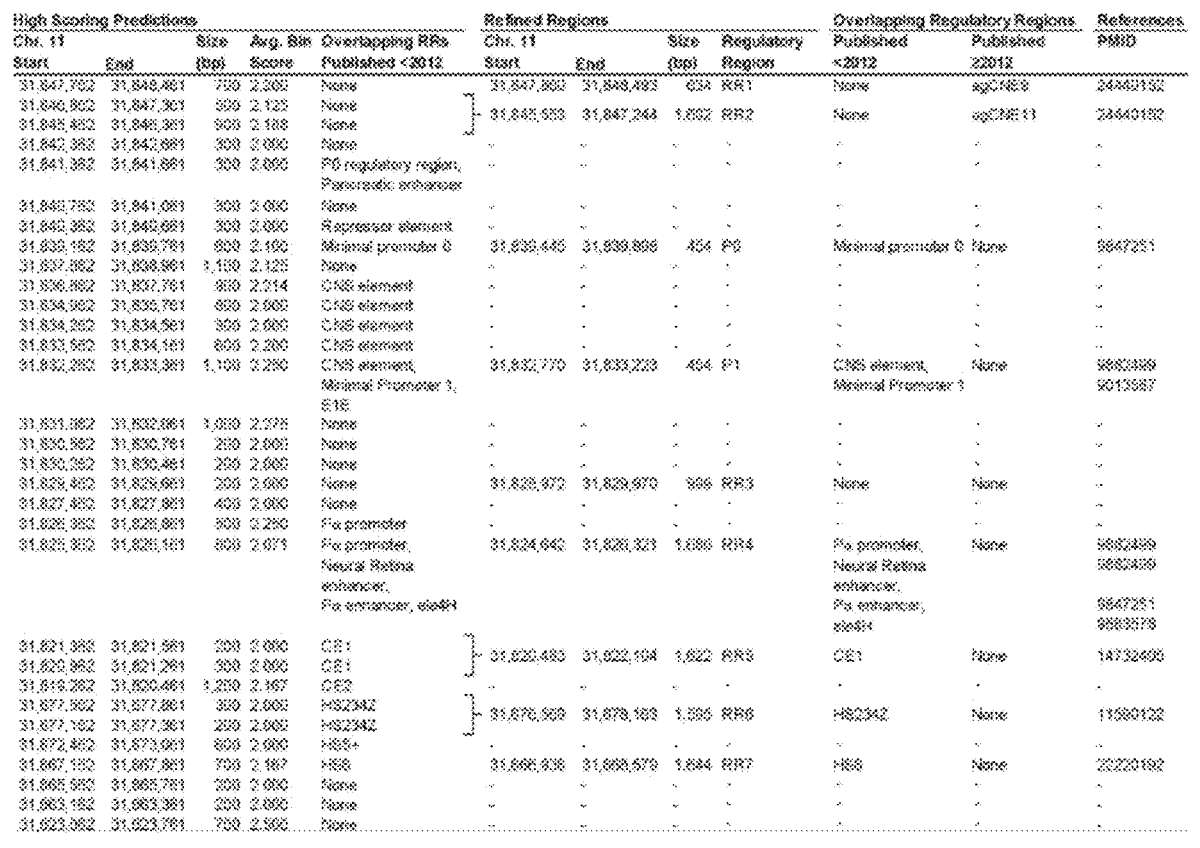

FIG. 10. Nine refined RRs (regulatory regions) were selected from the 31 putative RRs. Selection was based largely on: RR size since Mini-Promoters need to be small, Ave. Bin Score 2.0, overlap with previously published RRs known to express in the adult eye, spanning the highly-interactive regulatory neighborhood, and inclusion of some novel regions (of which RR1 and RR2 were subsequently described in the literature). Two of the nine RRs are core promoter regions overlapping P0 and P1. None, no published RRs in that region; dash, region not selected for study; bp, base pair; Chr., Chromosome; NA, not applicable.

Figure 11:
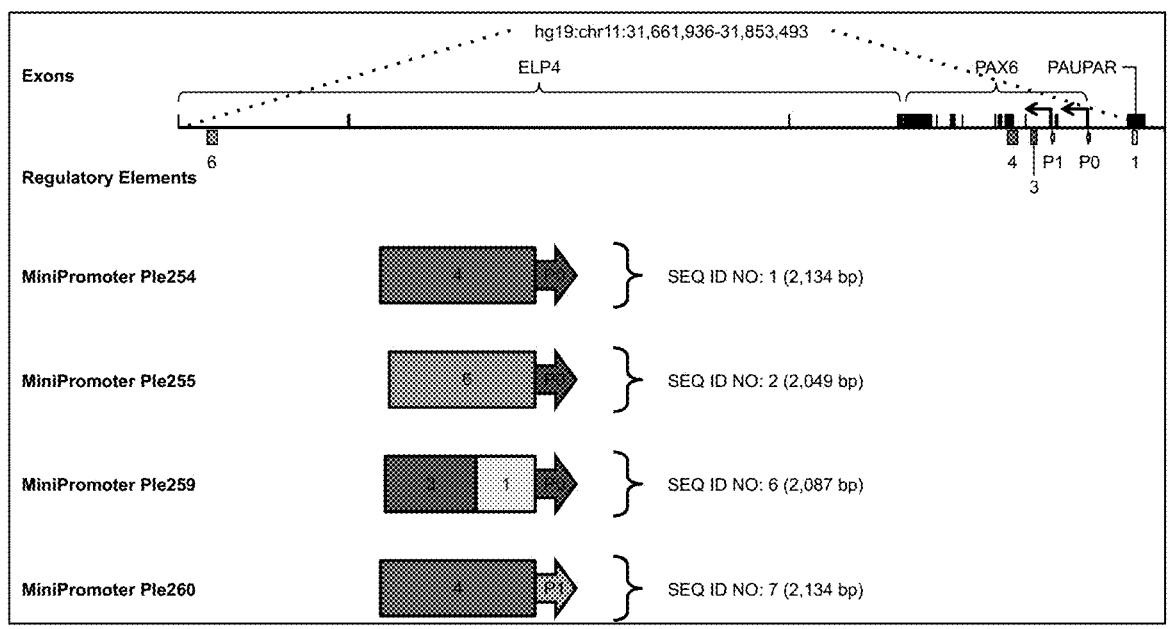

FIG. 11. Overview of the human PAX6-based Mini-Promoters Ple254, Ple255, Ple259, and Ple260 (SEQ ID NO: 1, 2, 6 and 7, respectively). Ple254 comprises the PAX6 regulatory element 4 (blue box; SEQ ID NO: 13) linked in a non-native conformation to the PAX6 basal promoter element 0 (P0; red arrow; SEQ ID NO: 8). Ple255 comprises the PAX6 regulatory element 6 (green box; SEQ ID NO: 15) linked in a non-native conformation to P0. Ple259 comprises PAX6 regulatory elements 1 and 3 (yellow and purple boxes, respectively; SEQ ID NO: 10 and 12, respectively) linked in a non-native conformation to P0. Ple260 comprises the PAX6 regulatory element 4 linked in a non-native conformation to the PAX6 basal promoter element 1 (P1; pink; SEQ ID NO: 9).

Figure 12:
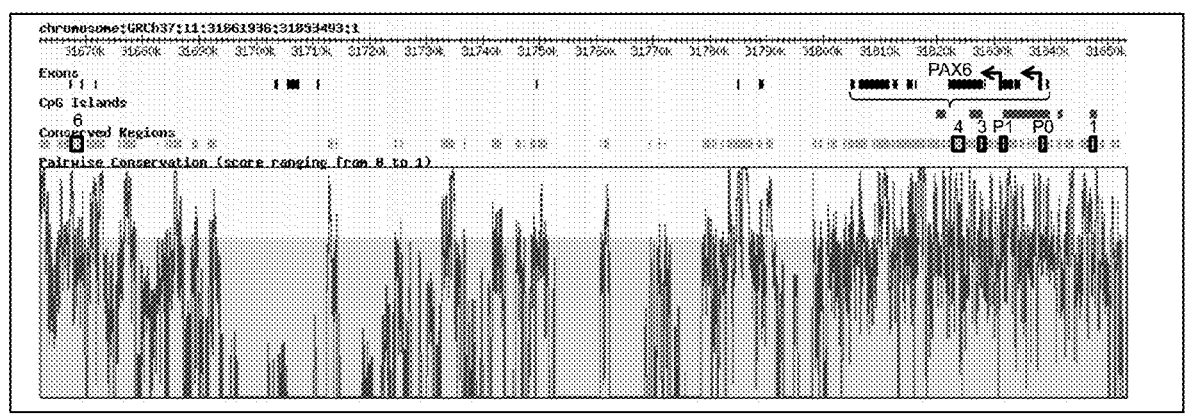

FIG. 12. Conservation profile of the human PAX6-based Mini-Promoters Ple254, Ple255, Ple259, and Ple260 (SEQ ID NO: 1, 2, 6, and 7, respectively). "Conserved Regions" (cyan) are determined by alignment of the human sequence (chr11:31,661,936-31,853,493, genome assembly hg19) and its mouse homolog (chr2:105,494,989-105,641,497, genome assembly mm9) using a threshold on the percentage of identity of 70% (see shading in "Pairwise Conservation" box). Black squares delimit the Mini-Promoter regulatory elements 1, 3, 4, and 6 (SEQ ID NO: 10, 12, 13, and 15, respectively) and basal promoter elements 0 and 1 (P0 and P1, respectively; SEQ ID NO: 8 and 9, respectively). The red line indicates the "Pairwise Conservation" score at each position.

Figure 13:
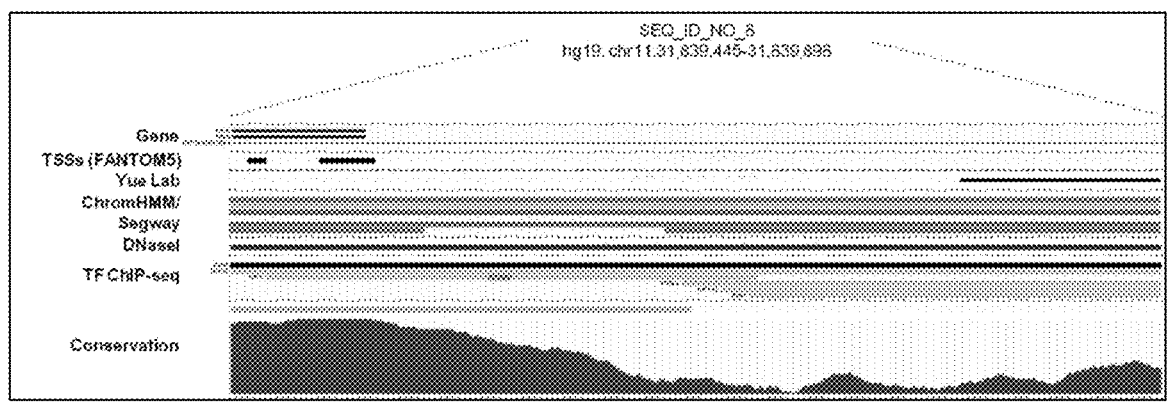

FIG. 13. Supporting evidence for basal promoter 0 (SEQ ID NO: 8). About 50% of the region is conserved between human and mouse ("Conservation"; cyan thick lines and red profile). The region is open ("DNase I" and "Yue Lab" black/gray thick lines) and predicted to be an active enhancer by a combined hidden Markov model-based method for the functional segmentation of genomes ("ChromHMM/Segway"; yellow thick line). It contains two transcription start sites (TSS), as defined in the FANTOM5 project by cap analysis of gene expression (CAGE). The region is bound by transcription factors (TFs), as identified by chromatin immunoprecipitation (ChIP) coupled to massively parallel DNA sequencing (ChIP-seq), which allows for the identification of protein-DNA interactions in vivo (gray and black thick lines).

Figure 14:
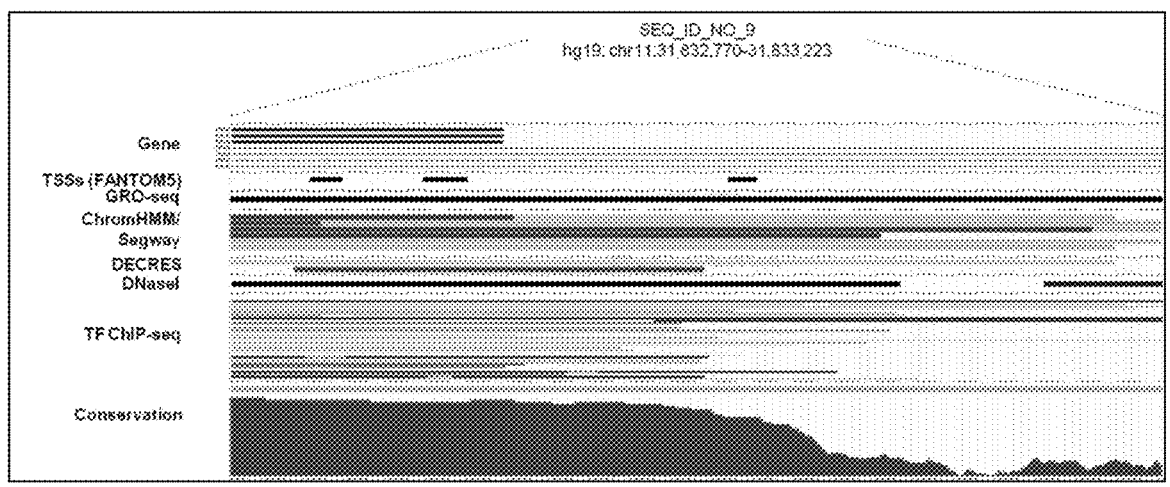

FIG. 14. Supporting evidence for basal promoter 1 (SEQ ID NO: 9). The whole region is conserved between human and mouse ("Conservation"; cyan thick lines and red profile). The region is open ("DNase I" black thick lines) and transcriptionally active, as specified by genomic run-on (GRO) coupled to massively parallel DNA sequencing (GRO-seq), which allows for the calculation of transcription rates (black thick line). It is predicted to work as an active enhancer or promoter (yellow and red thick lines, respectively) by combined "ChromHMM/Segway" and "DECRES", a supervised deep learning method that identifies enhancer and promoter regions in the human genome. The region contains three FANTOM5 TSSs and is enriched in "TF ChIP-seq" peaks (black/gray thick lines).

Figure 15:
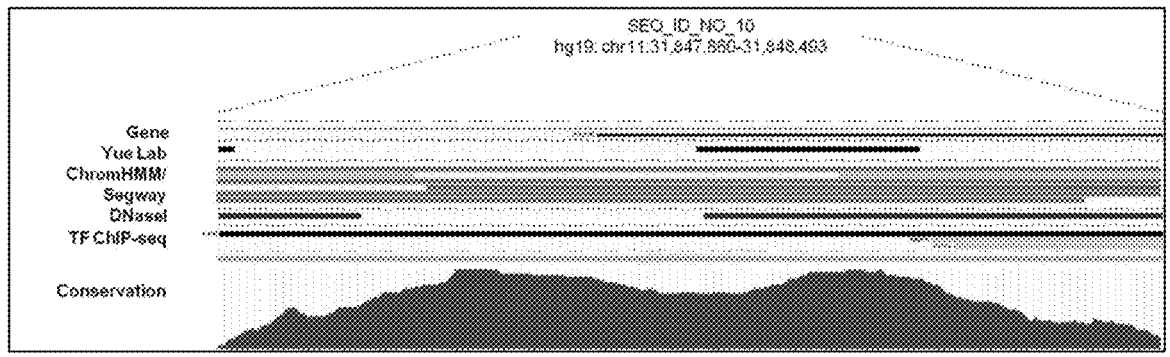

FIG. 15. Supporting evidence for regulatory element 1 (SEQ ID NO: 10). The whole region is conserved between human and mouse ("Conservation"; cyan thick lines and red profile). It has been linked to the PAX6 gene based on DNaseI hypersensitivity sites ("Yue Lab" black thick lines). The region is open ("DNase I" black thick line), and enriched in "TF ChIP-seq" peaks (black/gray thick lines), and has been predicted to work as an active enhancer by combined "ChromHMM/Segway" (yellow line).

Figure 16:
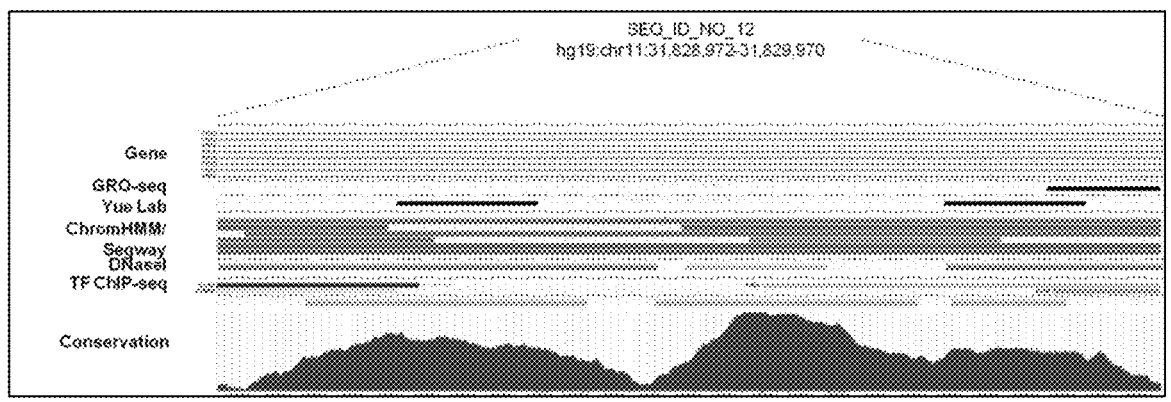

FIG. 16. Supporting evidence for regulatory element 3 (SEQ ID NO: 12). About 70% of the region is conserved between human and mouse ("Conservation"; cyan thick lines and red profile). The region works as a promoter-flanking region (predicted by combined "ChromHMM/Segway"; salmon-color thick line), is open ("DNase I" gray/black thick line), transcriptionally active ("GRO-seq" black thick line), and contains "TF ChIP-seq" peaks (black/gray thick lines). It is linked to the PAX6 gene based on DNaseI hypersensitivity sites ("Yue Lab" black thick lines).

Figure 17:
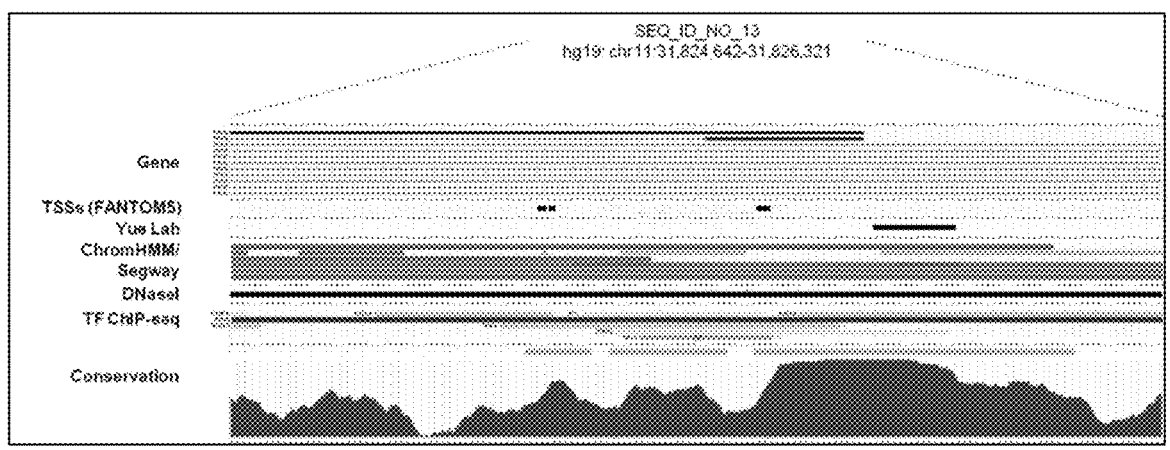

FIG. 17. Supporting evidence for regulatory element 4 (SEQ ID NO: 13). About 55% of the region is conserved between human and mouse ("Conservation"; cyan thick lines and red profile). The region is open ("DNase I" and "Yue Lab" black/gray thick lines) and predicted to work as an active enhancer by combined "ChromHMM/Segway" (yellow thick line). It contains several FANTOM5 TSSs and "TF ChIP-seq" peaks (gray and black thick lines).

Figure 18:
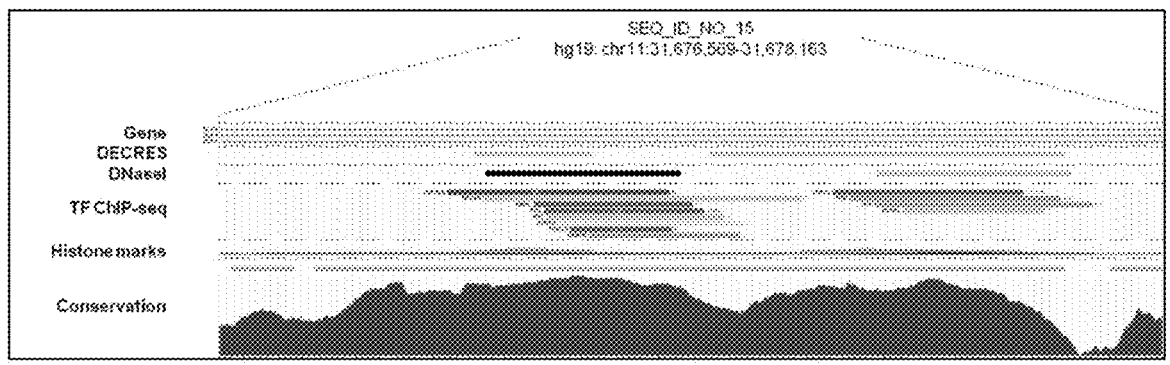

FIG. 18. Supporting evidence for regulatory element 6 (SEQ ID NO: 15). About 92% of the region is conserved between human and mouse ("Conservation"; cyan thick lines and red profile). The region is open ("DNase I" black/gray thick lines), transcriptionally active ("Histone marks" profile), and contains several "TF ChIP-seq" peaks (gray/black thick lines. It has been predicted to work as an active enhancer by "DECRES" (yellow thick line).

Figure 19:
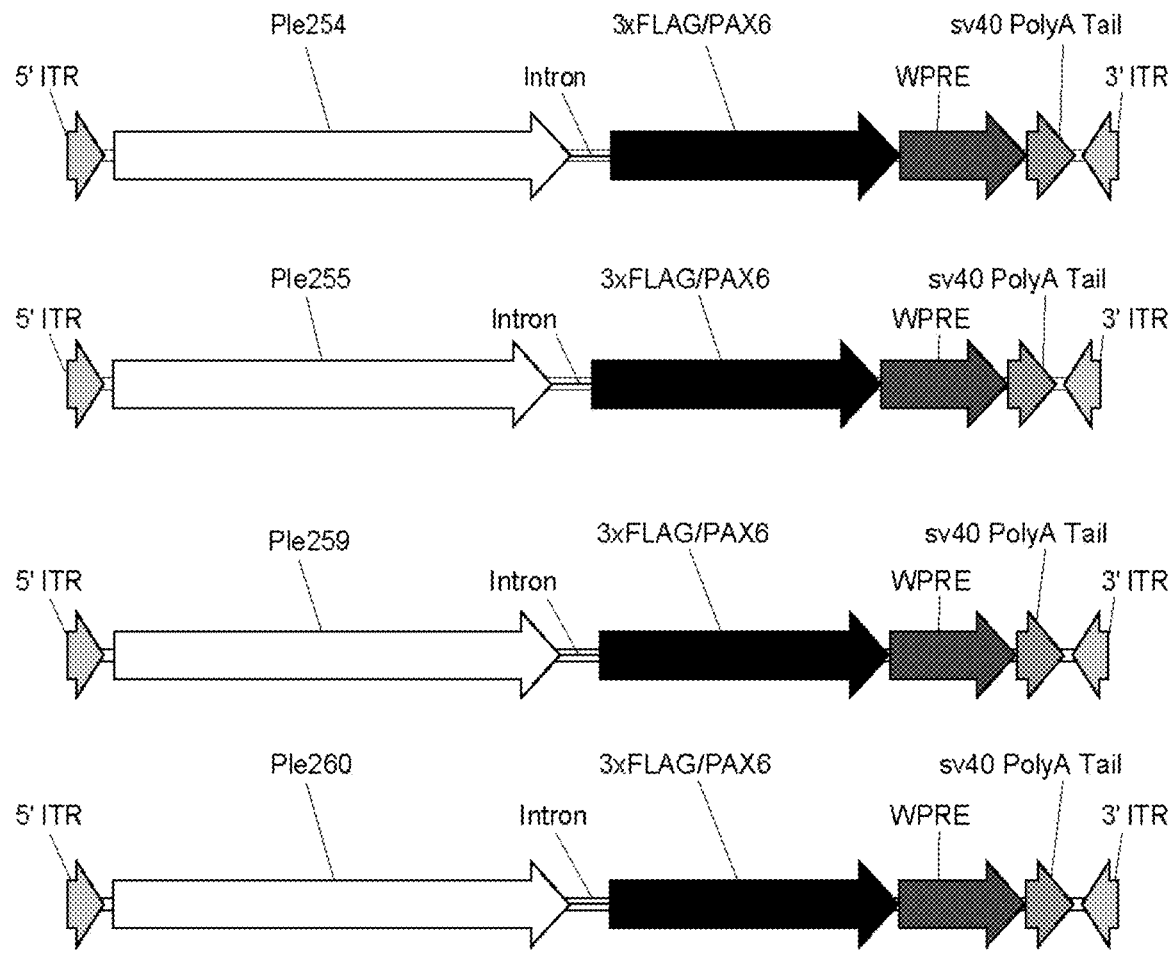

FIG. 19. PAX6 Mini-Promoters were recloned to drive a 3×FLAG tag fused to the N-terminal of PAX6 (3×FLAG/PAX6). Mini-Promoters (white arrow with black outline) and a 3×FLAG/PAX6 open reading frame (black arrow) were cloned into viral backbones containing the same 5' ITR (light gray arrow pointing to the right), chimeric intron (from pCI mammalian expression vector, Promega, Madison, W, USA), WPRE (dark gray arrow), sv40 PolyA Tail (medium gray arrow; from pCI mammalian expression vector, Promega), and a 3' ITR (light gray arrow pointing left).

Figure 20:
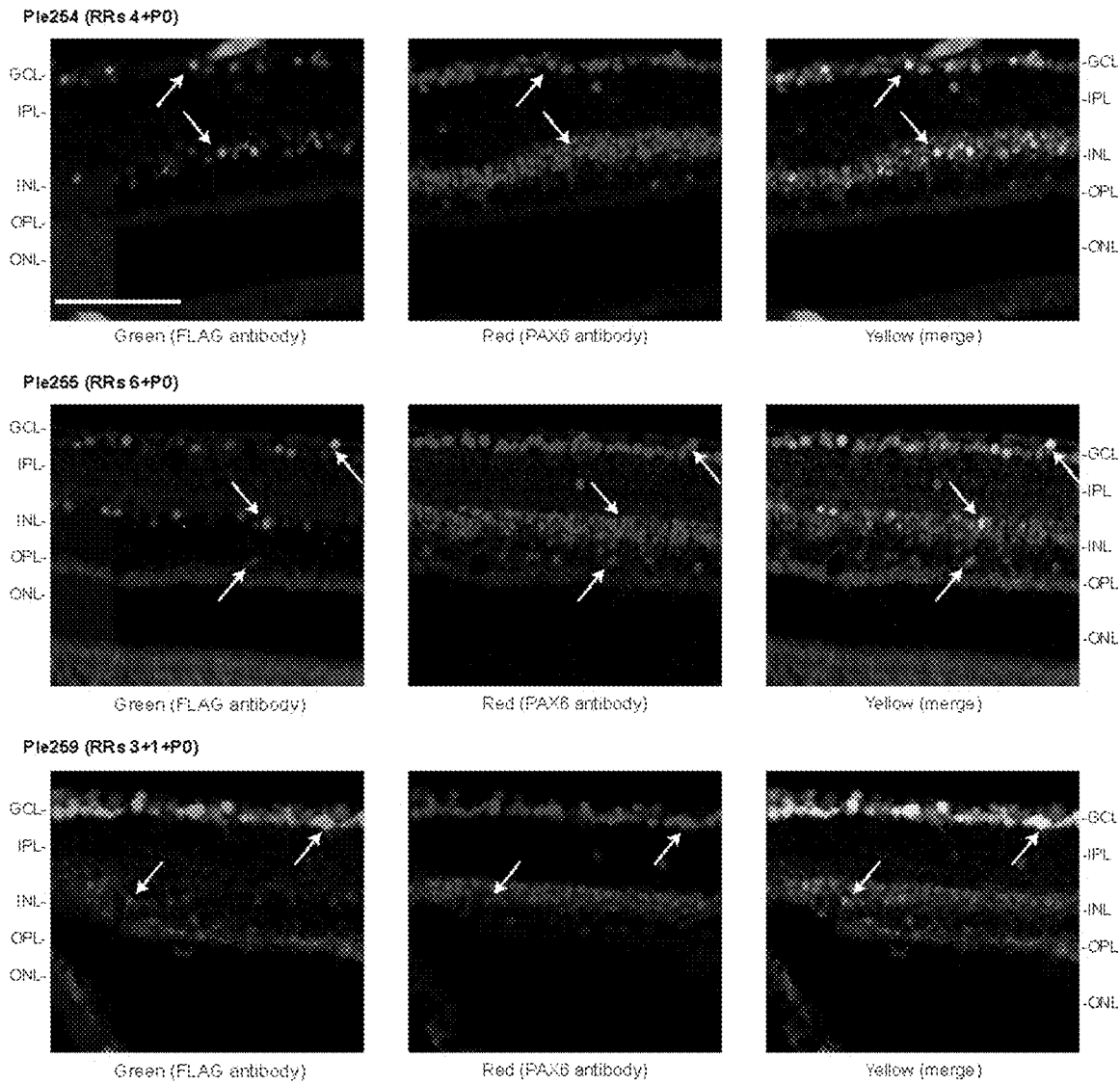

FIG. 20. PAX6 Mini-Promoters drive restricted 3×FLAG/PAX6 expression in the adult mouse retina. Ple254 drove 3×FLAG/PAX6 expression in the ganglion cell layer (GCL) and inner nuclear layer (INL) as determined by FLAG tag (green) and PAX6 (red) immunofluorescent co-labelling (yellow). Similarly, Ple255 and Ple259 both drove 3×FLAG/PAX6 expression in the GCL and INL. Inner plexiform layer (IPL), outer plexiform layer (OPL), outer nuclear layer (ONL). Scale bar represents 50 microns.

DETAILED DESCRIPTION

The compositions of the present invention include novel polynucleotides comprising PAX6 promoter elements (also referred to herein as PAX6 mini-promoters) as well as novel expression vectors comprising said PAX6 promoter elements (or mini-promoters). The present invention also includes various methods utilizing these novel PAX6 promoter (or mini-promoter) elements or expression vectors.

The term 'PAX6' refers to the gene that encodes the PAX6 protein, also referred to as paired box 6. The human homolog of PAX6 is encoded by the human gene identified as EntrezGene #5080 and is located at chromosomal location 11p13. The protein encoded by human PAX6 has the Protein Accession UniProtKB # P26367, however other protein accession numbers and names may also be assigned to this protein including P26367-1 and PAX6 isoform-a. PAX6 may also include other isoforms and/or splice variants with names including PAX6 isoform-b, PAX6(5a), and accession number P26367-2. Other mammalian PAX6 homologs may include but are not limited to: *Rattus norvegicus* (EntrezGene #25509), *Mus musculus* (EntrezGene #18508), *Macaca mulatta* (EntrezGene #695746), Pan troglodytes (EntrezGene #737387).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter that contains all the basic necessary elements to promote transcriptional expression of an operably linked polynucleotide. Eukaryotic basal promoters typically, though not necessarily, contain a TATA-box and/or a CAAT box. A 'PAX6 basal promoter', in the context of the present invention and as used herein, is a nucleic acid compound having a sequence with at least 65%, at least 70%, at least 80%, at least 85%, at least 90%, at least 95%, at least 97% or at least 99% similarity to SEQ ID NO: 8 or 9.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'PAX6 regulatory element', in the context of the present invention and as used herein, is a nucleic acid compound having a sequence with at least 65%, at least 70%, at least 80%, at least 85%, at least 90%, at least 95%, or at least 99% similarity to any one of SEQ ID NO: 10-16. The present invention provides, in certain embodiments as described herein, different promoters of the PAX6 gene. In some embodiments, the PAX6 promoter comprises one or more PAX6 regulatory elements operably linked to a PAX6 basal promoter.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter may allow easier genetic manipulation, for example in the design and/or construction of expression vectors or other recombinant DNA constructs. In addition, the smaller size may allow easier insertion of DNA constructs into host cells and/or genomes, for example via transfection, transformation, etc. Other advantages of mini-promoters are apparent to one of skill in the art. In some embodiments of the invention, there are thus provided novel PAX6 mini-promoters comprising a PAX6 regulatory element operably linked in a non-native conformation to a PAX6 basal promoter. In general the spacing between the PAX6 regulatory element and the PAX6 basal promoter is not more than about 5 kb, often not more than about 1 kb, more often not more than about 500 nt, and may be not more than about 100 nt, down to a direct joining of the two sequences. In other embodiments, there is provided a minimal PAX6 basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art. In some embodiments of the invention the expressible sequence may encode a PAX6 protein or an isoform or fragment thereof. In some embodiments of the invention, the expressible sequence may be a PAX6-derived cDNA or a PAX6-derived mini-gene. In one embodiment, the expressible sequence may be substantially similar in sequence and function to SEQ ID NO: 17.

The term 'RNA' as used in the present invention includes full-length RNA molecules, which may be coding or non-coding sequences, fragments, and derivatives thereof. For example, a full-length RNA may initially encompass up to about 20 kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (i.e. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 97%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 97%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by northern blot assay or reverse transcriptase PCR of mRNA expression, western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term 'microRNA molecule', 'microRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, mini-circles, viruses, e.g. retroviruses, adenovirus, lentivirus, SV-40, and the like; etc. Many such vectors have been described in the art and are suitable for use with the promoters of the present invention. For example, a "minicircle" vector refers to a small, double stranded circular DNA molecule that provides for persistent, high level expression of a sequence of interest that is present on the vector operably linked to regulatory sequences present on the mini-circle vector, which regulatory sequences control its expression.

Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention. In some embodiments of the invention, the expression sequence may include genome editing proteins such as zinc finger nucleases (ZFNs), transcription activator-like effector nucleases (TALENs) or clustered regularly interspaced short palindromic repeats enzymes (CRISPRs) or encode guide RNAs for such purposes.

Introduction of nucleic acids or expression vectors into cells may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, Wiley and Sons.

In certain embodiments of the invention, there are provided methods of treatment using the nucleic acids, e.g. expression constructs described herein or expression vectors, for instance for gene therapy applications. The nucleic acids or expression vectors of the present invention may be administered in isolation, or may be linked to or in combination with tracer compounds, liposomes, carbohydrate carriers, polymeric carriers, plasmids, nanoparticles or other agents or excipients as will be apparent to one of skill in the art. In an alternate embodiment, such compounds may comprise a medicament, wherein such compounds may be present in a pharmacologically effective amount.

The term 'medicament' as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term 'pharmaceutically acceptable excipient' may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, intraocular, topical or oral administration. An excipient may include sterile aqueous solutions or dispersions for extemporaneous preparation of sterile injectable solutions or dispersion. Use of such media for preparation of medicaments is known in the art.

The nucleic acids or expression vectors of the present invention may be administered to a subject using a viral delivery system. For instance, the nucleic acids may be inserted into a viral vector using well known recombinant techniques. The subsequent viral vector may then be packaged into a virus, such as adenovirus, lentivirus, retrovirus, herpes simplex virus, attenuated virus, adeno-associated virus (AAV), recombinant AAV, and the like. Viral delivery for gene therapy applications is well known in the art. There exist a variety of options for viruses suitable for such delivery, which may also involve selecting an appropriate viral serotype for delivery and expression in an appropriate tissue.

Compositions or compounds according to some embodiments of the invention may be administered in any of a variety of known routes. Examples of methods that may be suitable for the administration of a compound include orally, intravenous, inhalation, intramuscular, subcutaneous, topical, intraperitoneal, intra-ocular, intra-rectal or intra-vaginal suppository, sublingual, and the like. The compounds of the present invention may be administered as a sterile aqueous solution, or may be administered in a fat-soluble excipient, or in another solution, suspension, patch, tablet or paste format as is appropriate. A composition comprising the compounds of the invention may be formulated for administration by inhalation. For instance, a compound may be combined with an excipient to allow dispersion in an aerosol. Examples of inhalation formulations will be known to those skilled in the art. Other agents may be included in combination with the compounds of the present invention to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments of the invention may vary depending on the route of administration (oral, intravenous, inhalation, or the like) and the form in which the composition or compound is administered (solution, controlled release or the like). Determination of appropriate dosages is within the ability of one of skill in the art. As used herein, an 'effective amount', a 'therapeutically effective amount', or a 'pharmacologically effective amount' of a medicament refers to an amount of a medicament present in such a concentration to result in a therapeutic level of drug delivered over the term that the drug is used. This may be dependent on mode of delivery, time period of the dosage, age, weight, general health, sex, and diet of the subject receiving the medicament. Methods of determining effective amounts are known in the art. It is understood that it could be potentially beneficial to restrict delivery of the compounds of the invention to the target tissue or cell in which protein expression. It is also understood that it may be desirable to target the compounds of the invention to a desired tissue or cell type. The compounds of the invention may thus be coupled to a targeting moiety. The compounds of the invention may be coupled to a cell uptake moiety. The targeting moiety may also function as the cell uptake moiety.

PAX6 Mini-Promoters

The present invention herein provides novel PAX6 mini-promoter sequences that are capable of effecting transcriptional expression in a spatial and temporal fashion in the eye. Certain PAX6 mini-promoters of the invention comprise minimal PAX6 promoter elements joined in a non-native configuration, thus providing advantageous characteristics. Also provided are novel expression vector compositions comprising PAX6 mini-promoters, which allow consistent specific spatiotemporal transcription of expression sequences. Also provided are novel methods utilizing these PAX6 mini-promoters and expression vectors.

The PAX6 promoters of the invention, as described herein, are referred to as 'mini-promoters' to reflect the fact that the mini-promoters comprise minimal PAX6 promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance one or more human PAX6 regulatory elements corresponding to one or more of SEQ ID NO: 10-16, and the human PAX6 basal promoter element corresponding to SEQ ID NO: 8 or 9, or sequences with substantial functional and/or sequence equivalence, is altered. Additionally, the orientation of the different promoter elements may be altered—for instance the regulatory element corresponding to one or more of SEQ ID NO: 10-16 may be inverted relative to the basal promoter element corresponding to SEQ ID NO: 8 or 9. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that human PAX6 mini-promoters having a sequence corresponding to SEQ ID NO: 1-7, and which are comprised of human PAX6 regulatory elements (corresponding to SEQ ID NOs: 6-10) operably linked in a non-native conformation to a human PAX6 basal promoter having a nucleic acid sequence corresponding to SEQ ID NO: 8 or 9, is capable of directing expression of an expressible sequence which is operably linked downstream of the PAX6 promoter in specific cell types of the eye. The inventors have further demonstrated, as illustrated in the non-limiting Working Examples, that human PAX6 mini-promoters (SEQ ID NO: 18-21) are capable of directing expression of an expressible sequence that encodes the PAX6 protein in specific cell types of the eye. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provides for a transcription rate of an expressible sequence operably linked to a modified promoter sequence that is at least about 75% the transcription rate of the promoter sequence of SEQ ID NO: 1-7, at least about 80%, at least about 90%, at least about 95%, at least about 97%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1-7 that are not conserved may be deleted or substituted, usually modifications that retain the spacing between conserved sequences is preferred. In general, the spacing between the regulatory element and the basal promoter is not more than about 5 kb, generally not more than about 1 kb, usually not more than about 500 nt, and may be not more than about 100 nt, down to a direct joining of the two sequences.

In one embodiment of the invention, there is provided an isolated nucleic acid fragment comprising a PAX6 mini-promoter, wherein the PAX6 mini-promoter comprises one or more PAX6 regulatory elements operably linked in a non-native conformation to a PAX6 basal promoter. The PAX6 mini-promoter may have a nucleic acid sequence which is substantially similar in sequence and function to SEQ ID NO: 1-7. The PAX6 basal promoter may have a nucleic acid sequence which is substantially similar in sequence and function to SEQ ID NO: 8 or 9. The PAX6 regulatory element may have a nucleic acid sequence which is substantially similar in sequence and function to one or more of SEQ ID NO: 10-16, e.g. comprising one, two, three, four or five of the provided regulatory elements. The PAX6 mini-promoters may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expressible sequence may encode a PAX6 protein or an isoform or fragment thereof. In some embodiments of the invention, the expressible sequence may be a PAX6-derived cDNA or a PAX6-derived mini-gene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

It is an object of the present invention to provide means of expressing a gene, protein, RNA interference molecule or the like in a cell, tissue or organ. As such, the inventors thus provide novel expression vectors comprising PAX6 mini-promoters which are capable of accomplishing this task. In one embodiment, there is provided an expression vector comprising a PAX6 mini-promoter, wherein the PAX6 mini-promoter comprises one or more PAX6 regulatory element operably linked in a non-native conformation to a PAX6 basal promoter. The PAX6 mini-promoter may have a nucleic acid sequence which is substantially similar in sequence and function to SEQ ID NO: 1-7. The PAX6 basal promoter may have a nucleic acid sequence which is substantially similar in sequence and function to SEQ ID NO: 8 or 9. The PAX6 regulatory element may have a nucleic acid sequence which is substantially similar in sequence and function to one or more of SEQ ID NO: 10-16. The PAX6 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expressible sequence may encode a PAX6 protein or an isoform or fragment thereof. In some embodiments of the invention, the expressible sequence may be a PAX6-derived cDNA or a PAX6-derived minigene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21. The expression vector may further comprise a genomic targeting sequence. The inventors have herein demonstrated that expression vectors comprising novel PAX6 mini-promoter elements are capable of directing transcription of an expression sequence in specific cell types, for instance in ganglion cells in the retina (eye). In one embodiment of the invention, there is thus provided a method for expressing a gene, protein, RNA interference molecule or the like in a cell, the method comprising introducing into the cell an expression vector comprising a PAX6 mini-promoter element, wherein the PAX6 mini-promoter element comprises one or more PAX6 regulatory element operably linked in a non-native conformation to a PAX6 basal promoter element. Cells of interest include, without limitation, cells of the eye and progenitors thereof, e.g. retinal cells, retinal Müller glial cells ganglion cells, amacrine cells, horizontal cells, corneal cells etc. Cells of interest also include, without limitation, cells of the brain, spinal cord, pineal gland, lacrimal gland, teeth, gut, pancreas, etc., and progenitors thereof. The PAX6 mini-promoter may have a nucleic acid sequence which is substantially similar in sequence and function to SEQ ID NO: 1-7. The PAX6 basal promoter may have a nucleic acid sequence which is substantially similar in sequence and function to SEQ ID NO: 8 or 9. The PAX6 regulatory element may have a nucleic acid sequence which is substantially similar in sequence and function to one or more of SEQ ID NO: 10-16. The PAX6 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. In one embodiment, the expressible sequence may encode a PAX6 protein or an isoform or fragment thereof. In some embodiments of the invention, the expressible sequence may be a PAX6-derived cDNA or a PAX6-derived mini-gene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

In one embodiment of the invention, there is provided a method for identifying or labeling a cell, the method comprising introducing into the cell an expression vector comprising a PAX6 mini-promoter element, wherein the PAX6 mini-promoter element comprises one or more PAX6 regulatory elements operably linked in a non-native conformation to a PAX6 basal promoter element, and wherein the expressible sequence comprises a reporter gene. The PAX6 mini-promoter element may have a nucleic acid sequence substantially similar in sequence and function to SEQ ID NO: 1-7. The PAX6 basal promoter element may have a nucleic acid sequence substantially similar in sequence and function to SEQ ID NO: 8 or 9. The PAX6 regulatory element may have a nucleic acid sequence substantially similar in sequence and function to one or more of SEQ ID NO: 10-16. The inventors have demonstrated that expression vectors comprising certain human PAX6 promoter elements are capable of expression in specific regions of eye, most notably retinal ganglion cells, horizontal cells, amacrine, and Müller glia cells in the eye. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like. The expressible sequence may encode a PAX6 protein or an isoform or fragment thereof. In some embodiments of the invention, the expressible sequence may be a PAX6-derived cDNA or a PAX6- derived mini-gene. In one embodiment, the expressible sequence is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

In further embodiments of the invention, there is provided a method for monitoring or tracking the development or maturation of a cell, the method comprising: 1) introducing into the cell an expression vector comprising a PAX6 mini-promoter element operably linked to an expressible sequence, wherein the PAX6 mini-promoter element comprises one or more PAX6 regulatory elements operably linked in a non-native conformation to a PAX6 basal promoter element, and wherein the expressible sequence comprises a reporter gene; and 2) detecting the expression of the reporter gene in the cell of in progeny of the cell as a means of determining the lineage, identity or developmental state of the cell or cell progeny. The PAX6 mini-promoter element may have a nucleic acid sequence substantially similar in sequence and function to SEQ ID NO: 1-7. The PAX6 basal promoter element may have a nucleic acid sequence substantially similar in sequence and function to SEQ ID NO: 8 or 9. The PAX6 regulatory element may have a nucleic acid sequence substantially similar in sequence and function to one or more of SEQ ID NO: 10-16. In such a fashion, one may be able to follow the development of a parent cell as it differentiates into more mature cells. As an example, one could introduce an expression vector comprising the aforementioned PAX6 mini-promoter elements into a pluripotent stem cell, monitor the expression of the reporter gene that is being expressed by the PAX6 promoter elements during the maturation and differentiation of the stem cell and thus determine the state of maturation, for instance in the differentiation of the pluripotent stem cell into a specific retinal cell type. The inventors have demonstrated that the PAX6 mini-promoter elements described herein direct transcriptional expression in certain retinal cell types, and so detection of reporter gene expression in a cell would thus be indicative of the cellular identity of the cell as being a certain type of retinal cell.

The inventors have herein demonstrated that certain PAX6 mini-promoter elements of the present invention are capable of driving expression in retinal cells. This expression pattern provides additional methods of use for these mini-promoter elements. For instance, the PAX6 mini-promoters of the present invention can be utilized in a gene therapy or cell therapy application wherein the PAX6 mini-promoters are utilized to drive expression of a therapeutic or beneficial compound, such as a protein, in retinal cells. In such a way, the therapeutic or beneficial compound can be useful for a disease or condition that involves such retinal cells, or which may be improved by expression of the therapeutic or beneficial compound in those cells. In certain embodiments of the invention, there is thus provided a method of treatment of a subject having a disease or condition of the eye, the method comprising administering to the subject a therapeutically effective dose of a composition comprising a PAX6 mini-promoter element, wherein the PAX6 mini-promoter element comprises one or more PAX6 regulatory element operably linked in a non-native conformation to a PAX6 basal promoter element. The PAX6 mini-promoter element may have a nucleic acid sequence substantially similar in sequence and function to SEQ ID NO: 1-7. The PAX6 basal promoter element may have a nucleic acid sequence substantially similar in sequence and function to SEQ ID NO: 8 or 9. The PAX6 regulatory element may have a nucleic acid sequence substantially similar in sequence and function to one or more of SEQ ID NO: 10-16. The disease or condition may include retinal diseases, myopia, retinal degeneration, retinal damage, blindness, macular degeneration, retinitis pigmentosa, inherited retinal genetic diseases, dry eye syndrome, foveal hypoplasia, diabetic retinopathy, cone rod dystrophy, hypertensive/diabetic retinopathy, glaucoma, WAGR syndrome, WAGRO syndrome, chromosome 11p13 deletion syndrome, sjögrens syndrome, keratitis, coloboma, optic nerve hypoplasia, peters anomaly, ectopic pupillae, corneal dysplasia, corneal degeneration, corneal damage, lens dysplasia, lens degeneration, lens damage, or aniridia. The disease or condition may also include brain diseases, spinal cord diseases, intellectual disability, functional conductivity, autism, spinal cord disease, pineal gland disease, lacrimal gland disease, tooth disease, gastrointestinal disease, or diabetes. The therapeutic or beneficial compound may be a light-sensitive compound, for instance rhodopsin, channel rhodopsin, etc. In one embodiment, the therapeutic or beneficial compound may be a PAX6 protein or an isoform or fragment thereof. In some embodiments of the invention, the therapeutic or beneficial compound may be a PAX6-derived cDNA or a PAX6-derived mini-gene. In one embodiment, the therapeutic or beneficial compound is substantially similar in sequence and function to SEQ ID NO: 17. In other embodiments, the PAX6 mini-promoters that are operably linked to an expressible PAX6 sequence are substantially similar in sequence and function to SEQ ID NO: 18-21.

The inventors herein further describe the present invention by way of the following non-limiting examples:

EXAMPLES

Material and Methods

Chromatin interaction from Hi-C dataset. Publically available datasets for TADs (topologically associating domains) and Hi-C experiments using the restriction enzyme HindIII in mESC (mouse J1 embryonic stem cells), mouse cortex cells from eight-week old male C57BL/6NCrl mice, hESC (human H1 embryonic stem cells), and human IMR90 fibroblast cells were accessed to explore chromatin interactions at the PAX6 locus (Dixon, Selvaraj et al. 2012; Shen, Yue et al. 2012). Summary files from Gene Expression Omnibus (GSE35156), which listed paired-end reads mapped to mouse mm9 and human hg18 genome assemblies were retrieved. We mapped the genomic coordinates of TADs and paired-end reads, originally defined on the hg18 human assembly, onto the hg19 build using the liftOver tool provided by the UCSC Genome Browser. Reads from duplicated Hi-C datasets of the same cell type were combined. Numbers of paired-end reads linking each possible pair of 10-kb bins were counted, and each 10-kb bin was set to overlap with six kb of the bin that came before it. The datasets were plotted as two-dimensional heat maps using the R package, version 1.6.0, R version 3.0.2). (Servant, Lajoie et al. 2012)

Local Clustering Approach to Identify Highly Interactive Neighborhoods.

Highly interactive regions around PAX6 in all cells were identified through a local neighborhood clustering approach. A search was initiated from the PAX6 containing TAD of each corresponding cell type. In a sliding window analysis with each window containing 2n+1 of the 10-kb bins, where n is the number of bins extended from the center bin of each given window in both directions, we summed the total interactions for the 2n+1 consecutive bins. We determined the maximum interaction sum among all analyzed windows containing all PAX6 TSSs (as specified in UCSC Genes annotation), and reported the percentile of this observed sum relative to the distribution of all sums observed for all windows of the same size within the TAD. We report this percentile (0 to 100) as the interactive score. The procedure was repeated for n from five to 45 for each cell type, and the highly interactive neighborhood was defined as the window of size 2n+1 with the highest interactive score.

PAX6 transcription start sites. The promoter structure of PAX6 was delineated using capped 5' mRNA end positions determined from FANTOM5 CAGE (cap analysis gene expression) data (Forrest, Kawaji et al. 2014). PAX6 CAGE data was collected for all available human tissues using the ZENBU data explorer. The CAGE data was then manually curated to exclude reads from cancer cells and induced pluripotent stem cell experiments, generating the 'all human tissues' group. From the 'all human tissues' reads, the central nervous system tissues (excluding the neural retina) were selected and copied into the 'CNS tissues group', similarly reads from ocular tissues (including the neural retina) were selected and copied into 'Ocular tissues' group. The resulting 'CNS tissues' and 'Ocular tissues' groups contained mutually exclusive subsets of the 'All human tissues' group.

Computational prediction of regulatory regions. The regulatory potential of regions within the PAX6 regulatory domain (chr11:31616062-31848751 on the hg19 assembly) was computed using three combined criteria; conservation, ChIP-seq supported TFBS, and predicted regulatory regions from segmentation methods (Segway and ChromHMM) (Hoffman, Ernst et al. 2013). RPS (regulatory prediction scores) for these three criteria were computed by applying a 200 bp sliding window to the PAX6 highly interactive neighborhood with a step size of 100 bp (n=2,325). Each of the three criteria contributed a low, medium, or high RPS of 0, 0.5, or 1.0 respectively, for a maximum score of 3.0; details of the individual component scoring follow.

Conservation scores were computed using the 100 vertebrate phastCons data from the UCSC genome browser (Pollard, Hubisz et al. 2010). For each window the mean phastCons score was calculated. The low, medium, and high score thresholds were determined by taking the distribution of the mean phastCons scores for each of the 2,325 scoring windows and applying a Gaussian mixture model using the R statistics package (version 3.1.2) with the mixtools library. The data were consistent with two overlapping distributions. The right-hand distribution was consistent with selective pressure. The mean and standard deviation of this distribution was used to compute the score thresholds with a low, medium, and high RPS corresponding to mean phastCons scores 0.17, between 0.17 and 0.79, and >0.79 respectively.

Predicted TFBSs within ChIP-seq peaks were retrieved from the MANTA database (Mathelier, Lefebvre et al. 2015). Precisely, TFBS were defined by scanning the peaks from a set of 477 TF ChIP-seq experiments from ENCODE (ENCODE Project Consortium 2004)) and PAZAR (Portales-Casamar, Kirov et al. 2007) with the corresponding transcription factor binding profiles were retrieved from the JASPAR database of transcription factor binding site profiles (Portales-Casamar, Kirov et al. 2007; Portales-Casamar, Arenillas et al. 2009; Portales-Casamar, Thongjuea et al. 2010; Mathelier, Zhao et al. 2014). All positions within ChIP-seq peaks with a relative profile score ≥85% were recorded. The count of TFBS within each scoring window was used to assign the RPS. Windows with either no TFBS or more than 10 TFBS were assigned a low RPS. The rationale for the latter is based on the concept that too many binding sites are suggestive of non-specific binding properties (Worsley Hunt and Wasserman 2014). Windows with a count of one to five TFBS were assigned a medium RPS and windows with six to ten 10 TFBS were assigned a high RPS. Similar to the phastCons scoring method, the choice of threshold on the number of predicted TFBS used to assign low, medium, or high RPS was determined based on the distribution of the TFBS counts.

The combined Segway and ChromHMM segmentation data (Hoffman, Ernst et al. 2013) was obtained from the ENCODE project at UCSC. All segments within the PAX6 regulatory domain predicted to be either WE (weak enhancers), E (enhancers), PF (promoter flanking regions), or TSS were used. Windows overlapping at least one E or TSS element were assigned a high RPS. Windows overlapping at least one WE or PF element (but no E or TSS elements) were assigned a medium RPS, and windows with no overlapping elements received a low RPS. For each of six profiled cell types (GM12878, H1-hESC, HeLa-S3, HepG2, HUVEC and K562), the presence of enhancers, promoters, and TSSs were documented.

Cloning of the rAAV backbone and viral genomes. The expression cassette (EcoRI site, multiple cloning site, MluI Site, Ple251 MiniPromoter, AscI site, pCI (chimeric intron), NotI site, icre open reading frame (ORF), NotI site, AsiSI site, a mutant woodchuck hepatitis virus posttranscriptional regulatory element (WPRE) mut6 (Zanta-Boussif, Charrier et al. 2009) sequence, AsiSI site, SV40 poly-adenosine tail, and SalI site) was synthesized by (DNA2.0, Menlo Park, Calif.) and cloned into the EcoRI/SalI sites of P2393 (pEN-N.AAV.tMCK.Pl.flluc.bgh; University of Pennsylvania, Philadelphia, Pa.). An EmGFP ORF, sequence from Vivid Colors™pcDNA™6.2/N-emGFP-DEST (Life Technologies, Carlsbad, Calif.), was synthesised by DNA2.0 (Menlo Park, Calif.) with NotI sites on the 5' and 3' ends of the construct (Teerawanichpan, Hoffman et al. 2007). Icre was removed by NotI digest and EmGFP was ligated into the NotI sites to produce an rAAV backbone carrying the EmGFP reporter. Ple254 (SEQ ID NO: 1), Ple255 (SEQ ID NO: 2), Ple256 (SEQ ID NO: 3), Ple257 (SEQ ID NO: 4), Ple258 (SEQ ID NO: 5) and Ple260 (SEQ ID NO: 7) were synthesized (DNA2.0, Menlo Park, Calif.), and Ple259 (SEQ ID NO: 6) was synthesized (Integrated DNA Technologies, Coralville, Iowa), all with MluI and AscI restriction sites on the 5' and 3' ends respectively. The rAAV backbone and MiniPs were double digested with MluI and AscI, and the MiniPs were subsequently ligated into the rAAV backbone.

For cloning of the PAX6 MiniPromoters to drive the expression of PAX6, the rAAV backbone was produced as described above, and 3×FLAG/PAX6, flanked by NotI restriction sites, was synthesized (DNA2.0). Both the rAAV backbone and 3×FLAG/PAX6 were digested with NotI and subsequently ligated together. PAX6 MiniPromoters were synthesized as described above with FseI and AscI restriction sites flanking the sequence. Both the rAAV backbone and the PAX6 MiniPromoters were double digested with FseI and AscI and the MiniPromoters were subsequently ligated into the rAAV backbone.

Packaging of viral genomes into modified rAAV2. rAAV genome vector plasmids were packaged into a capsid variant of rAAV2. Packaging, purification, and the titre was measured as previously described (Zolotukhin, Potter et al. 2002; Jacobson, Acland et al. 2006). The virus was suspended in BSS (Balanced Salt Solution; Alcon Canada Inc., Mississauga, Canada)+0.014% tween 40 producing a minimum titre of $10^{13}$ viral genomes/mL (vg/mL) as determined by qPCR.

Packaging of viral genomes into rAAV9. rAAV backbones containing Ple254-3×FLAG/PAX6, Ple255-3×FLAG/PAX6, and Ple259-3×FLAG/PAX6 were packaged into rAAV9 at the Vector Core at the University of Pennsylvania (Philadelphia, Pa.).

Production of postnatal day 14 mice. Virus was injected into P14 B6129F1 hybrid mice generated by mating C57BL/6J (Jackson Laboratory, JAX Stock #000664, Bar Harbor, Me.) dams and 129S1/SvImJ (JAX Stock #002448) sires. Mating cages were monitored daily for newborn pups, starting 18 days after the dam and sire were setup. The day the pups were found was recorded as postnatal day 0. Mouse pups were then left undisturbed in the mating cage with their parents until the day of injection, P14.

Intravitreal injection of mouse pups. Virus was diluted to $8.22\times10^{12}$ vg/mL with BSS (Alcon Canada Inc., Mississauga, Canada) and further diluted to $5\times10^{12}$ vg/mL with BSS+0.05% Fast Green (Sigma Aldrich, Catalog # F7252-5G, St. Louis, Mo.). For each injection, five μL of virus was loaded into a BD Ultra-Fine II insulin syringe (Becton Dickinson, Catalog #328289, Franklin Lakes, N.J.). P14 mice were anesthetized with isoflurane and placed under a dissecting microscope. The right eye was covered in Refresh Lacri-lube (Allergen, Dublin, Ireland) and the left eye was washed with Eye Stream (Alcon Canada Inc., Mississauga, Canada) and treated with one or two drops of Alcaine Eye Drops (Alcon Canada Inc., Mississauga, Canada). Next a BD 26G3/8 hypodermic needle (Becton Dickinson Cat #305110, Franklin Lakes, N.J.) was used to make an aperture through the conjunctiva adjacent to the limbus on the nasal side of the eye. Finally, the insulin syringe was inserted through the sclera on the temporal side of the eye, into the intravitreal space, and five μL of rAAV solution ($5\times10^{12}$ vg/mL) was administered.

Intravenous rAAV Administration. rAAV9 Ple254-3×FLAG/PAX6 WPRE and rAAV Ple255-3×FLAG/PAX6 were administered by intravenous injection into post natal day 4 mice. For intravenous injections, viruses were diluted to $1\times10^{13}$ vg/ml in phosphate-buffered saline +0.05% Fast Green (Sigma Aldrich) and 50 μl were injected into the superficial temporal vein using a 30-gauge needle and 1 cc syringe. Mouse pups were then tattooed for identification and returned to their cage.

Tissue harvesting, sectioning, and fluorescent antibody staining. Eyes were collected 40 days post injection, fixed in four percent paraformaldehyde for two hours at four ° C., rinsed with phosphate buffer (pH 7.4) and dehydrated in 25% sucrose overnight at four ° C. Eyes were embedded in Tissue-Tek O.C.T. compound (Sakura Finetek, Catalog #4583, Torrance, Calif.) and 16 μm sections were cut with a Microm HM550 cryostat (Thermo Scientific, Waltham, Mass.). Sections were blocked for 30 minutes at room temperature in 10% BSA (Bovine Serum Albumin; Sigma Aldrich, Catalog # A7906-100G, St. Louis, Mo.)+0.3% Triton X-100 (Sigma Aldrich, Catalog # T8787-250ML, St. Louis, Mo.). Once blocked, sections were incubated in primary antibody stain (GFP antibody (1:100; AYES, Catalog # GFP-1020, Tigard, Oreg.), PAX6 antibody (1:100; Covance Cat # PRB-278P, Princeton, N.J.), FLAG antibody (1:100; Sigma-Aldrich Catalog # F1804), Brn3 antibody (1:100; Santa Cruz Biotechnology Catalog # sc-28595, Dallas, Tex.), Syntaxin 1 antibody (1:100; Sigma-Aldrich Catalog # S0664, St. Louis, Mo.), Calbindin antibody (1:100; Sigma-Aldrich Catalog # C9848, St. Louis, Mo.), or SOX9 (1:100; Millipore, Catalog # ABE571, Billerica, Mass.) in phosphate buffer containing 2.5% BSA with 0.1% Triton X-100) at room temperature for two hours. Next, sections were rinsed three times for five minutes each in phosphate buffer and stained with a secondary antibody (either Alexa594 conjugated goat anti-rabbit immunoglobulin, Alexa594 conjugated goat anti-mouse immunoglobulin, Alexa484 conjugated goat anti-mouse immunoglobulin, Alexa594 conjugated goat anti-rabbit immunoglobulin or Alexa488 conjugated goat anti-chicken immunoglobulin (1:1000; Molecular Probes Catalog numbers A-11012, A-11005, A11029 & A-11012 and A-11039 respectively, Eugene, Oreg.)) and counter stained with Hoechst (1:000 from two μg/mL, Sigma-Aldrich Cat #881405, St. Louis, Mo.) for one hour at RT. Sections were given three five-minute washes and were mounted with ProLong Gold Antifade Mountant (Life Technologies, Catalog # P36930, Carlsbad, Calif.). Sections were imaged on a Bx61 Microscope (Olympus America Inc., Centre Valley, Pa.) using cellSens software (Olympus America Inc., Centre Valley, Pa.). Raw image files were converted to composite TIFF (tagged image file format) files using imageJ software with the Bio-Formats plugin. Images were imported and the multichannel images were exported as composite, or single color, TIFF images. To produce images with only partial blue and green overlay (MiniPromoter overview images) both a blue green composite TIFF, and a single green channel image TIFF, from the same source image were produced. The images were then aligned with the composite image arranged above the single channel image. A clipping mask was then applied to crop the blue and green composite image so that it was only visible along the leftmost boarder of the green image.

EXAMPLES

Example 1: Bioinformatic Analysis of the PAX6 Locus

Figure 1:
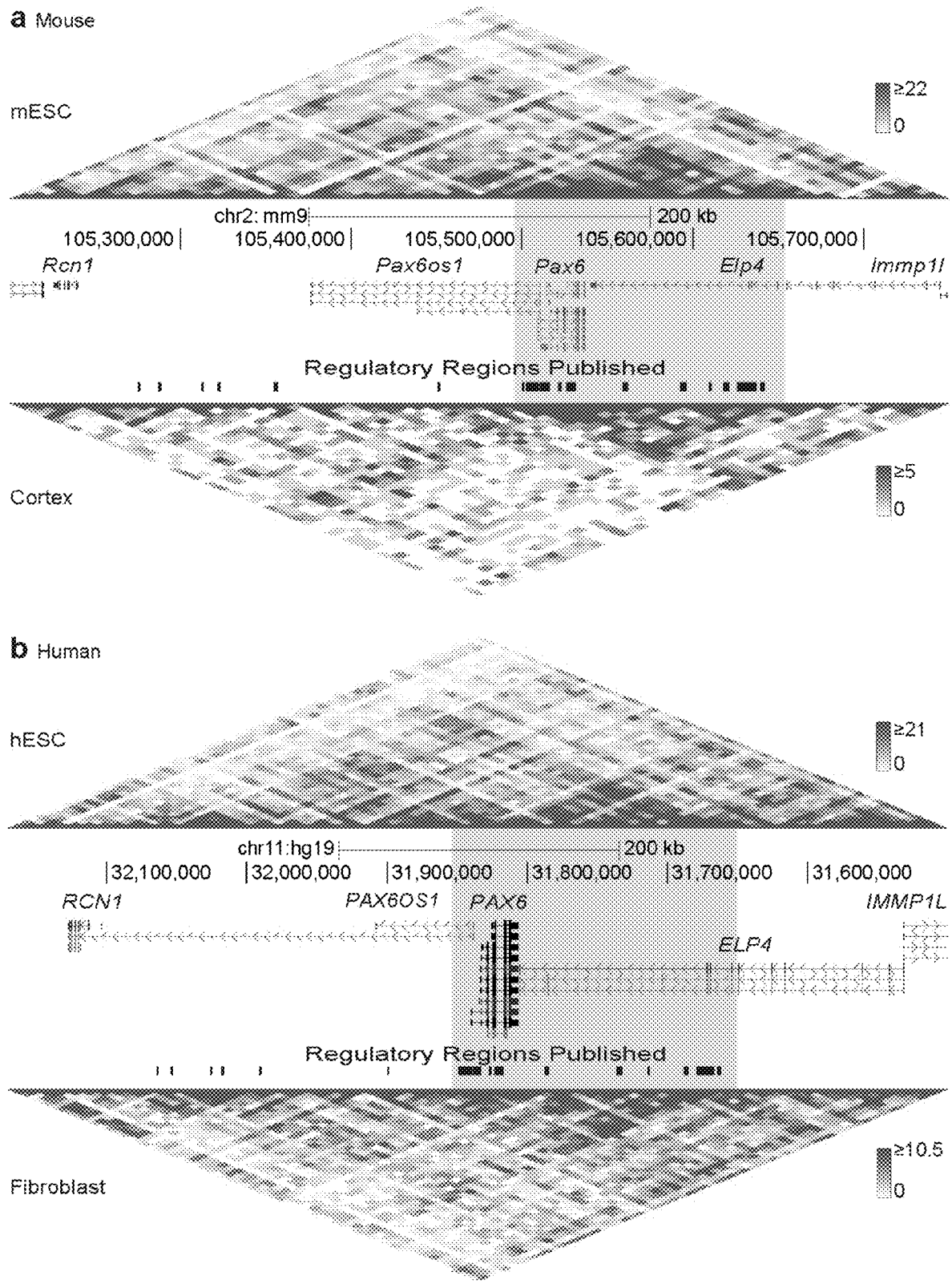
FIG. 1. A PAX6 containing highly-interactive regulatory neighborhood, encompassing the majority of previously published PAX6 regulatory regions, is revealed by mouse and human chromosome interaction data. TADs (topologically associating domains) and Hi-C(high-throughput chromosome capture) data are indicative of interactions between distal RRs (regulatory regions) and promoters. Presented are two-dimensional heatmap visualizations of previously published Hi-C chromatin interaction datasets (Dixon, Selvaraj et al. 2012; Shen, Yue et al. 2012). The interaction strength is indicated by color, ranging from red (set as 90th percentile of counts) to white (no observed interactions). These values correspond to the number of interacting segments observed in the DNA sequences for pairings of 10-kb bins. A PAX6 containing highly-interactive regulatory neighborhood computed from mouse cortex cells is highlighted in orange. Gene transcripts are indicated in blue and the "Regulatory Regions Published" displays our curation of all previously published PAX6 RRs as black rectangles. (a) Visualization of datasets from mouse cells: top, mESC (mouse embryonic stem cell) line J1; bottom, adult C57BL/6NCrl mouse cortex. The 90th percentile is 22 and five counts for mESC and cortex respectively. The displayed segment corresponds to 105,200,001-105,750,000 on Chromosome 2, mm9 assembly. (b) Visualization of datasets from human cells: top, hESC (human embryonic stem cell) line H1; bottom, human fibroblast cell line IMR90. The 90th percentile is 21 and 10.5 counts for hESC and IMR90 respectively. The position of the human PAX6 containing highly-interactive regulatory neighborhood is matched by position using the lift-over function of the UCSC Genome Browser to the region defined in mice. The displayed segment corresponds to 32,170,000-31,500,001 on Chromosome 11, hg19 assembly.

TADs, which are sub-regions of chromosomes defined by an elevated frequency of intra-regional DNA-DNA interactions in Hi-C experiments, were examined from mESCs, mouse cortex cells, hESCs, and a human IMR90 fibroblast cell line (Dixon, Selvaraj et al. 2012; Shen, Yue et al. 2012). All 39 published RRs of PAX6 are situated within the PAX6-containing TAD in all cell types examined (FIG. 1). We then developed a local clustering approach to search for highly interactive neighborhoods. This revealed that within the PAX6-containing TAD, there is a highly-interactive regulatory neighborhood containing all the PAX6 TSSs (transcription start sites). Although Pax6 expression is not high in mouse cortex cells and is supressed in mESCs (Kaspil, Chapnik et al. 2013), this highly-interactive regulatory neighborhood overlapped almost perfectly between the two cell types (FIG. 1a; mm9 coordinates: chr2: 105495781-105653515 for mouse cortex cells at 99.7 percentile and chr2:105501001-105652563 for the mESCs at 99.6 percentile). Lifting over the genomic coordinates of the regulatory neighborhood from mouse mm9 to the human hg19 genome assembly (FIG. 1b), it was revealed that the mouse regulatory neighborhood overlapped with the highly-interactive regulatory neighborhood similarly identified in the human data (overlaps of 98.7 and 100 percent for hESCs and the IMR90 fibroblast cell line respectively). Spanning from the 5' end of Pax6os1 to the last four exons of Elp4 on the 3' end, the <160 kb Pax6 highly-interactive regulatory neighborhood overlaps with 33 (85%) previously published RRs. The rest of published RRs (15%) were located within a weaker interacting region situated between Pax6 and the Rcn1 promoter (FIG. 1).

The PAX6 exon structure was defined using the 10 different PAX6 transcripts reported in UCSC (hg19 assembly), which had also been presented by at least one of the following resources: Protein Data Bank, RefSeq, SwissProt, or CODS (FIG. 9a). This complexity is the product of alternative splicing and the use of multiple promoters (Xu, Zhang et al. 1999). CAGE data from the FANTOM5 consortium supports a three-promoter model for PAX6, with transcription being driven from P0, P1, and Pa (FIG. 9b) (Forrest, Kawaji et al. 2014). Interestingly, this CAGE data does not indicated the existence of a promoter P4 (Kleinjan, Seawright et al. 2004). For this analysis, the CAGE data was curated into three groups, after cancer and induced pluripotent stem cell reads were removed, producing: 'All human tissues', 'CNS tissues', and 'ocular tissues' groupings. The all human tissues group contains all of the data presented in the other two groups, while the CNS and ocular tissues groups are mutually exclusive. Interestingly, in the 'all humans tissues' group (Forrest, Kawaji et al. 2014), PAX6 expression was predominantly driven by promoter P1, with P0 initiating proportionally fewer transcripts, and Pa only producing a small minority of the transcripts, which failed to exceed baseline in the CNS tissues. Additionally, while the transcripts initiated by P0 and Pa start from focused TSSs, the transcripts initiated by P1 appear to originate from a range of TSSs spanning more than 300 bp. Combining the 10 mRNA transcripts with TSSs results in a complex model of PAX6 where each promoter drives at least two different isoforms of the mRNA (FIG. 9c).

Figure 2:
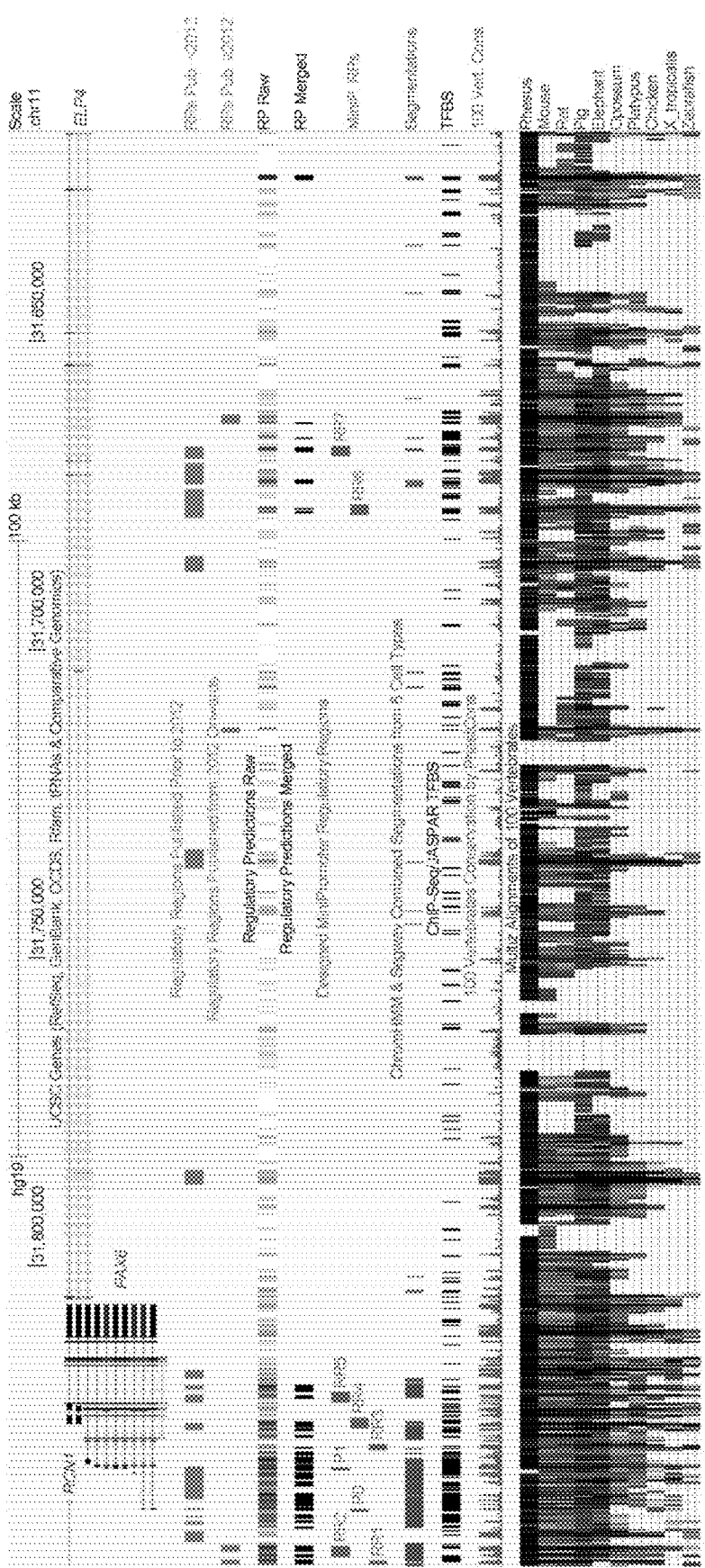
FIG. 2. Bioinformatic analysis of the PAX6 containing highly-interactive regulatory neighborhood revealed 31 putative RRs (regulatory regions). Visualization of the data used to predict RRs within the highly-interactive regulatory neighborhood (Chr11: 31,848, 751-31,616,062, hg19) specified in FIG. 1. Tracks are described from top of figure to bottom. Transcripts are displayed, with black having a higher validation level than grey (details in FIG. 9). Orange rectangles in the RRs Pub tracks denote RRs manually curated from the scientific literature separated into those available prior to (pre-2012) and post experimental design (2012-December 2015). White and black vertical lines in the RP (regulatory prediction) Raw track indicate low to high scoring regions respectively. Black rectangles in the RP Merged track represent high scoring regions 2.0) that were merged into 31 predicted RRs. Green rectangles in the Mini-Promoter RRs track represent the 12 RRs selected and manually refined to produce nine RRs for testing in Mini-Promoters; RR1-RR7 (SEQ ID NO: 10-16) and promoters P0 and P1 (SEQ ID NO: 8 and 9). Data used for the RP included predicted classifications from the ChromHMM and Segway segmentation tools (red, promoter region including transcription start site(s); blue, enhancer; azure, weak enhancer or open chromatin cis regulatory element; orange, predicted promoter flanking region), ChIP-seq-supported transcription factor binding sites (TFBS, black rectangles), and phastCons conservation scores based on 100 vertebrate genomes (green histogram). Genome sequence similarity plots for a hand-selected set of 10 species are displayed.

An initial literature and database assessment was conducted for PAX6, and entries were created for the human and mouse genes in the Transcription Factor Encyclopedia, and deposited regulatory data in PAZAR. A computational approach was developed to predict regulatory regions within the highly-interactive regulatory neighborhood at PAX6. In brief, regulatory potential was computed using three combined criteria; conservation, ChIP-seq supported TFBS, and predicted regulatory regions from segmentation methods (Segway and ChromHMM) (Hoffman, Ernst et al. 2013). RPS (regulatory prediction scores) for these three criteria were computed by applying a 200 bp sliding window to the PAX6 highly interactive neighborhood. Each of the three criteria contributed a low, medium, or high RPS of 0, 0.5, or 1.0 respectively, for a maximum score of 3.0 (FIG. 2). All overlapping and immediately adjacent (book-ended) windows with scores two were merged, which produced 31 RRs predicted to have high regulatory potential (FIG. 10). Of the 31 regions, 19 overlap with one or more previously published regulatory elements.

Example 2: Seven PAX6 MiniPromoters were Constructed from Nine Bioinformatically Predicted RRs Of the 31 predicted RRs, nine were hand selected to be tested as components of Mini-Promoters. For this work, RRs with known biological function as established in transgenic mice were considered, however as our system explores expression from a viral genome, regions with a breadth of supporting data were preferred. However, RRs overlapping with elements such as the pancreatic enhancer, repressor element, CNS element, CE2, and HS5+ were excluded from selection if they overlapped with previously published RRs that drive expression only during development, or exclusively outside of the retina (Kammandel, Chowdhury et al. 1999; Wu, Li et al. 2006; Zhang, Rowan et al. 2006; McBride, Buckle et al. 2011). Conversely, RRs overlapping with regions that have been previously shown to drive expression in the adult retina were favoured producing: P0 (SEQ ID NO: 8) and P1 (SEQ ID NO:9) which overlap with promoters 0 and 1 respectively (Xu and Saunders 1997; Xu, Zhang et al. 1999); RR4 with promoter a, the neural retina enhancer, a promoter a enhancer, and ele4H (Xu and Saunders 1998; Kammandel, Chowdhury et al. 1999; Xu, Zhang et al. 1999); RR5 with CE1 (Kleinjan, Seawright et al. 2004); RR6 with HS234Z (Kleinjan, Seawright et al. 2001); and RR7 with HS6 (McBride, Buckle et al. 2011) (FIG. 10). Three RRs (RR2 (SEQ ID NO: 11), RR5 (SEQ ID NO: 14), and RR6 (SEQ ID NO: 15)) were formed by connecting two high scoring RRs with the small (500 bp) highly conserved sequence between them. The final sequence of P0 (SEQ ID NO: 8) was determined by first aligning a previously described P0 sequence from mice to the human genome, and then trimming it down to 454 bp based on conservation (Baumer, Marquardt et al. 2002). A core promoter based on 454 bp of the sequence of P1 (SEQ ID NO: 9) was designed by lengthening a smaller, previously tested, promoter sequence (Zheng, Zhou et al. 2001). The 3' end was extended to just before the 3' end of exon one, and the 5' end was extended to reach the final size of 454 bp.

Figure 3:
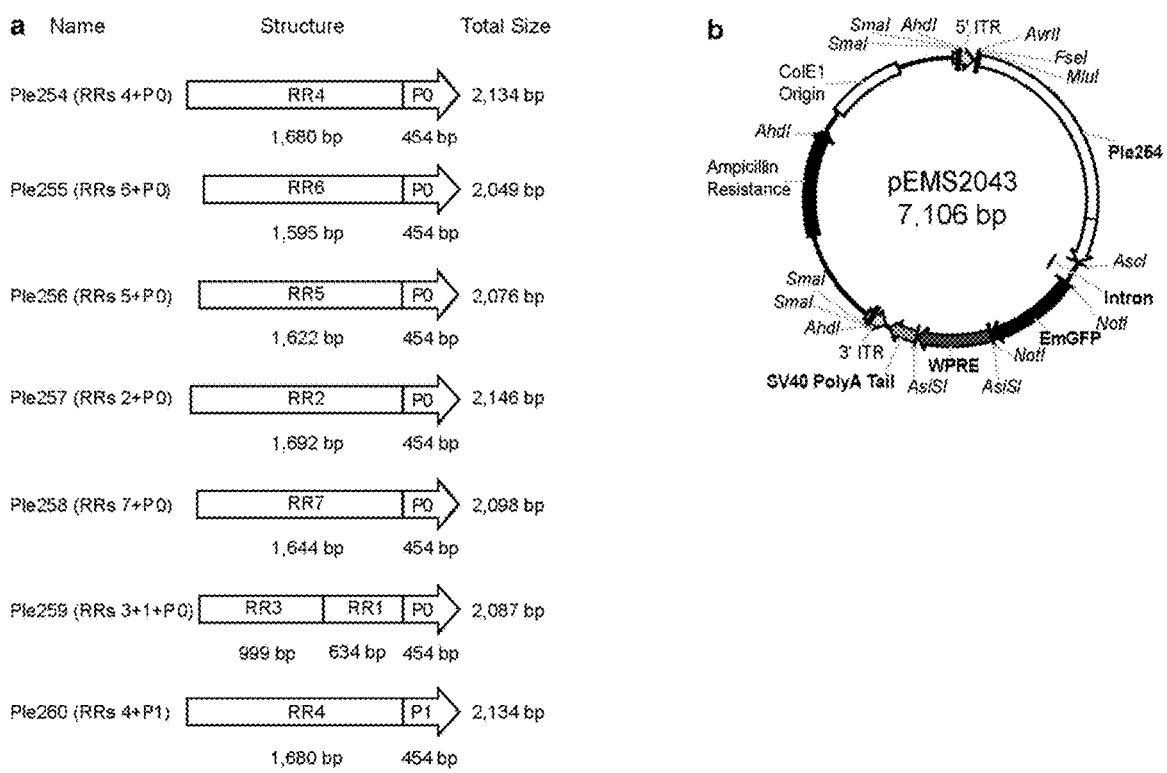
FIG. 3. PAX6 Mini-Promoters were cloned into a custom rAAV genome. (a) Seven Mini-Promoters, named Ple254-Ple260 (SEQ ID NOs: 1-7), were designed by concatenating seven hand selected RRs (regulatory regions) with either the P0 (SEQ ID NO:8) or P1 (SEQ ID NO: 9) core promoter sequence. Ple254 (SEQ ID NO: 1) and Ple260 (SEQ ID NO: 7) are related in that they both contain RR4, but differ in that they contain P0 (SEQ ID NO: 8) and P1 (SEQ ID NO:9) respectively. (b) Custom rAAV plasmid backbone streamlined assembly of viral genomes. A representative viral genome (pEMS2043) contains a 5' ITR (inverted terminal repeat; light grey arrow pointing clockwise) restriction sites (AvrII, FseI, MiuI, and AscI), a representative MiniPromoter (Ple254; white arrow with black outline), chimeric intron, EmGFP (Emerald GFP) reporter ORF (black arrow) flanked by NotI sites (the 5' NotI site forms a Kozak sequence with the 5' end of the reporter construct), WPRE (Woodchuck Hepatitis Virus Posttranscriptional Regulatory Element; dark grey arrow) flanked by AsiSI restriction sites, and a 3'

Since the viral packaging size of rAAV is only ~4.9 kb, the maximum size of a PAX6 MiniPromoter was set at 2.15 kb for this study, leaving room in the rAAV genome for reporter constructs such as EmGFP (Emerald GFP, 720 bp) and other elements such WPRE (woodchuck hepatitis virus posttranscriptional regulatory element, 587 bp) a poly adenosine tail (222 bp), and ITRs (inverted terminal repeats). Subtracting 454 bp for the core promoter RR included in each MiniPromoter, 1,696 bp was reserved for each of the seven remaining RRs. Taking conservation into consideration, the size of each RR was maximized to provide the best chance of capturing important regulatory sequences. The final sequence of each Mini-Promoter contains at least one of RR1-RR7 (SEQ ID NO: 10-16) and either P0 (SEQ ID NO: 8) or P1 (SEQ ID NO: 9) (FIG. 3a).

FIG. 11 provides a detailed overview of the promoter and regulatory regions selected for the design of Ple254 (SEQ ID NO: 1), Ple255 (SEQ ID NO: 2), Ple259 (SEQ ID NO: 6) and Ple260 (SEQ ID NO: 7). The Mini-Promoter design is based, in part, on the identification of regions of conservation between the human genome and the mouse homolog (as shown in FIG. 12) and Table 1 provides a list of the conserved regions within the Ple254 Mini-Promoter (SEQ ID NO: 1).

Table 1. List of conserved regions in the human PAX6-based MiniPromoter Ple254 (SEQ ID NO: 1). The "start" and "end" coordinates of the regions are relative to the full sequence of the MiniPromoter. "SEQ ID NO" denotes the encompassing regulatory element or basal promoter of each conserved region in the MiniPromoter. Conservation is determined by alignment of the human sequences and their mouse homologs using a threshold on the percentage of identity of 70%. Overall, about 54% of the MiniPromoter sequence is conserved between human and mouse.

| Start (relative to SEQ ID NO: 1) | End (relative to SEQ ID NO: 1) | Invariant sequence type | Encompassing SEQ ID NO |
|---|---|---|---|
| 533 | 653 | Conserved sequence | 13 |
| 685 | 898 | Conserved sequence | 13 |

-continued

| Start (relative to SEQ ID NO: 1) | End (relative to SEQ ID NO: 1) | Invariant sequence type | Encompassing SEQ ID NO |
|---|---|---|---|
| 945 | 1525 | Conserved sequence | 13 |
| 1681 | 1906 | Conserved sequence | 8 |

The Mini-Promoter design is also dependent on the identification and selection of DNA regions that are likely to contribute to the regulation of the transcriptional activity of a promoter. For the design of Ple254 (SEQ ID NO: 1), the selection of the basal promoter (SEQ ID NO: 8) and regulatory region (SEQ ID NO: 13) involved an analysis of each region for transcription start sites and transcription factor binding sites as shown in FIGS. 13 and 17.

Table 2 provides a list of the conserved regions within the Ple255 Mini-Promoter (SEQ ID NO: 2) and FIGS. 13 and 18 provide a detailed analysis of the regions within the promoter and regulatory regions that are involved in the functional activity of the Mini-Promoter.

Table 2. List of conserved regions in the human PAX6-based MiniPromoter Ple255 (SEQ ID NO: 2). The "start" and "end" coordinates of the regions are relative to the full sequence of the MiniPromoter. "SEQ ID NO" denotes the encompassing regulatory element or basal promoter of each conserved region in the MiniPromoter. Conservation is determined by alignment of the human sequences and their mouse homologs using a threshold on the percentage of identity of 70%. Overall, about 82% of the MiniPromoter sequence is conserved between human and mouse.

| Start (relative to SEQ ID NO: 2) | End (relative to SEQ ID NO: 2) | Invariant sequence type | Encompassing SEQ ID NO |
|---|---|---|---|
| 21 | 126 | Conserved sequence | 15 |
| 163 | 1432 | Conserved sequence | 15 |
| 1509 | 1595 | Conserved sequence | 15 |
| 1596 | 1821 | Conserved sequence | 8 |

Table 3 provides a list of the conserved regions within the Ple259 Mini-Promoter (SEQ ID NO: 6) and FIGS. 13, 15 and 16 provide a detailed analysis of the regions within the promoter and regulatory regions that are involved in the functional activity of the Mini-Promoter.

Table 3. List of conserved regions in the human PAX6-based MiniPromoter Ple259 (SEQ ID NO: 6). The "start" and "end" coordinates of the regions are relative to the full sequence of the MiniPromoter. "SEQ ID NO" denotes the encompassing regulatory element or basal promoter of each conserved region in the MiniPromoter. Conservation is determined by alignment of the human sequences and their mouse homologs using a threshold on the percentage of identity of 70%. Overall, about 75% of the MiniPromoter sequence is conserved between human and mouse.

| Start (relative to SEQ ID NO: 6) | End (relative to SEQ ID NO: 6) | Invariant sequence type | Encompassing SEQ ID NO |
|---|---|---|---|
| 95 | 393 | Conserved sequence | 12 |
| 465 | 744 | Conserved sequence | 12 |
| 779 | 901 | Conserved sequence | 12 |
| 1000 | 1633 | Conserved sequence | 10 |
| 1634 | 1859 | Conserved sequence | 8 |

Table 4 provides a list of the conserved regions within the Ple260 Mini-Promoter (SEQ ID NO: 7) and FIGS. 14 and 17 provide a detailed analysis of the regions within the promoter and regulatory regions that are involved in the functional activity of the Mini-Promoter.

Table 4. List of conserved regions in the human PAX6-based MiniPromoter Ple260 (SEQ ID NO: 7). The "start" and "end" coordinates of the regions are relative to the full sequence of the MiniPromoter. "SEQ ID NO" denotes the encompassing regulatory element or basal promoter of each conserved region in the MiniPromoter. Conservation is determined by alignment of the human sequences and their mouse homologs using a threshold on the percentage of identity of 70%. Overall, about 64% of the MiniPromoter sequence is conserved between human and mouse.

| Start (relative to SEQ ID NO: 7) | End (relative to SEQ ID NO: 7) | Invariant sequence type | Encompassing SEQ ID NO |
|---|---|---|---|
| 533 | 653 | Conserved sequence | 13 |
| 685 | 898 | Conserved sequence | 13 |
| 945 | 1525 | Conserved sequence | 13 |
| 1681 | 2134 | Conserved sequence | 9 |

Example 3: PAX6 Mini-Promoters Drive EmGFP Expression in PAX6 Expressing Cells

Seven Mini-Promoters were synthesized and cloned into an rAAV genome containing a chimeric intron, EmGFP reporter, WPRE mut6 (Zanta-Boussif, Charrier et al. 2009), SV40 sequence, and AAV2 ITRs (FIG. 3*b*). The viral genomes were packaged into modified rAAV2 and administered by intravitreal injection into P14 (postnatal day 14) mice, resulting in the detection of EmGFP expression driven from all seven Mini-Promoters (FIG. 4). Four Mini-Promoters (Ple254 (SEQ ID NO: 1), Ple255 (SEQ ID NO: 2), Ple259 (SEQ ID NO: 6) and Ple260 (SEQ ID NO: 7) drive consistent expression in the inner nuclear and ganglion cell layers of the adult mouse retina. Images of the same Mini-Promoter presented in FIGS. 4 and 5 come from different mice, and are representative of at least four of the five eyes injected per construct. Co-localization of GFP and PAX6 immunofluorescent staining suggested that, after intravitreal injection, Ple254 (SEQ ID NO: 1), Ple255 (SEQ ID NO:2), Ple259 (SEQ ID NO:6) and Ple260 (SEQ ID NO:7) drive EmGFP expression in patterns that overlap with the expression of PAX6 in the adult mouse retina (FIG. 5). More specifically, co-localization of GFP immunofluorescent staining with the ganglion cell marker Brn3a and the amacrine cell marker syntaxin reveals that Ple254 (SEQ ID NO: 1), Ple255 (SEQ ID NO:2), Ple259 (SEQ ID NO:6) and Ple260 (SEQ ID NO:7) drive expression in ganglion and amacrine cells, cell types that endogenously express PAX6 (FIGS. 6, 7, and 8). Furthermore, co-localization of GFP immunofluorescent staining with the horizontal cell marker calbindin, and the Müller glia marker Sox9, confirm Ple255 (SEQ ID NO: 2) drives expression in horizontal cells (FIG. 7) and Ple259 (SEQ ID NO: 6) drives expression in Müller glia, both cell types that endogenously express PAX6 (FIG. 8).

Example 4: PAX6 Mini-Promoters Drive PAX6 Expression in the Eye

Four of the PAX6 Mini-Promoters [Ple254 (SEQ ID NO: 1), Ple255 (SEQ ID NO: 2), Ple259 (SEQ ID NO: 6), and Ple260 (SEQ ID NO: 7)] were recloned to drive a 3×FLAG tag fused to the N-terminal of PAX6 as shown in FIG. 19. These cloning efforts resulted in four new constructs; Ple254-3×FLAG/PAX6 (SEQ ID NO: 18), Ple255-3×FLAG/PAX6 (SEQ ID NO: 19), Ple259-3×FLAG/PAX6 (SEQ ID NO: 20) and Ple260-3×FLAG/PAX6 (SEQ ID NO: 21). The constructs were cloned into viral backbones and backbones containing Ple254-3×FLAG/PAX6 (SEQ ID NO: 18), Ple255-3×FLAG/PAX6 (SEQ ID NO: 19) and Ple259-3×FLAG/PAX6 (SEQ ID NO: 20) were packaged into rAAV9 and then injected intravenously into post natal day 4 mice. As shown in FIG. 20, the Ple254 Mini-Promoter, the Ple255 Mini-Promoter and the Ple259 Mini-Promoter all drove the 3×FLAG/PAX6 expression in the adult mouse retina with staining in the ganglion cell layer (GCL) and inner nuclear layer (INL) as detected by the immunofluorescent co-labeling of PAX6 and the FLAG tag.

DISCUSSION

A highly-interacting local neighborhood at the PAX6 locus defined the search area for predicting regulatory regions. Chromatin interaction data has been shown to reflect the degree of interaction between pairs of fragments in the genome, including that of promoter and regulatory regions (Sanyal, Lajoie et al. 2012). Using public Hi-C datasets for mouse and human cells, we found all previously published regulatory regions that drive the endogenous expression of PAX6 to be within the PAX6-containing TADs in all four cell types examined. The identification of a highly-interactive regulatory neighborhood encompassing the PAX6 locus narrowed our focus to a region that contains 85% of the previously described PAX6 RRs. This indicated an association between 3D proximity and regulatory targets, which further supports the potential application of chromatin interaction data in guiding the identification of novel regulatory regions of PAX6. Thus, we used the boundaries of highly-interactive regulatory neighborhood to focus our bioinformatics work, within which we predicted RRs for use in PAX6 MiniPromoter development.

PAX6 promoter analysis supported selection of P0 as the core promoter for MiniPromoter development. CAGE data from the FANTOM5 consortium supports a three-promoter model of PAX6. In choosing amongst the PAX6 core promoters, the CAGE data revealed that P1 dominates transcript initiation in both the CNS and ocular tissues examined. However, it was also noted that P1 initiates transcription over a 300 bp region, raising concerns regarding the size of the promoter region that would be needed. To test this, we defined a small P1 promoter (SEQ ID NO: 9) and tested it successfully in Ple260 (SEQ ID NO: 7). At P0, the CAGE data revealed less, but clearly present, transcription initiation in the relevant tissues, which was focal. In addition, a core mouse promoter had previously been used from this site. In combination with the a enhancer, this P0 mouse core promoter was found to drive expression in the retina of postnatal day 20 mice (Zheng, Zhou et al. 2001; Baumer, Marquardt et al. 2002). Thus, we conservatively chose and successfully defined a small human P0 promoter (SEQ ID NO: 8) in Ple254 (SEQ ID NO: 1), Ple255 (SEQ ID NO: 2), and Ple259 (SEQ ID NO: 6).

Bioinformatic analysis recapitulated and refined previously published PAX6 RRs. We used computational tools such as Hi-C chromatin capture, ENCODE, and FANTOM5 data sets to explore and evaluate the PAX6 locus (Portales-Casamar, Swanson et al. 2010; Hoffman, Ernst et al. 2013; Andersson, Gebhard et al. 2014). Using the highly-interactive regulatory neighborhood as a guide, we predicted regulatory regions for PAX6 employing three criteria: conservation, TFBS, and predicted sequence classification (combined Segway and ChromHMM segmentation). This approach, while highlighting previously reported RRs such as CE1 and HS234Z, also revealed new potential RRs for future investigation (Xu and Saunders 1997; Kleinjan, Seawright et al. 2001; Kleinjan, Seawright et al. 2004). Pre-empting some of this work, it has been reported recently that sequencing of the Pax6 loci in elephant sharks revealed new RRs such as agCNE9 and agCNE11 which overlap with RR1 and RR2 respectively (Ravi, Bhatia et al. 2013). This combined bioinformatics approach has potential for predicting regulatory elements to gain a deeper insight into how other genes are regulated, or to guide the design of other tissue- and cell-type specific Mini-Promoters.

Four PAX6 Mini-Promoters drive consistent EmGFP expression from rAAV when delivered intravitreally, which overlaps with PAX6 expression in the adult mouse retina. Of the seven PAX6 Mini-Promoters, Ple255 (SEQ ID NO: 1) and Ple259 (SEQ ID NO: 6) are particularly interesting in that they are more 'PAX6-like', each capturing three of the four cell types that express PAX6, and together capturing the entirety of PAX6 expression in the adult mouse retina. Consequently, the promoters are attractive candidates for future optimization to capture the entire adult retinal expression pattern of PAX6, and for use in driving PAX6 expression in pre-clinical gene therapy trials for aniridia.

REFERENCES

Andersson, R., C. Gebhard, et al. (2014). "An atlas of active enhancers across human cell types and tissues." Nature 507(7493): 455-461.

Bainbridge, J. W., M. S. Mehat, et al. (2015). "Long-term effect of gene therapy on Leber's congenital amaurosis." N Engl J Med 372(20): 1887-1897.

Baumer, N., T. Marquardt, et al. (2002). "Pax6 is required for establishing naso-temporal and dorsal characteristics of the optic vesicle." Development 129(19): 4535-4545.

Bronson, S. K., E. G. Plaehn, et al. (1996). "Single-copy transgenic mice with chosen-site integration." Proc Natl Acad Sci USA 93(17): 9067-9072.

Chow, R. L., C. R. Altmann, et al. (1999). "Pax6 induces ectopic eyes in a vertebrate." Development 126(19): 4213-4222.

Cvekl, A. and P. Callaerts (2016). "PAX6: 25th anniversary and more to learn." Exp Eye Res 25(16): 30090-30092.

de Leeuw, C. N., F. M. Dyka, et al. (2014). "Targeted CNS delivery using human Mini Promoters and demonstrated compatibility with adeno-associated viral vectors." Molecular Therapy—Methods & Clinical Development 1(5): 1-15.

Dixon, J. R., S. Selvaraj, et al. (2012). "Topological domains in mammalian genomes identified by analysis of chromatin interactions." Nature 485(7398): 376-380.

ENCODE Project Consortium (2004). "The ENCODE (ENCyclopedia Of DNA Elements) Project." Science 306 (5696): 636-640.

Forrest, A. R., H. Kawaji, et al. (2014). "A promoter-level mammalian expression atlas." Nature 507(7493): 462-470.

Halder, G., P. Callaerts, et al. (1995). "Induction of ectopic eyes by targeted expression of the eyeless gene in *Drosophila*." Science 267(5205): 1788-1792.

Hoffman, M. M., J. Ernst, et al. (2013). "Integrative annotation of chromatin elements from ENCODE data." Nucleic Acids Res 41(2): 827-841.

Jacobson, S. G., G. M. Acland, et al. (2006). "Safety of recombinant adeno-associated virus type 2-RPE65 vector delivered by ocular subretinal injection." Mol Ther 13(6): 1074-1084.

Jacobson, S. G., A. V. Cideciyan, et al. (2015). "Improvement and Decline in Vision with Gene Therapy in Childhood Blindness." N Engl J Med 372(20): 1920-1926.

Jasin, M., M. E. Moynahan, et al. (1996). "Targeted transgenesis." Proc Natl Acad Sci USA 93(17): 8804-8808.

Kammandel, B., K. Chowdhury, et al. (1999). "Distinct cis-essential modules direct the time-space pattern of the Pax6 gene activity." Dev Biol 205(1): 79-97.

Kaspil, H., E. Chapnik, et al. (2013). "miR-290-295 Regulate Embryonic Stem Cell Differentiation Propensities by Repressing Pax6." Stem Cells.

Kleinjan, D. A., A. Seawright, et al. (2004). "Conserved elements in Pax6 intron 7 involved in (auto)regulation and alternative transcription." Dev Biol 265(2): 462-477.

Kleinjan, D. A., A. Seawright, et al. (2001). "Aniridia-associated translocations, DNase hypersensitivity, sequence comparison and transgenic analysis redefine the functional domain of PAX6." Hum Mol Genet 10(19): 2049-2059.

Manuel, M., T. Pratt, et al. (2008). "Overexpression of Pax6 results in microphthalmia, retinal dysplasia and defective retinal ganglion cell axon guidance." BMC Dev Biol 8: 59.

Mathelier, A., C. Lefebvre, et al. (2015). "Cis-regulatory somatic mutations and gene-expression alteration in B-cell lymphomas." Genome Biol 16: 84.

Mathelier, A., X. Zhao, et al. (2014). "JASPAR 2014: an extensively expanded and updated open-access database of transcription factor binding profiles." Nucleic Acids Res 42(Database issue): D142-147.

McBride, D. J., A. Buckle, et al. (2011). "DNaseI hypersensitivity and ultraconservation reveal novel, interdependent long-range enhancers at the complex Pax6 cis-regulatory region." PLoS ONE 6(12): e28616.

Pollard, K. S., M. J. Hubisz, et al. (2010). "Detection of nonneutral substitution rates on mammalian phylogenies." Genome Res 20(1): 110-121.

Portales-Casamar, E., D. Arenillas, et al. (2009). "The PAZAR database of gene regulatory information coupled to the ORCA toolkit for the study of regulatory sequences." Nucleic Acids Res 37(Database issue): D54-60.

Portales-Casamar, E., S. Kirov, et al. (2007). "PAZAR: A framework for collection and dissemination of cis-regulatory sequence annotation." Genome Biol 8: R207.

Portales-Casamar, E., D. J. Swanson, et al. (2010). "A regulatory toolbox of MiniPromoters to drive selective expression in the brain." Proc Natl Acad Sci USA 107(38): 16589-16594.

Portales-Casamar, E., S. Thongjuea, et al. (2010). "JASPAR 2010: the greatly expanded open-access database of transcription factor binding profiles." Nucleic Acids Res 38(Database issue): D105-110.

Sanyal, A., B. R. Lajoie, et al. (2012). "The long-range interaction landscape of gene promoters." Nature 489(7414): 109-113.

Schedl, A., A. Ross, et al. (1996). "Influence of PAX6 gene dosage on development: overexpression causes severe eye abnormalities." Cell 86(1): 71-82.

Servant, N., B. R. Lajoie, et al. (2012). "HiTC: exploration of high-throughput 'C' experiments." Bioinformatics 28(21): 2843-2844.

Shen, Y., F. Yue, et al. (2012). "A map of the cis-regulatory sequences in the mouse genome." Nature 488(7409): 116-120.

Teerawanichpan, P., T. Hoffman, et al. (2007). "Investigations of combinations of mutations in the jellyfish green fluorescent protein (GFP) that afford brighter fluorescence, and use of a version (VisGreen) in plant, bacterial, and animal cells." Biochim Biophys Acta 1770(9): 1360-1368.

van der Weyden, L., D. J. Adams, et al. (2002). "Tools for targeted manipulation of the mouse genome." Physiol Genomics 11(3): 133-164.

Worsley Hunt, R. and W. W. Wasserman (2014). "Non-targeted transcription factors motifs are a systemic component of ChIP-seq datasets." Genome Biol 15(7): 412.

Wu, D., T. Li, et al. (2006). "Effect of CTCF-binding motif on regulation of PAX6 transcription." Invest Ophthalmol Vis Sci 47(6): 2422-2429.

Xu, P. X., X. Zhang, et al. (1999). "Regulation of Pax6 expression is conserved between mice and flies." Development 126(2): 383-395.

Xu, Z. P. and G. F. Saunders (1997). "Transcriptional regulation of the human PAX6 gene promoter." J Biol Chem 272(6): 3430-3436.

Xu, Z. P. and G. F. Saunders (1998). "PAX6 intronic sequence targets expression to the spinal cord." Dev Genet 23(4): 259-263.

Zanta-Boussif, M. A., S. Charrier, et al. (2009). "Validation of a mutated PRE sequence allowing high and sustained transgene expression while abrogating WHV-X protein synthesis: application to the gene therapy of WAS." Gene Ther 16(5): 605-619.

Zhang, X., S. Rowan, et al. (2006). "Pax6 is regulated by Meis and Pbx homeoproteins during pancreatic development." Dev Biol 300(2): 748-757.

Zheng, J. B., Y. H. Zhou, et al. (2001). "Activation of the human PAX6 gene through the exon 1 enhancer by transcription factors SEF and Sp1." Nucleic Acids Res 29(19): 4070-4078.

Zolotukhin, S., M. Potter, et al. (2002). "Production and purification of serotype 1, 2, and 5 recombinant adeno-associated viral vectors." Methods 28(2): 158-167.

What is claimed is:

1. An isolated polynucleotide comprising a PAX6 MiniPromoter wherein the PAX6 MiniPromoter comprises at least one PAX6 regulatory element with at least 95% sequence identity to SEQ ID NO: 10-16 operably joined to a PAX6 basal promoter with at least 95% sequence identity to SEQ ID NO: 8 or 9 through a non-native spacing of not more than 500 nt. between the PAX6 regulatory element and the PAX6 basal promoter wherein the PAX6 MiniPromoter has at least 95% sequence identity with a sequence selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

2. The isolated polynucleotide of claim 1, operably linked to an expressible sequence.

3. The isolated polynucleotide of claim 1, operably linked to an expressible PAX6 sequence.

4. The isolated polynucleotide of claim 3, wherein the expressible PAX6 sequence has at least 95% sequence identity with SEQ ID NO: 17.

5. A vector comprising the isolated polynucleotide of claim 1.

6. An isolated cell comprising the vector of claim 5.

* * * * *